(12) United States Patent
Xie et al.

(10) Patent No.: US 7,271,170 B2
(45) Date of Patent: Sep. 18, 2007

(54) IMIDAZO-PYRIMIDINES AND TRIAZOLO-PYRIMIDINES: BENZODIAZEPINE RECEPTOR LIGANDS

(75) Inventors: Linghong Xie, Guilford, CT (US); Bingsong Han, North Haven, CT (US); Yuelian Xu, East Haven, CT (US); George Maynard, Clinton, CT (US); Bertrand L. Chenard, Waterford, CT (US); Kenneth Shaw, Weston, CT (US); Yang Gao, Branford, CT (US)

(73) Assignee: Neurogen Corporation, Branford, CT (US)

( * ) Notice: Subject to any disclaimer, the term of this patent is extended or adjusted under 35 U.S.C. 154(b) by 176 days.

(21) Appl. No.: 10/898,690

(22) Filed: Jul. 23, 2004

(65) Prior Publication Data

US 2005/0038043 A1 Feb. 17, 2005

Related U.S. Application Data

(60) Provisional application No. 60/543,083, filed on Feb. 9, 2004, provisional application No. 60/490,006, filed on Jul. 25, 2003.

(51) Int. Cl.
*C07D 487/04* (2006.01)
*A61K 31/519* (2006.01)
*A61P 25/24* (2006.01)
*A61P 25/22* (2006.01)
*A61P 25/20* (2006.01)

(52) U.S. Cl. .............. 514/259.1; 514/259.31; 514/259.3; 544/263; 544/281; 544/282

(58) Field of Classification Search ............. 544/263, 544/281, 282; 514/259.1, 259.31, 259.3
See application file for complete search history.

(56) References Cited

U.S. PATENT DOCUMENTS

| | | | |
|---|---|---|---|
| 6,982,268 B2 | 11/2003 | Xie et al. | |
| 6,737,242 B1 | 5/2004 | Tallman et al. | |
| 6,900,215 B2 * | 5/2005 | Chambers et al. | ....... 514/259.1 |
| 6,916,827 B2 | 7/2005 | Maynard et al. | |
| 7,030,144 B2 | 4/2006 | Maynard et al. | |
| 2004/0077653 A1 | 4/2004 | Xie et al. | |

FOREIGN PATENT DOCUMENTS

| | | |
|---|---|---|
| WO | WO-01/44249 | 6/2001 |
| WO | WO-02/02557 | 1/2002 |
| WO | WO-02/38569 | 5/2002 |
| WO | WO-02/50062 | 6/2002 |
| WO | WO-02/076983 | 10/2002 |
| WO | WO-03/006471 | 1/2003 |
| WO | WO-03/048132 | 6/2003 |
| WO | PCT/US04/13778 | 5/2004 |
| WO | WO 2004/041808 A1 | 5/2004 |

OTHER PUBLICATIONS

John E. Francis et al, J. Med. Chem., 1991, 34, 2899-2906.*
Pamela A. Albaugh et al, J. Med. Chem., 2002, 45, 5043-5051.*
U.S. Appl. No. 60/544,057, filed Feb. 2004, Xu et al.
Drug Evaluations Annual 1991 (American Medical Association), pp. 202-210.
Charney, Dennis S. et al., Hypnotics and Sedatives, in Goodman & Gilman's The Pharmacological Basis of Therapeutics, Tenth Edition (McGraw-Hill, 2001) pp. 399-412.

* cited by examiner

*Primary Examiner*—Mark L. Berch
*Assistant Examiner*—Susanna Moore
(74) *Attorney, Agent, or Firm*—Edwards Angell Palmer & Dodge LLP; Peter F. Corless; Mark D. Russett

(57) ABSTRACT

Compounds of Formula I

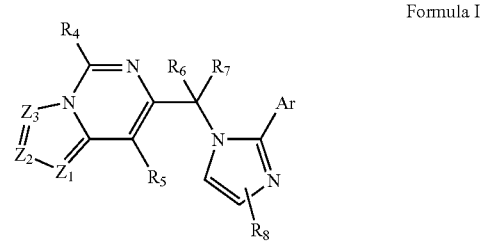

Formula I are provided, as are methods for their preparation. The variables $Z_1$, $Z_2$, $Z_3$, $R_4$, $R_5$, $R_6$, $R_7$, $R_8$ and Ar in the above formula are defined herein. Such compounds may be used to modulate ligand binding to $GABA_A$ receptors in vivo or in vitro, and are particularly useful in the treatment of a variety of central nervous system (CNS) disorders in humans, domesticated companion animals and livestock animals. Compounds provided herein may be administered alone or in combination with one or more other CNS agents to potentiate the effects of the other CNS agent(s). Pharmaceutical compositions and methods for treating such disorders are provided, as are methods for using such ligands for detecting $GABA_A$ receptors (e.g., receptor localization studies).

190 Claims, No Drawings

IMIDAZO-PYRIMIDINES AND TRIAZOLO-PYRIMIDINES: BENZODIAZEPINE RECEPTOR LIGANDS

CROSS-REFERENCE TO RELATED APPLICATION(S)

This application claims priority from U.S. Provisional Application Ser. No. 60/490,006, filed on Jul. 25, 2003 and U.S. Provisional Application Ser. No. 60/543,083, filed on Feb. 9, 2004.

FIELD OF THE INVENTION

The present invention relates generally to imidazopyrimidines and triazolopyrimidines that have useful pharmacological properties. The invention further relates to pharmaceutical compositions comprising such compounds and to the use of such compounds in the treatment of central nervous system (CNS) diseases.

BACKGROUND OF THE INVENTION

The $GABA_A$ receptor superfamily represents one of the classes of receptors through which the major inhibitory neurotransmitter γ-aminobutyric acid (GABA) acts. Widely, although unequally, distributed throughout the mammalian brain, GABA mediates many of its actions through interaction with a complex of proteins called the $GABA_A$ receptor, which causes alteration in chloride conductance and membrane polarization. A number of drugs, including the anxiolytic and sedating benzodiazepines, also bind to this receptor. The $GABA_A$ receptor comprises a chloride channel that opens in response to GABA, allowing chloride to enter the cell. This, in turn, effects a slowing of neuronal activity through hyperpolarization of the cell membrane potential.

$GABA_A$ receptors are composed of five protein subunits. A number of cDNAs for these $GABA_A$ receptor subunits have been cloned and their primary structures determined. While these subunits share a basic motif of 4 membrane-spanning helices, there is sufficient sequence diversity to classify them into several groups. To date, at least six α, three β, three γ, one ε, one δ and two ρ subunits have been identified. Native $GABA_A$ receptors are typically composed of two α subunits, two β subunits and one γ subunit. Various lines of evidence (such as message distribution, genome localization and biochemical study results) suggest that the major naturally occurring receptor combinations are $α_1β_2γ_2$, $α_2β_3γ_2$, $α_3β_3γ_2$ and $α_5β_3γ_2$.

The $GABA_A$ receptor binding sites for GABA (two per receptor complex) are formed by amino acids from the α and β subunits. Amino acids from the α and γ subunits together form one benzodiazepine site per receptor, at which benzodiazepines exert their pharmacological activity. In addition, the $GABA_A$ receptor contains sites of interaction for several other classes of drugs. These include a steroid binding site, a picrotoxin site and a barbiturate site. The benzodiazepine site of the $GABA_A$ receptor is a distinct site on the receptor complex that does not overlap with the sites of interaction for other classes of drugs or GABA.

In a classic allosteric mechanism, the binding of a drug to the benzodiazepine site alters the affinity of the GABA receptor for GABA. Benzodiazepines and related drugs that enhance the ability of GABA to open $GABA_A$ receptor channels are known as agonists or partial agonists, depending on the level of GABA enhancement. Other classes of drugs, such as β-carboline derivatives, that occupy the same site and negatively modulate the action of GABA are called inverse agonists. Those compounds that occupy the same site, and yet have little or no effect on GABA activity, can block the action of agonists or inverse agonists and are thus referred to as $GABA_A$ receptor antagonists.

The important allosteric modulatory effects of drugs acting at the benzodiazepine site were recognized early, and the distribution of activities at different receptor subtypes has been an area of intense pharmacological discovery. Agonists that act at the benzodiazepine site are known to exhibit anxiolytic, sedative, anticonvulsant and hypnotic effects, while compounds that act as inverse agonists at this site elicit anxiogenic, cognition enhancing and proconvulsant effects.

While benzodiazepines have enjoyed long pharmaceutical use, these compounds can exhibit a number of unwanted side effects. Accordingly, there is a need in the art for additional therapeutic agents that modulate $GABA_A$ receptor activation and/or activity. The present invention fulfills this need, and provides further related advantages.

SUMMARY OF THE INVENTION

The present invention provides imidazopyrimidines and triazolopyrimidines of Formula I:

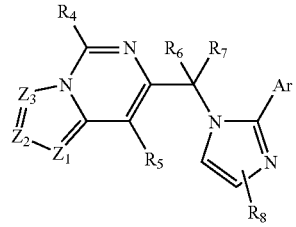

Formula I as well as pharmaceutically acceptable salts of such compounds, wherein:

$Z_1$ is nitrogen or $CR_1$; $Z_2$ is nitrogen or $CR_2$; $Z_3$ is nitrogen or $CR_3$; and at least one (but no more than two) of $Z_1$, $Z_2$ and $Z_3$ are nitrogen;

$R_1$, $R_2$, $R_3$ and $R_4$ are each independently selected from:
  (a) hydrogen, halogen, nitro and cyano; and
  (b) groups of the formula:

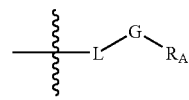

wherein:
  L is a bond or $C_1$–$C_8$alkylene;
  G is a bond,

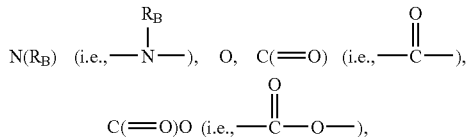

$N(R_B)$ (i.e., —N($R_B$)—), O, C(=O) (i.e., —C(=O)—),

C(=O)O (i.e., —C(=O)—O—),

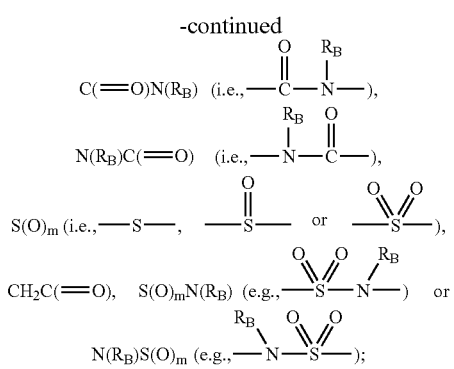

wherein m is 0, 1 or 2; and $R_A$ and each $R_B$ are independently selected from:
(i) hydrogen; and
(ii) $C_1$–$C_8$alkyl, $C_2$–$C_8$alkenyl, $C_2$–$C_8$alkynyl, ($C_3$–$C_8$cycloalkyl)$C_0$–$C_4$alkyl, (3- to 7-membered heterocycloalkyl)$C_0$–$C_4$alkyl, ($C_6$–$C_{10}$aryl)$C_0$–$C_2$alkyl and (5- to 10-membered heteroaryl)$C_0$–$C_2$alkyl, each of which is optionally substituted, and is preferably substituted with from 0 to 4 substituents independently selected from halogen, hydroxy, nitro, cyano, amino, $C_1$–$C_4$alkyl, $C_1$–$C_4$alkoxy, $C_1$–$C_4$alkanoyl, mono- and di($C_1$–$C_4$alkyl)amino, $C_1$–$C_4$haloalkyl and $C_1$–$C_4$haloalkoxy;

$R_5$ is:
(a) hydrogen, halogen or cyano; or
(b) $C_1$–$C_6$alkyl, $C_2$–$C_6$alkenyl, $C_2$–$C_6$alkynyl, $C_1$–$C_4$alkoxy, or mono- or di-($C_1$–$C_4$alkyl)amino, each of which is optionally substituted, and is preferably substituted with from 0 to 5 substituents independently chosen from halogen, hydroxy, nitro, cyano, amino, $C_1$–$C_4$alkoxy, $C_1$–$C_2$haloalkyl, $C_1$–$C_2$haloalkoxy, mono- and di-($C_1$–$C_4$alkyl)amino, $C_3$–$C_8$cycloalkyl, phenyl, phenyl $C_1$–$C_4$alkoxy and 5- or 6-membered heteroaryl;

$R_6$ and $R_7$ are independently hydrogen, methyl, ethyl or halogen;

$R_8$ represents 0, 1 or 2 substituents independently chosen from halogen, hydroxy, nitro, cyano, amino, $C_1$–$C_4$alkyl, $C_1$–$C_4$alkoxy, mono- and di($C_1$–$C_4$alkyl)amino, $C_3$–$C_7$cycloalkyl, $C_1$–$C_2$haloalkyl and $C_1$–$C_2$haloalkoxy; and Ar represents phenyl, naphthyl or 5- to 10-membered heteroaryl, each of which is optionally substituted, and is preferably substituted with from 0 to 4 substituents independently chosen from halogen, hydroxy, nitro, cyano, amino, $C_1$–$C_8$alkyl, $C_1$–$C_8$alkenyl, $C_1$–$C_8$alkynyl, $C_1$–$C_8$alkoxy, ($C_3$–$C_7$cycloalkyl)$C_0$–$C_4$alkyl, ($C_3$–$C_7$cycloalkyl)$C_1$–$C_4$alkoxy, $C_1$–$C_8$alkyl ether, $C_1$–$C_8$alkanone, $C_1$–$C_8$alkanoyl, (3- to 7-membered heterocycloalkyl)$C_0$–$C_4$alkyl, $C_1$–$C_8$haloalkyl, $C_1$–$C_8$haloalkoxy, oxo, $C_1$–$C_8$hydroxyalkyl, $C_1$–$C_8$aminoalkyl, and mono- and di-($C_1$–$C_8$alkyl)amino $C_0$–$C_8$alkyl.

Within certain aspects, such compounds are $GABA_A$ receptor modulators provided herein that modulate $GABA_A$ receptor activation and/or $GABA_A$ receptor-mediated signal transduction. Such $GABA_A$ receptor modulators are preferably high affinity and/or high selectivity $GABA_A$ receptor ligands and act as agonists, inverse agonists or antagonists of $GABA_A$ receptors, such as human $GABA_A$ receptors. As such, they are useful in the treatment of various CNS disorders.

Within further aspects, the present invention provides pharmaceutical compositions comprising one or more compounds or salts as described above in combination with a pharmaceutically acceptable carrier, diluent or excipient. Packaged pharmaceutical preparations are also provided, comprising such a pharmaceutical composition in a container and instructions for using the composition to treat a patient suffering from a CNS disorder such as anxiety, depression, a sleep disorder, attention deficit disorder, schizophrenia, or a cognitive disorder such as short-term memory loss or Alzheimer's dementia.

The present invention further provides, within other aspects, methods for treating patients suffering from certain CNS disorders, such as anxiety, depression, a sleep disorder, attention deficit disorder, schizophrenia or a cognitive disorder, comprising administering to a patient in need of such treatment a therapeutically effective amount of a compound as described above. Methods for improving short term memory in a patient are also provided, comprising administering to a patient in need of such treatment a therapeutically effective amount of a compound as described above. Treatment of humans, domesticated companion animals (pets) or livestock animals suffering from certain CNS disorders with a compound as provided herein is encompassed by the present invention.

In a separate aspect, the invention provides methods of potentiating the action of other CNS active compounds. These methods comprise administering to a patient a therapeutically effective amount of a compound or salt of Formula I in conjunction with the administration of a therapeutically effective amount of another CNS active compound.

The present invention further relates to the use of compounds of Formula I as probes for the localization of $GABA_A$ receptors in sample (e.g., a tissue section). In certain embodiments, $GABA_A$ receptors are detected using autoradiography. Additionally, the present invention provides methods for determining the presence or absence of $GABA_A$ receptor in a sample, comprising the steps of: (a) contacting a sample with a compound as described above under conditions that permit binding of the compound to $GABA_A$ receptor; (b) removing compound that is not bound to the $GABA_A$ receptor and (c) detecting compound bound to $GABA_A$ receptor.

In yet another aspect, the present invention provides methods for preparing the compounds disclosed herein, including the intermediates.

These and other aspects of the present invention will become apparent upon reference to the following detailed description.

DETAILED DESCRIPTION OF THE INVENTION

As noted above, the present invention provides imidazopyrimidines and triazolopyrimidines of Formula I, including imidazo[1,5-c]pyrimidines, imidazo[1,2-c]pyrimdines, [1,2,4]triazolo[4,3-c]pyrimidines and [1,2,4]triazolo[1,5-c]pyrimidines. Certain preferred compounds bind to $GABA_A$ receptor, preferably with high selectivity; more preferably such compounds further provide beneficial modulation of brain function. Without wishing to be bound to any particular theory of operation, it is believed that that interaction of such compounds with the benzodiazepine site of $GABA_A$ receptor results in the pharmacological effects of these compounds. Such compounds may be used in vitro or in vivo to determine the location of $GABA_A$ receptors or to modulate $GABA_A$ receptor activity in a variety of contexts.

Chemical Description and Terminology

Compounds provided herein are generally described using standard nomenclature. For compounds having asymmetric centers, it should be understood that (unless otherwise specified) all of the optical isomers and mixtures thereof are encompassed. All chiral (enantiomeric and diastereomeric) and racemic forms, as well as all geometric isomeric forms of a structure are intended, unless the specific stereochemistry or isomeric form is specifically indicated. Geometric isomers of olefins, C=N double bonds and the like may also be present in the compounds described herein, and all such stable isomers are contemplated in the present invention. Cis and trans geometric isomers are also contemplated and may be isolated as a mixture of isomers or as separated isomeric forms. Compounds in which one or more atoms are replaced with an isotope (i.e., an atom having the same atomic number but a different mass number) are also contemplated. By way of general example, and without limitation, isotopes of hydrogen include tritium and deuterium, and isotopes of carbon include $^{11}C$, $^{13}C$ and $^{14}C$.

Certain compounds are described herein using a general formula that includes variables. Unless otherwise specified, each variable within such a formula is defined independently of other variables, and any variable that occurs more than one time within a formula is defined independently at each occurrence. Thus, for example, if a group is described as being substituted with 0–2 R*, then the group may be unsubstituted or substituted with up to two R* groups and R* at each occurrence is selected independently from the definition of R*. In addition, it will be apparent that combinations of substituents and/or variables are permissible only if such combinations result in a stable compound (i.e., a compound that can be isolated, characterized and tested for biological activity).

A "pharmaceutically acceptable salt" is an acid or base salt form of a compound, which salt form is suitable for use in contact with the tissues of human beings or animals without excessive toxicity or carcinogenicity, and preferably without irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic hydroiodic, phenylacetic, alkanoic such as acetic, $HOOC-(CH_2)_n-COOH$ where n is 0–4, and the like. Similarly, pharmaceutically acceptable cations include, but are not limited to sodium, potassium, calcium, aluminum, lithium and ammonium. Those of ordinary skill in the art will recognize further pharmaceutically acceptable salts for the compounds provided herein, including those listed by *Remington's Pharmaceutical Sciences*, 17th ed., Mack Publishing Company, Easton, Pa., p. 1418 (1985). In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two; generally, the use of nonaqueous media, such as ether, ethyl acetate, ethanol, isopropanol or acetonitrile, is preferred.

It will be apparent that each compound of Formula I may, but need not, be formulated as a hydrate, solvate or non-covalent complex. In addition, the various crystal forms and polymorphs are within the scope of the present invention. Also provided herein are prodrugs of the compounds of Formula I. A "prodrug" is a compound that may not fully satisfy the structural requirements of the compounds provided herein, but is modified in vivo, following administration to a patient, to produce a compound of Formula I, or other formula provided herein. For example, a prodrug may be an acylated derivative of a compound as provided herein. Prodrugs include compounds wherein hydroxy, amine or sulfhydryl groups are bonded to any group that, when administered to a mammalian subject, cleaves to form a free hydroxy, amino, or sulfhydryl group, respectively. Examples of prodrugs include, but are not limited to, acetate, formate and benzoate derivatives of alcohol and amine functional groups within the compounds provided herein. Prodrugs of the compounds provided herein may be prepared by modifying functional groups present in the compounds in such a way that the modifications are cleaved in vivo to yield the parent compounds.

A "substituent," as used herein, refers to a molecular moiety that is covalently bonded to an atom within a molecule of interest. For example, a "ring substituent" may be a moiety such as a halogen, alkyl group, haloalkyl group or other substituent discussed herein that is covalently bonded to an atom (preferably a carbon or nitrogen atom) that is a ring member. The term "substitution" refers to replacing a hydrogen atom in a molecular structure with a substituent as described above, such that the valence on the designated atom is not exceeded, and such that a chemically stable compound (i.e., a compound that can be isolated, characterized, and tested for biological activity) results from the substitution. When a substituent is oxo (i.e., =O), then 2 hydrogens on the atom are replaced. When aromatic moieties are substituted with an oxo group, the aromatic ring is replaced by the corresponding partially unsaturated ring.

The phrase "optionally substituted" indicates that a group may either be unsubstituted or substituted at one or more of any of the available positions, typically 1, 2, 3, 4 or 5 positions, by one or more suitable substituents such as those disclosed herein. Optional substitution is also indicated by the phrase "substituted with from 0 to X substituents," in which X is the maximum number of substituents.

A dash ("—") that is not between two letters or symbols is used to indicate a point of attachment for a substituent. For example, —$CONH_2$ is attached through the carbon atom.

As used herein, "alkyl" is intended to include both branched and straight-chain saturated aliphatic hydrocarbon groups; where specified, such a group has the indicated number of carbon atoms. Thus, the term $C_1-C_6$alkyl, as used herein, indicates an alkyl group having from 1 to 6 carbon atoms. "$C_0-C_4$alkyl" refers to a bond or a $C_1-C_4$alkyl group. Alkyl groups include groups having from 1 to 8 carbon atoms ($C_1-C_8$alkyl), from 1 to 6 carbon atoms ($C_1-C_6$alkyl) and from 1 to 4 carbon atoms ($C_1-C_4$alkyl), such as methyl, ethyl, n-propyl, isopropyl, n-butyl, sec-butyl, tert-butyl, pentyl, 2-pentyl, isopentyl, neopentyl, hexyl, 2-hexyl, 3-hexyl and 3-methylpentyl. In certain embodiments, preferred alkyl groups are methyl, ethyl, propyl, butyl and 3-pentyl. "Aminoalkyl" is an alkyl group as defined herein substituted with one or more —NH$_2$ substituents. "Hydroxyalkyl" is an alkyl group as defined herein substituted with one or more —OH substituents.

"Alkenyl" refers to a straight or branched hydrocarbon chain comprising one or more carbon-carbon double bonds, such as ethenyl and propenyl. Alkenyl groups include C$_2$–C$_8$alkenyl, C$_2$–C$_6$alkenyl and C$_2$–C$_4$alkenyl groups (which have from 2 to 8, 2 to 6 or 2 to 4 carbon atoms, respectively), such as ethenyl, allyl or isopropenyl.

"Alkynyl" refers to straight or branched hydrocarbon chains comprising one or more carbon-carbon triple bonds. Alkynyl groups include C$_2$–C$_8$alkynyl, C$_2$–C$_6$alkynyl and C$_2$–C$_4$alkynyl groups, which have from 2 to 8, 2 to 6 or 2 to 4 carbon atoms, respectively. Alkynyl groups include, for example, groups such as ethynyl and propynyl.

By "alkoxy," as used herein, is meant an alkyl, alkenyl or alkynyl group as described above attached via an oxygen bridge. Alkoxy groups include C$_1$–C$_6$alkoxy and C$_1$–C$_4$alkoxy groups, which have from 1 to 6 or 1 to 4 carbon atoms, respectively. Methoxy, ethoxy, propoxy, isopropoxy, n-butoxy, sec-butoxy, tert-butoxy, n-pentoxy, 2-pentoxy, 3-pentoxy, isopentoxy, neopentoxy, hexoxy, 2-hexoxy, 3-hexoxy and 3-methylpentoxy are specific alkoxy groups. Similarly "alkylthio" refers to an alkyl, alkenyl or alkynyl group as described above attached via a sulfur bridge.

A "cycloalkyl" is a saturated or partially saturated cyclic group in which all ring members are carbon, such as cyclopropyl, cyclobutyl, cyclopentyl, cyclohexyl, cycloheptyl, cyclooctyl, norbornyl, adamantyl, decahydro-naphthalenyl, octahydro-indenyl, and partially saturated variants of any of the foregoing, such as cyclohexenyl. Such groups typically contain from 3 to about 10 ring carbon atoms; in certain embodiments, such groups have from 3 to 7 ring carbon atoms (i.e., C$_3$–C$_7$cycloalkyl). If substituted, any ring carbon atom may be bonded to any indicated substituent.

In the term "(cycloalkyl)alkyl," "cycloalkyl" and "alkyl" are as defined above, and the point of attachment is on the alkyl group. Certain such groups are (C$_3$–C$_7$cycloalkyl)C$_0$–C$_4$alkyl, in which the cycloalkyl group is linked via a direct bond or a C$_1$–C$_4$alkyl. This term encompasses, for example, cyclopropylmethyl, cyclohexylmethyl and cyclohexylethyl. Similarly, "(C$_3$–C$_7$cycloalkyl)C$_1$–C$_4$alkoxy" refers to a C$_3$–C$_7$cycloalkyl group linked via a C$_1$–C$_4$alkoxy.

The term "alkanoyl" refers to an alkyl group as defined above attached through a carbonyl bridge. Alkanoyl groups include C$_2$–C$_8$alkanoyl, C$_2$–C$_6$alkanoyl and C$_2$–C$_4$alkanoyl groups, which have from 2 to 8, 2 to 6 or 2 to 4 carbon atoms, respectively. "C$_1$alkanoyl" refers to —(C=O)—H, which (along with C$_2$–C$_8$alkanoyl) is encompassed by the term "C$_1$–C$_8$alkanoyl." Ethanoyl is C$_2$alkanoyl.

The term "oxo," as used herein, refers to a keto (C=O) group. An oxo group that is a substituent of a nonaromatic ring results in a conversion of —CH$_2$— to —C(=O)—. It will be apparent that the introduction of an oxo substituent on an aromatic ring destroys the aromaticity.

An "alkanone" is a ketone group in which carbon atoms are in a linear or branched alkyl arrangement. "C$_3$–C$_8$alkanone," "C$_3$–C$_6$alkanone" and "C$_3$–C$_4$alkanone" refer to an alkanone having from 3 to 8, 6 or 4 carbon atoms, respectively. By way of example, a C$_3$ alkanone group has the structure —CH$_2$—(C=O)—CH$_3$.

Similarly, "alkyl ether" refers to a linear or branched ether substituent linked via a carbon-carbon bond. Alkyl ether groups include C$_2$–C$_8$alkyl ether, C$_2$–C$_6$alkyl ether and C$_2$–C$_4$alkyl ether groups, which have 2 to 8, 6 or 4 carbon atoms, respectively. By way of example, a C$_2$ alkyl ether group has the structure —CH$_2$—O—CH$_3$.

The term "alkoxycarbonyl" refers to an alkoxy group linked via a carbonyl (i.e., a group having the general structure —C(=O)—O—alkyl). Alkoxycarbonyl groups include C$_2$–C$_8$, C$_2$–C$_6$ and C$_2$–C$_4$alkoxycarbonyl groups, which have from 2 to 8, 6 or 4 carbon atoms, respectively. "C$_1$alkoxycarbonyl" refers to —C(=O)—OH, which is encompassed by the term "C$_1$–C$_8$alkoxycarbonyl." Such groups may also be referred to as alkylcarboxylate groups. For example, methyl carboxylate refers to —C(=O)—O—CH$_3$ and ethyl carboxylate refers to —C(=O)—O—CH$_2$CH$_3$.

The term "carboxamido" refers to an amide group (i.e., —(C=O)NH$_2$).

"Alkylamino" refers to a secondary or tertiary amine substituent having the general structure —NH—alkyl or —N(alkyl)(alkyl), wherein each alkyl may be the same or different. Such groups include, for example, mono- and di-(C$_1$–C$_6$alkyl)amino groups, in which each alkyl may be the same or different and may contain from 1 to 6 carbon atoms, as well as mono- and di-(C$_1$–C$_4$alkyl)amino groups. Alkylaminoalkyl refers to an alkylamino group linked via an alkyl group (i.e., a group having the general structure -alkyl-NH-alkyl or -alkyl-N(alkyl)(alkyl)). Such groups include, for example, mono- and di-(C$_1$–C$_8$alkyl)amino C$_1$–C$_8$alkyl, in which each alkyl may be the same or different. "Mono- or di-(C$_1$–C$_8$alkyl)amino C$_0$–C$_8$alkyl" refers to a mono- or di-(C$_1$–C$_8$alkyl)amino group linked via a direct bond or a C$_1$–C$_8$alkyl group. The following are representative alkylaminoalkyl groups:

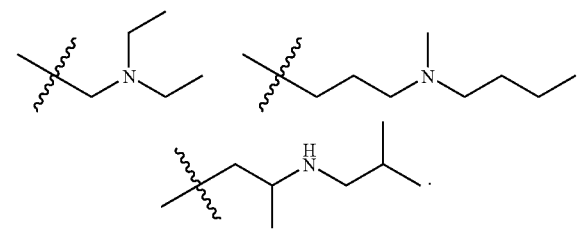

The term "halogen" refers to fluorine, chlorine, bromine and iodine. A "haloalkyl" is a branched or straight-chain alkyl group, substituted with 1 or more halogen atoms (e.g., "C$_1$–C$_8$haloalkyl" groups have from 1 to 8 carbon atoms; "C$_1$–C$_2$haloalkyl" groups have from 1 to 2 carbon atoms). Examples of haloalkyl groups include, but are not limited to, mono-, di- or tri-fluoromethyl; mono-, di- or tri-chloromethyl; mono-, di-, tri-, tetra- or penta-fluoroethyl; and mono-, di-, tri-, tetra- or penta-chloroethyl. Typical haloalkyl groups are trifluoromethyl and difluoromethyl. The term "haloalkoxy" refers to a haloalkyl group as defined above attached via an oxygen bridge. "C$_1$–C$_8$haloalkoxy" groups have from 1 to 8 carbon atoms.

As used herein, the term "aryl" indicates aromatic groups containing only carbon in the aromatic ring(s). Such aromatic groups may be further substituted with carbon or non-carbon atoms or groups. Typical aryl groups contain 1 to 3 separate, fused, spiro or pendant rings and from 6 to about 18 ring atoms, without heteroatoms as ring members. Preferred aryl groups are 6- to 12-membered groups, such as phenyl, naphthyl (including 1-naphthyl and 2-naphthyl) and biphenyl. Arylalkyl groups are aryl groups linked via an alkyl group; arylalkoxy groups are aryl groups linked via an alkoxy moiety. For example, phenylC$_1$–C$_2$alkoxy refers to benzyloxy or phenylethoxy (also known as phenethyloxy).

The term "heterocycle" or "heterocyclic group" is used to indicate saturated, partially unsaturated or aromatic groups having 1 or 2 rings, with 3 to 8 atoms in each ring, and in at least one ring from 1 to 4 independently chosen heteroatoms (i.e., oxygen, sulfur or nitrogen). The heterocyclic ring may be attached via any ring heteroatom or carbon atom that results in a stable structure, and may be substituted on carbon and/or nitrogen atom(s) if the resulting compound is stable. Any nitrogen and/or sulfur heteroatoms may optionally be oxidized, and any nitrogen may optionally be quaternized.

Certain heterocycles are "heteroaryl" (i.e., comprise at least one aromatic ring having from 1 to 4 heteroatoms, with the remaining ring atoms being carbon), such as 5- to 7-membered monocyclic groups and 7- to 10-membered bicyclic groups. When the total number of S and O atoms in the heteroaryl group exceeds 1, then these heteroatoms are not adjacent to one another; preferably the total number of S and O atoms in the heteroaryl group is not more than 1, 2 or 3, more preferably not more than 1 or 2 and most preferably not more than 1. Examples of heteroaryl groups include pyridyl, indolyl, pyrimidinyl, pyridazinyl, pyrazinyl, imidazolyl, oxazolyl, thienyl, thiazolyl, triazolyl, isoxazolyl, quinolinyl, pyrrolyl, pyrazolyl and 5,6,7,8-tetrahydroisoquinoline. Bicyclic heteroaryl groups may, but need not, contain a saturated ring in addition to the aromatic ring (e.g., a tetrahydroquinolinyl or tetrahydroisoquinolinyl group). A "5- or 6-membered heteroaryl" is a monocyclic heteroaryl having 5 or 6 ring members.

Other heterocycles are referred to herein as "heterocycloalkyl" (i.e., saturated or partially saturated heterocycles). Heterocycloalkyl groups have from 3 to about 8 ring atoms, and more typically from 3 to 7 (or from 5 to 7) ring atoms. Examples of heterocycloalkyl groups include morpholinyl, piperazinyl and pyrrolidinyl. A (3- to 6-membered heterocycloalkyl)C$_0$–C$_4$alkyl group is a heterocycloalkyl group having from 3 to 6 ring members that is linked via a direct bond or a C$_1$–C$_4$alkyl group. Examples of heterocycloalkyl groups include morpholinyl, piperazinyl and pyrrolidinyl groups.

The terms "GABA$_A$ receptor" and "benzodiazepine receptor" refer to a protein complex that detectably binds GABA and mediates a dose dependent alteration in chloride conductance and membrane polarization. Receptors comprising naturally-occurring mammalian (especially human or rat) GABA$_A$ receptor subunits are generally preferred, although subunits may be modified provided that any modifications do not substantially inhibit the receptor's ability to bind GABA (i.e., at least 50% of the binding affinity of the receptor for GABA is retained). The binding affinity of a candidate GABA$_A$ receptor for GABA may be evaluated using a standard ligand binding assay as provided herein. It will be apparent that there are a variety of GABA$_A$ receptor subtypes that fall within the scope of the term "GABA$_A$ receptor." These subtypes include, but are not limited to, $\alpha_2\beta_3\gamma_2$, $\alpha_3\beta_3\gamma_2$, $\alpha_5\beta_3\gamma_2$ and $\alpha_1\beta_2\gamma_2$ receptor subtypes. GABA$_A$ receptors may be obtained from a variety of sources, such as from preparations of rat cortex or from cells expressing cloned human GABA$_A$ receptors. Particular subtypes may be readily prepared using standard techniques (e.g., by introducing mRNA encoding the desired subunits into a host cell, as described herein).

An "agonist" of a GABA$_A$ receptor is a compound that enhances the activity of GABA at the GABA$_A$ receptor. Agonists may, but need not, also enhance the binding of GABA to GABA$_A$ receptor. The ability of a compound to act as a GABA$_A$ agonist may be determined using an electrophysiological assay, such as the assay provided in Example 7.

An "inverse agonist" of a GABA$_A$ receptor is a compound that reduces the activity of GABA at the GABA$_A$ receptor. Inverse agonists, but need not, may also inhibit binding of GABA to the GABA$_A$ receptor. The reduction of GABA-induced GABA$_A$ receptor activity may be determined from an electrophysiological assay such as the assay of Example 7.

An "antagonist" of a GABA$_A$ receptor, as used herein, is a compound that occupies the benzodiazepine site of the GABA$_A$ receptor, but has no detectable effect on GABA activity at the GABA$_A$ receptor. Such compounds can inhibit the action of agonists or inverse agonists. GABA$_A$ receptor antagonist activity may be determined using a combination of a suitable GABA$_A$ receptor binding assay, such as the assay provided in Example 6, and a suitable functional assay, such as the electrophysiological assay provided in Example 7, herein.

A "GABA$_A$ receptor modulator" is any compound that acts as a GABA$_A$ receptor agonist, inverse agonist or antagonist. In certain embodiments, such a modulator may exhibit an affinity constant (K$_i$) of less than 1 micromolar in a standard GABA$_A$ receptor radioligand binding assay, or an EC$_{50}$ of less than 1 micromolar in an electrophysiological assay. In other embodiments a GABA$_A$ receptor modulator may exhibit an affinity constant or EC$_{50}$ of less than 500 nM, 200 nM, 100 nM, 50 nM, 25 nM, 10 nM or 5 nM.

A GABA$_A$ receptor modulator is said to have "high affinity" if the K$_i$ at a GABA$_A$ receptor is less than 1 micromolar, preferably less than 100 nanomolar or less than 10 nanomolar. A representative assay for determining K$_i$ at GABA$_A$ receptor is provided in Example 6, herein. It will be apparent that the K$_i$ may depend upon the receptor subtype used in the assay. In other words, a high affinity compound may be "subtype-specific" (i.e., the K$_i$ is at least 10-fold greater for one subtype than for another subtype). Such compounds are said to have high affinity for GABA$_A$ receptor if the K$_i$ for at least one GABA$_A$ receptor subtype meets any of the above criteria.

A GABA$_A$ receptor modulator is said to have "high selectivity" if it binds to at least one subtype of GABA$_A$ receptor with a K$_i$ that is at least 10-fold lower, preferably at least 100-fold lower, than the K$_i$ for binding to other (i.e., not GABA$_A$) membrane-bound receptors. In particular, a compound that displays high selectivity should have a K$_i$ that is at least 10-fold greater at the following receptors than at a GABA$_A$ receptor: serotonin, dopamine, galanin, VR1, C5a, MCH, NPY, CRF, bradykinin and tackykinin. Assays to determine K$_i$ at other receptors may be performed using standard binding assay protocols, such as using a commercially available membrane receptor binding assay (e.g., the binding assays available from MDS PHARMA SERVICES, Toronto, Canada and CEREP, Redmond, Wash.).

A "CNS disorder" is a disease or condition of the central nervous system that is responsive to GABA$_A$ receptor modulation in the patient. Such disorders include anxiety disorders (e.g., panic disorder, obsessive compulsive disorder, agoraphobia, social phobia, specific phobia, dysthymia, adjustment disorders, separation anxiety, cyclothymia and generalized anxiety disorder), stress disorders (e.g., post-traumatic stress disorder, anticipatory anxiety acute stress disorder and acute stress disorder), depressive disorders (e.g., depression, atypical depression, bipolar disorder and depressed phase of bipolar disorder), sleep disorders (e.g., primary insomnia, circadian rhythm sleep disorder, dyssomnia NOS, parasomnias including nightmare disorder, sleep terror disorder, sleep disorders secondary to depression, anxiety and/or other mental disorders and substance-induced sleep disorder), cognitive disorders (e.g., cognition impairment, mild cognitive impairment (MCI), age-related cognitive decline (ARCD), schizophrenia, traumatic brain injury, Down's Syndrome, neurodegenerative diseases such as Alzheimer's disease and Parkinson's disease and stroke), AIDS-associated dementia, dementia associated with depression, anxiety or psychosis, attention deficit disorders (e.g., attention deficit disorder and attention deficit and hyperactivity disorder), convulsive disorders (e.g., epilepsy), benzodiazepine overdose and drug and alcohol addiction.

A "CNS agent" is any drug used to treat or prevent a CNS disorder or to induce or prolong sleep in a healthy patient. CNS agents include, for example: $GABA_A$ receptor modulators, serotonin receptor (e.g., $5-HT_{1A}$) agonists and antagonists and selective serotonin reuptake inhibitors (SSRIs); neurokinin receptor antagonists; corticotropin releasing factor receptor ($CRF_1$) antagonists; melatonin receptor agonists; nicotinic agonists; muscarinic agents; acetylcholinesterase inhibitors and dopamine receptor agonists.

A "therapeutically effective amount" (or dose) is an amount that, upon administration to a patient, results in a discernible patient benefit (e.g., diminution of one or more symptoms of a CNS disorder or a desired effect on sleep). Such an amount or dose generally results in a concentration of compound in cerebrospinal fluid that is sufficient to inhibit the binding of $GABA_A$ receptor ligand to $GABA_A$ receptor in vitro, as determined using the assay described in Example 6. It will be apparent that the therapeutically effective amount for a compound will depend upon the indication for which the compound is administered, as well as any co-administration of other CNS agent(s).

A "patient" is any individual treated with a compound provided herein. Patients include humans, as well as other vertebrate animals such as companion animals and livestock. Patients may be afflicted with a CNS disorder, or may be free of such a condition (i.e., treatment may be prophylactic or soporific).

Imidazopyrimidines and Triazolopyrimidines

As noted above, the present invention provides compounds of Formula I, with the variables as described above, as well as pharmaceutically acceptable salts of such compounds.

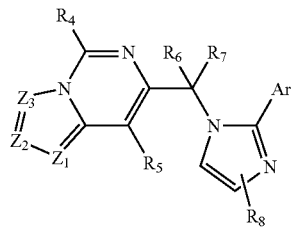

Formula I

In certain compounds provided herein, $R_8$ represents 0 substituents or 1 substituent selected from halogen, $C_1$–$C_2$alkyl and $C_1$–$C_2$alkoxy.

Ar, within certain compounds of Formula I, is substituted with 0, 1, 2 or 3 substituents independently selected from halogen, hydroxy, amino, cyano, $C_1$–$C_4$alkyl, $C_1$–$C_4$alkoxy, mono- or di-$c_1$–$C_4$alkylamino, $C_2$–$C_4$alkanoyl, ($C_3$–$C_7$cycloalkyl)$C_0$–$C_2$alkyl, $C_1$–$C_2$haloalkyl and $C_1$–$C_2$haloalkoxy.

In certain embodiments, Ar is phenyl, pyridyl, thiazolyl, thienyl, pyridazinyl or pyrimidinyl, each of which is substituted with from 0 to 4 substituents as described above, or substituted with from 0 to 3 substituents independently selected from chloro, fluoro, hydroxy, cyano, amino, $C_1$–$C_4$alkyl, $C_1$–$C_4$alkoxy, $C_1$–$C_2$alkylamino, $C_1$–$C_2$haloalkyl and $C_1$–$C_2$haloalkoxy. Representative Ar groups include phenly, pyridyl (e.g., pyridin-2-yl), thiazolyl (e.g., 1,3-thiazol-2-yl), thienyl (e.g., thien-2-yl) or pyridazinyl (e.g., pyridazin-3-yl), each of which is substituted with from 0 to 3 substituents independently selected from chloro, fluoro, hydroxy, cyano, amino, $C_1$–$C_4$alkyl, $C_1$–$C_4$alkoxy, mono- or di-($C_1$–$C_2$)alkylamino, $C_1$–$C_2$alkyl and $C_1$–$C_2$alkoxy; preferably each of which is substituted with from 0 to 3 substituents independently selected from fluoro, chloro, hydroxy, $C_1$–$C_2$alkyl, cyano and $C_1$–$C_2$alkoxy. For example, Ar groups include, but are not limited to, 2,6-difluoro-phenyl, 2,5-difluoro-phenyl, 5-fluoro-2-methyl-phenyl, pyridine-2-yl, 3-fluoro-pyridin-2-yl, 3-cyano-pyridin-2yl, 3-trifluoromethyl-pyridin-2-yl, 3-hydroxy-pyridin-2-yl, 3-methoxy-pyridin-2-yl, 6-fluoro-pyridin-2-yl, 6-cyano-pyridin-2-yl, 6-trifluoromethyl-pyridin-2-yl, 6-hydroxy-pyridin-2-yl and 6-methoxy-pyridin-2-yl.

$R_1$, $R_2$, $R_3$ and $R_4$, in certain compounds, are independently selected from:
(a) hydrogen, halogen or cyano; and
(b) groups of the formula:

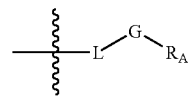

wherein:
(i) L is a bond;
(ii) G is a bond, NH, N($R_B$), O, C(=O)O or C(=O); and
(iii) $R_A$ and $R_B$ are independently selected from (1) hydrogen and (2) $C_1$–$C_6$alkyl, $C_2$–$C_6$alkenyl, ($C_3$–$C_7$cycloalkyl)$C_0$–$C_2$alkyl, (3- to 7-membered heterocycloalkyl)$C_0$–$C_2$alkyl, phenyl, thienyl, pyridyl, pyrimidinyl, thiazolyl and pyrazinyl, each of which is substituted with from 0 to 4 substituents independently selected from hydroxy, halogen, cyano, amino, $C_1$–$C_2$alkyl and $C_1$–$C_2$alkoxy.

For example, $R_1$, $R_2$, $R_3$ and $R_4$ are independently selected, in certain compounds, from hydrogen, hydroxy, halogen, cyano, carboxamido, $C_1$–$C_6$alkyl, $C_1$–$C_6$alkoxy, $C_2$–$C_6$alkyl ether, $C_3$–$C_7$cycloalkyl, $C_1$–$C_2$hydroxyalkyl, Cl-$c_2$haloalkyl, $C_1$–$C_2$haloalkoxy, $C_1$–$C_6$alkoxycarbonyl, mono- and di-($C_1$–$C_4$alkyl)amino, phenyl and pyridyl. Representative $R_1$ and $R_4$ groups include hydrogen, methyl and ethyl. Representative $R_2$ groups include hydrogen, cyano, carboxamido, $C_1$–$C_4$alkyl, $C_1$–$C_4$alkoxy, $C_1$–$C_4$alkoxycarbonyl, $C_2$–$C_4$alkyl ether, $C_3$–$C_7$cycloalkyl, $C_1$–$C_2$hydroxyalkyl, fluoromethyl, difluoromethyl, trifluoromethyl, phenyl and pyridyl.

In certain compounds of Formula I, $R_5$ is $C_1$–$C_6$alkyl, $C_2$–$C_6$alkenyl, $C_1$–$C_4$alkoxy or mono- or di-$C_1$–$C_4$akyklyamino, each of which is substituted with from 0 to 3 substituents independently selected from halogen, hydroxy, $C_1$–$C_2$alkoxy, $C_3$–$C_8$cycloalkyl, phenyl and phenylC$_1$–C$_2$alkoxy. Representative R$_5$ groups include ethyl, propyl, butyl, ethoxy and methoxymethyl.

R$_6$ and R$_7$, within certain embodiments, are both hydrogen.

Certain compounds of Formula I further satisfy Formula II, in which Z$_1$ is nitrogen, Z$_2$ is CR$_2$ and Z$_3$ is CR$_3$:

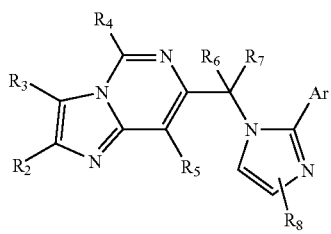

Formula II

In certain such compounds, R$_2$ and R$_3$ are independently selected from hydrogen, cyano, carboxamido, C$_1$–C$_4$alkyl, C$_1$–C$_4$alkoxy, trifluoromethyl, phenyl, pyridyl, methylcarboxylate and ethylcarboxylate. Within other such compounds:

R$_2$ and R$_3$ are independently selected from hydrogen, hydroxy, halogen, cyano, carboxamido, C$_1$–C$_6$alkyl, C$_1$–C$_6$alkoxy, C$_3$–C$_7$cycloalkyl, C$_2$–C$_6$alkyl ether, C$_1$–C$_4$hydroxyalkyl, C$_1$–C$_2$haloalkyl, C$_1$–C$_2$haloalkoxy, C$_1$–C$_4$alkoxycarbonyl, mono- and di-(C$_1$–C$_4$alkyl)amino, phenyl and pyridyl;

R$_4$ is hydrogen or C$_1$–C$_4$alkyl;

R$_5$ is C$_1$–C$_6$ alkyl, C$_2$–C$_6$ alkenyl, C$_1$–C$_4$ alkoxy, or mono- or di-C$_1$–C$_4$alkylamino, each of which is substituted with from 0 to 3 substituents independently selected from halogen, hydroxy, C$_1$–C$_2$alkoxy, C$_3$–C$_8$cycloalkyl, phenyl and phenylC$_1$–C$_2$alkoxy;

R$_6$ and R$_7$ are independently hydrogen, methyl, ethyl or halogen;

R$_8$ represents 0 or 1 substituent selected from halogen, C$_1$–C$_2$alkyl and C$_1$–C$_2$alkoxy; and/or Ar represents phenyl, 2-pyridyl, 1,3-thiazol-2-yl, 2-thienyl or 3-pyridazinyl, each of which is substituted with from 0 to 3 substituents independently selected from fluoro, hydroxy, C$_1$–C$_2$alkyl, C$_1$–C$_2$haloalkyl, cyano and C$_1$–C$_2$alkoxy.

Certain compounds of Formula I further satisfy Formula III, in which Z$_1$ and Z$_3$ are nitrogen, and Z$_2$ is CR$_2$:

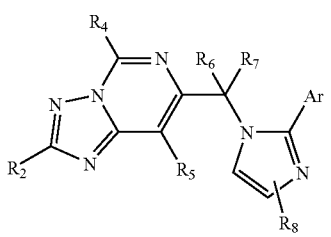

Formula III

In certain such compounds, R$_2$ is selected from hydrogen, C$_1$–C$_4$alkyl, C$_1$–C$_4$alkoxy, C$_3$–C$_7$cycloalkyl, C$_2$–C$_4$alkyl ether, C$_1$–C$_2$hydroxyalkyl, fluoromethyl, difluoromethyl, trifluoromethyl, phenyl and pyridyl. In other such compounds:

R$_2$ is selected from hydrogen, hydroxy, halogen, cyano, carboxamido, C$_1$–C$_6$alkyl, C$_1$–C$_6$alkoxy, C$_3$–C$_7$cycloalkyl, C$_2$–C$_6$alkyl ether, C$_1$–C$_4$hydroxyalkyl, C$_1$–C$_2$haloalkyl, C$_1$–C$_2$haloalkoxy, C$_1$–C$_4$alkoxycarbonyl, mono- and di-(C$_1$–C$_4$alkyl)amino, phenyl and pyridyl;

R$_4$ is hydrogen or C$_1$–C$_4$alkyl;

R$_5$ is C$_1$–C$_6$alkyl, C$_2$–C$_6$alkenyl, C$_1$–C$_4$alkoxy, or mono- or di-c$_1$–C$_4$alkylamino, each of which is substituted with from 0 to 3 substituents independently selected from halogen, hydroxy, C$_1$–C$_2$alkoxy, C$_3$–C$_8$cycloalkyl, phenyl and phenylC$_1$–C$_2$alkoxy;

R$_6$ and R$_7$ are independently hydrogen, methyl, ethyl or halogen;

R$_8$ represents 0 or 1 substituent selected from halogen, C$_1$–C$_2$alkyl and C$_1$–C$_2$alkoxy; and/or Ar represents phenyl, 2-pyridyl, 1,3-thiazol-2-yl, 2-thienyl or 3-pyridazinyl, each of which is substituted with from 0 to 3 substituents independently selected from fluoro, hydroxy, C$_1$–C$_2$alkyl, C$_1$–C$_2$haloalkyl, cyano and C$_1$–C$_2$alkoxy.

Certain-compounds of Formula I further satisfy Formula IV, in which Z$_1$ is CR$_1$, Z$_2$ is nitrogen and Z$_3$ is CR$_3$:

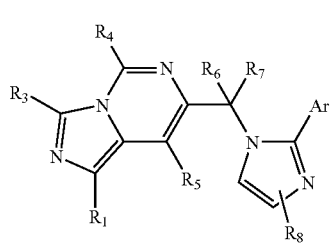

Formula IV

In certain such compounds, R$_3$ is hydrogen or methyl. In other such compounds:

R$_1$ is hydrogen, halogen or C$_1$–C$_6$alkyl;

R$_3$ is selected from hydrogen, hydroxy, halogen, cyano, carboxamido, C$_1$–C$_6$alkyl, C$_1$–C$_6$alkoxy, C$_3$–C$_7$cycloalkyl, C$_2$–C$_6$alkyl ether, C$_1$–C$_4$hydroxyalkyl, C$_1$–C$_2$haloalkyl, C$_1$–C$_2$haloalkoxy, C$_1$–C$_4$alkoxycarbonyl, mono- and di-(C$_1$–C$_4$alkyl)amino, phenyl and pyridyl;

R$_4$ is hydrogen or C$_1$–C$_4$alkyl;

R$_5$ is C$_1$–C$_6$ alkyl, C$_2$–C$_6$ alkenyl, C$_1$–C$_4$ alkoxy, or mono- or di-C$_1$ –C$_4$–alkylamino, each of which is substituted with from 0 to 3 substituents independently selected from halogen, hydroxy, C$_1$–C$_2$alkoxy, C$_3$–C$_8$cycloalkyl, phenyl and phenylC$_1$–C$_2$alkoxy;

R$_6$ and R$_7$ are independently hydrogen, methyl, ethyl or halogen;

R$_8$ represents 0 or 1 substituent selected from halogen, C$_1$–C$_2$alkyl and C$_1$–C$_2$alkoxy; and/or Ar represents phenyl, 2-pyridyl, 1,3-thiazol-2-yl, 2-thienyl or 3-pyridazinyl, each of which is substituted with from 0 to 3 substituents independently selected from fluoro, hydroxy, C$_1$–C$_2$alkyl, C$_1$–C$_2$haloalkyl, cyano and C$_1$–C$_2$alkoxy.

Certain compounds of Formula I further satisfy Formula V, in which $Z_1$ and $Z_2$ are nitrogen, and $Z_3$ is $CR_3$:

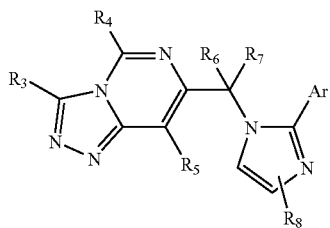

Formula V

In certain such, compounds, $R_3$ is hydrogen, cyano, $C_1$–$C_6$alkyl, $C_1$–$C_6$hydroxyalkyl, $C_3$–$C_7$cycloalkyl, $C_2$–$C_6$alkylether, $C_1$–$C_6$haloalkyl, $C_1$–$C_6$alkanoyl, pyridyl or carboxamido.

In other such compounds:

$R_3$ is selected from hydrogen, hydroxy, halogen, cyano, carboxamido, $C_1$–$C_6$alkyl, $C_1$–$C_6$alkoxy, $C_3$–$C_7$cycloalkyl, $C_2$–$C_6$alkyl ether, $C_1$–$C_4$hydroxyalkyl, $C_1$–$C_2$haloalkyl, $C_1$–$C_2$haloalkoxy, $C_1$–$C_4$alkoxycarbonyl, mono- and di-($C_1$–$C_4$alkyl)amino, phenyl and pyridyl;

$R_4$ is hydrogen or $C_1$–$C_4$alkyl;

$R_5$ is $C_1$–$C_6$ alkyl, $C_2$–$C_6$ alkenyl, $C_1$–$C_4$ alkoxy, or mono- or di-$C_1$–$C_4$alkylamino, each of which is substituted with from 0 to 3 substituents independently selected from halogen, hydroxy, $C_1$–$C_2$alkoxy, $C_3$–$C_8$cycloalkyl, phenyl and phenyl$C_1$–$C_2$alkoxy;

$R_6$ and $R_7$ are independently hydrogen, methyl, ethyl or halogen;

$R_8$ represents 0 or 1 substituent selected from halogen, $C_1$–$C_2$alkyl and $C_1$–$C_2$alkoxy; and/or Ar represents phenyl, 2-pyridyl, 1,3-thiazol-2-yl, 2-thienyl or 3-pyridazinyl, each of which is substituted with from 0 to 3 substituents independently selected from fluoro, hydroxy, $C_1$–$C_2$alkyl, $C_1$–$C_2$haloalkyl, cyano and $C_1$–$C_2$alkoxy.

Compounds provided herein detectably alter (modulate) ligand binding to $GABA_A$ receptor, as determined using a standard in vitro receptor binding assay. References herein to a "$GABA_A$ receptor ligand binding assay" are intended to refer to the standard in vitro receptor binding assay provided in Example 6. Briefly, a competition assay may be performed in which a $GABA_A$ receptor preparation is incubated with labeled (e.g., $^3$H) ligand, such as Flumazenil, and unlabeled test compound. Incubation with a compound that detectably modulates ligand binding to $GABA_A$ receptor will result in a decrease or increase in the amount of label bound to the $GABA_A$ receptor preparation, relative to the amount of label bound in the absence of the compound. Preferably, such a compound will exhibit a $K_i$ at $GABA_A$ receptor of less than 1 micromolar, more preferably less than 500 nM, 100 nM, 20 nM or 10 nM. The $GABA_A$ receptor used to determine in vitro binding may be obtained from a variety of sources, for example from preparations of rat cortex or from cells expressing cloned human $GABA_A$ receptors.

In certain embodiments, preferred compounds have favorable pharmacological properties, including oral bioavailability (such that a sub-lethal or preferably a pharmaceutically acceptable oral dose, preferably less than 2 grams, more preferably less than or equal to one gram or 200 mg, can provide a detectable in vivo effect), low toxicity (a preferred compound is nontoxic when a therapeutically effective amount is administered to a subject), minimal side effects (a preferred compound produces side effects comparable to placebo when a therapeutically effective amount of the compound is administered to a subject), low serum protein binding, and a suitable in vitro and in vivo half-life (a preferred compound exhibits an in vivo half-life allowing for Q.I.D. dosing, preferably T.I.D. dosing, more preferably B.I.D. dosing and most preferably once-a-day dosing). Distribution in the body to sites of complement activity is also desirable (e.g., compounds used to treat CNS disorders will preferably penetrate the blood brain barrier, while low brain levels of compounds used to treat periphereal disorders are typically preferred).

Routine assays that are well known in the art may be used to assess these properties and identify superior compounds for a particular use. For example, assays used to predict bioavailability include-transport across human intestinal cell monolayers, such as Caco-2 cell monolayers. Penetration of the blood brain barrier of a compound in humans may be predicted from the brain levels of the compound in laboratory animals given the compound (e.g., intravenously). Serum protein binding may be predicted from albumin binding assays, such as those described by Oravcová, et al. (1996) *Journal of Chromatography* B 677:1-27. Compound half-life is inversely proportional to the required frequency of dosage. In vitro half-lives of compounds may be predicted from assays of microsomal half-life as described by Kuhnz and Gieschen (1998) *Drug Metabolism and Disposition* 26:1120–27.

As noted above, preferred compounds provided herein are nontoxic. In general, the term "nontoxic" as used herein shall be understood in a relative sense and is intended to refer to any substance that has been approved by the United States Food and Drug Administration ("FDA") for administration to mammals (preferably humans) or, in keeping with established criteria, is susceptible to approval by the FDA for administration to mammals (preferably humans). In addition, a highly preferred nontoxic compound generally satisfies one or more of the following criteria when administered at a minimum therapeutically effective amount or when contacted with cells at a concentration that is sufficient to inhibit the binding of $GABA_A$ receptor ligand to $GABA_A$ receptor in vitro: (1) does not substantially inhibit cellular ATP production; (2) does not significantly prolong heart QT intervals; (3) does not cause substantial liver enlargement or (4) does not cause substantial release of liver enzymes.

As used herein, a compound that does not substantially inhibit cellular ATP production is a compound that, when tested as described in Example 8, does not decrease cellular ATP levels by more than 50%. Preferably, cells treated as described in Example 8 exhibit ATP levels that are at least 80% of the ATP levels detected in untreated cells. Highly preferred compounds are those that do not substantially inhibit cellular ATP production when the concentration of compound is at least 10-fold, 100-fold or 1000-fold greater than the $EC_{50}$ or $IC_{50}$ for the compound.

A compound that does not significantly prolong heart QT intervals is a compound that does not result in a statistically significant prolongation of heart QT intervals (as determined by electrocardiography) in guinea pigs, minipigs or dogs upon administration of a dose that yields a serum concentration equal to the $EC_{50}$ or $IC_{50}$ for the compound. In certain preferred embodiments, a dose of 0.01, 0.05. 0.1, 0.5, 1, 5, 10, 40 or 50 mg/kg administered parenterally or orally does not result in a statistically significant prolongation of heart QT intervals. By "statistically significant" is meant results varying from control at the p<0.1 level or more preferably at the p<0.05 level of significance as measured using a standard parametric assay of statistical significance such as a student's T test.

A compound does not cause substantial liver enlargement if daily treatment of laboratory rodents (e.g., mice or rats) for 5–10 days with a dose that yields a serum concentration equal to the $EC_{50}$ or $IC_{50}$ for the compound results in an increase in liver to body weight ratio that is no more than 100% over matched controls. In more highly preferred embodiments, such doses do not cause liver enlargement of more than 75% or 50% over matched controls. If non-rodent mammals (e.g., dogs) are used, such doses should not result in an increase of liver to body weight ratio of more than 50%, preferably not more than 25%, and more preferably not more than 10% over matched untreated controls. Preferred doses within such assays include 0.01, 0.05. 0.1, 0.5, 1, 5, 10, 40 or 50 mg/kg administered parenterally or orally.

Similarly, a compound does not promote substantial release of liver enzymes if administration of a dose that yields a serum concentration equal to the $EC_{50}$ or $IC_{50}$ for the compound does not elevate serum levels of ALT, LDH or AST in laboratory rodents by more than 3-fold (preferably no more than 2-fold) over matched mock-treated controls. In more highly preferred embodiments, such doses do not elevate, such serum levels by more than 75% or 50% over matched controls. Alternately, a compound does not promote substantial release of liver enzymes if, in an in vitro hepatocyte assay, concentrations (in culture media or other such solutions that are contacted and incubated with hepatocytes in vitro) concentrations that are equal to the $EC_{50}$ or $IC_{50}$ for the compound do not cause detectable release of any of such liver enzymes into culture medium above baseline levels seen in media from matched mock-treated control cells. In more highly preferred embodiments, there is no detectable release of any of such liver enzymes into culture medium above baseline levels when such compound concentrations are two-fold, five-fold, and preferably ten-fold the $EC_{50}$ or $IC_{50}$ for the compound.

In other embodiments, certain preferred compounds do not inhibit or induce microsomal cytochrome P450 enzyme activities, such as CYP1A2 activity, CYP2A6 activity, CYP2C9 activity, CYP2C19 activity, CYP2D6 activity, CYP2E1 activity or CYP3A4 activity at a concentration equal to the $EC_{50}$ or $IC_{50}$ for the compound.

Certain preferred compounds are not clastogenic or mutagenic (e.g., as determined using standard assays such as the Chinese hamster ovary cell vitro micronucleus assay, the mouse lymphoma assay, the human lymphocyte chromosomal aberration assay, the rodent bone marrow micronucleus assay, the Ames test or the like) at a concentration equal to the $EC_{50}$ or $IC_{50}$ for the compound. In other embodiments, certain preferred compounds do not induce sister chromatid exchange. (e.g., in Chinese hamster ovary cells) at such concentrations.

For detection purposes, as discussed in more detail below, compounds provided herein may be isotopically-labeled or radiolabeled. Such compounds are identical to those described above, but for the fact that one or more atoms are replaced by an atom having an atomic mass or mass number different from the atomic mass or mass number usually found in nature. Examples of isotopes that can be incorporated into compounds provided herein include isotopes of hydrogen, carbon, nitrogen, oxygen, phosphorous, fluorine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$ and $^{36}Cl$. In addition, substitution with heavy isotopes such as deuterium (i.e., $^2H$) can afford certain therapeutic advantages resulting from greater metabolic stability, such as increased in vivo half-life or reduced dosage requirements and, hence, may be preferred in some circumstances.

As noted above, different stereoisomeric forms, such as racemates and optically active forms, are encompassed by the present invention. In certain embodiments, it may be desirable to obtain single enantiomers (i.e., optically active forms). Standard methods for preparing single enantiomers include asymmetric synthesis and resolution of the racemates. Resolution of the racemates can be accomplished by conventional methods such as crystallization in the presence of a resolving agent, or chromatography using, for example, a chiral HPLC column.

Pharmaceutical Compositions

The present invention also provides pharmaceutical compositions comprising at least one compound provided herein, together with at least one physiologically acceptable carrier or excipient. Such compounds may be used for treating patients in which $GABA_A$ receptor modulation is desirable (e.g., patients undergoing painful procedures who would benefit from the induction of amnesia, or those suffering from anxiety, depression, sleep disorders or cognitive impairment). Pharmaceutical compositions may comprise, for example, water, buffers (e.g., neutral buffered saline or phosphate buffered saline), ethanol, mineral oil, vegetable oil, dimethylsulfoxide, carbohydrates (e.g., glucose, mannose, sucrose or dextrans), mannitol, proteins, adjuvants, polypeptides or amino acids such as glycine, antioxidants, chelating agents such as EDTA or glutathione and/or preservatives. Preferred pharmaceutical compositions are formulated for oral delivery to humans or other animals (e.g., companion animals such as dogs or cats). If desired, other active ingredients may also be included, such as additional CNS-active agents.

Pharmaceutical compositions may be formulated for any appropriate manner of administration, including, for example, topical, oral, nasal, rectal or parenteral administration. The term parenteral as used herein includes subcutaneous, intradermal, intravascular (e.g., intravenous), intramuscular, spinal, intracranial, intrathecal and intraperitoneal injection, as well as any similar injection or infusion technique. In certain embodiments, compositions in a form suitable for oral use are preferred. Such forms include, for example, tablets, troches, lozenges, aqueous or oily suspensions, dispersible powders or granules, emulsion, hard or soft capsules, or syrups or elixirs. Within yet other embodiments, compositions of the present invention may be formulated as a lyophilizate.

Compositions intended for oral use may further comprise one or more components such as sweetening agents, flavoring agents, coloring agents and preserving agents in order to provide appealing and palatable preparations. Tablets contain the active ingredient in admixture with physiologically acceptable excipients that are suitable for the manufacture of tablets. Such excipients include, for example, inert diluents (e.g., calcium carbonate, sodium carbonate, lactose, calcium phosphate or sodium phosphate), granulating and disintegrating agents (e.g., corn starch or alginic acid), binding agents (e.g., starch, gelatin or acacia) and lubricating agents (e.g., magnesium stearate, stearic acid or talc). The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent (e.g., calcium carbonate, calcium phosphate or kaolin), or as soft gelatin capsules wherein the active ingredient is mixed with water or an oil medium (e.g., peanut oil, liquid paraffin or olive oil).

Aqueous suspensions comprise the active materials in admixture with one or more excipients suitable for the manufacture of aqueous suspensions. Such excipients include suspending agents (e.g., sodium carboxymethylcellulose, methylcellulose, hydropropylmethylcellulose, sodium alginate, polyvinylpyrrolidone, gum tragacanth and gum acacia); and dispersing or wetting agents (e.g., naturally-occurring phosphatides such as lecithin, condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol monooleate, or condensation products of ethylene oxide with partial esters derived from fatty acids and hexitol anhydrides such as polyethylene sorbitan monooleate). Aqueous suspensions may also contain one or more preservatives, for example ethyl, or n-propyl p-hydroxybenzoate, one or more coloring agents, one or more flavoring agents and/or one or more sweetening agents, such as sucrose or saccharin.

Oily suspensions may be formulated by suspending the active ingredients in a vegetable oil (e.g., arachis oil, olive oil, sesame oil or coconut oil) or in a mineral oil such as liquid paraffin. The oily suspensions may contain a thickening agent such as beeswax, hard paraffin or cetyl alcohol. One or more sweetening agents and/or flavoring agents may be added to provide palatable oral preparations. Such suspension may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, such as sweetening, flavoring and coloring agents, may also be present.

Pharmaceutical compositions may also be in the form of oil-in-water emulsions. The oily phase may be a vegetable oil (e.g., olive oil or arachis oil) or a mineral oil (e.g., liquid paraffin) or mixtures thereof. Suitable emulsifying agents may be naturally-occurring gums (e.g., gum acacia or gum tragacanth), naturally-occurring phosphatides (e.g., soy bean, lecithin, and esters or partial esters derived from fatty acids and hexitol), anhydrides (e.g., sorbitan monoleate) and condensation products of partial esters derived from fatty acids and hexitol with ethylene oxide (e.g:, polyoxyethylene sorbitan monoleate). The emulsions may also contain sweetening and/or flavoring agents.

Syrups and elixirs may be formulated with sweetening agents, such as glycerol, propylene glycol, sorbitol or sucrose. Such formulations may also comprise one or more demulcents, preservatives, flavoring agents and/or coloring agents.

A pharmaceutical composition may be prepared as a sterile injectable aqueous or oleaginous suspension. The compound, depending on the vehicle and concentration used, can either be suspended or dissolved in the vehicle. Such a composition may be formulated according to the known art using suitable dispersing, wetting agents and/or suspending agents such as those mentioned above. Among the acceptable vehicles and solvents that may be employed are water, 1,3-butanediol, Ringer's solution and isotonic sodium chloride solution. In addition, sterile, fixed oils may be employed as a solvent or suspending medium. For this purpose any bland fixed oil may be employed, including synthetic mono- or diglycerides. In addition, fatty acids such as oleic acid find use in the preparation of injectible compositions, and adjuvants such as local anesthetics, preservatives and/or buffering agents can be dissolved in the vehicle.

Pharmaceutical compositions may also be prepared in the form of suppositories (e.g., for rectal administration). Such compositions can be prepared by mixing the drug with a suitable non-irritating excipient that is solid at ordinary temperatures but liquid at the rectal temperature and will therefore melt in the rectum to release the drug. Suitable excipients include, for example, cocoa butter and polyethylene glycols.

For administration to non-human animals, the composition may also be added to animal feed or drinking water. It may be convenient to formulate animal feed and drinking water compositions so that the animal takes in an appropriate quantity of the composition along with its diet. It may also be convenient to present the composition as a premix for addition to feed or drinking water.

Pharmaceutical compositions may be formulated as sustained release formulations (i.e., a formulation such as a capsule that effects a slow release of compound following administration). Such formulations may generally be prepared using well known technology and administered by, for example, oral, rectal or subcutaneous implantation, or by implantation at the desired target site. Carriers for use within such formulations are biocompatible, and may also be biodegradable; preferably the formulation provides a relatively constant level of active compound release. The amount of compound contained within a sustained release formulation depends upon the site of implantation, the rate and expected duration of release and the nature of the condition to be treated or prevented.

Compounds provided herein are generally present within a pharmaceutical composition in a therapeutically effective amount, as described above. Compositions providing dosage levels ranging from about 0.1 mg to about 140 mg per kilogram of body weight per day are preferred (about 0.5 mg to about 7 g per human patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient. It will be understood, however, that the optimal dose for any particular patient will depend upon a variety of factors, including the activity of the specific compound employed; the age, body weight, general health, sex and diet of the patient; the time and route of administration; the rate of excretion; any simultaneous treatment, such as a drug combination; and the type and severity of the particular disease undergoing treatment. Optimal dosages may be established using routine testing and procedures that are well known in the art.

Pharmaceutical compositions may be packaged for treating a CNS disorder such as anxiety, depression, a sleep disorder, attention deficit disorder or a cognitive disorder such as short-term memory loss or Alzheimer's dementia.

Packaged pharmaceutical preparations include a container holding a therapeutically effective amount of at least one compound as described herein and instructions (e.g., labeling) indicating that the contained composition is to be used for treating the CNS disorder.

Methods of Use

Within certain aspects, the present invention provides methods for inhibiting the development of a CNS disorder. In other words, therapeutic methods provided herein may be used to treat an existing disorder, or may be used to prevent, decrease the severity of, or delay the onset of such a disorder in a patient who is free of detectable CNS disorder. CNS disorders are discussed in more detail below, and may be diagnosed and monitored using criteria that have been established in the art. Alternatively, or in addition, compounds provided herein may be administered to a patient to improve short-term memory or induce sleep in a healthy patient. Patients include humans, domesticated companion animals (pets, such as dogs) and livestock animals, with dosages and treatment regimes as described above.

Frequency of dosage may vary, depending on the compound used and the particular disease to be treated or prevented. In general, for treatment of most disorders, a dosage regimen of 4 times daily or less is preferred. For soporific treatment, a single dose that rapidly reaches a concentration in cerebrospinal fluid that is sufficient to inhibit the binding of $GABA_A$ receptor ligand to $GABA_A$ receptor in vitro is desirable. Patients may generally be monitored for therapeutic effectiveness using assays suitable for the condition being treated or prevented, which will be familiar to those of ordinary skill in the art.

Within preferred embodiments, compounds provided herein are used to treat patients in need of such treatment. In general, such patients are treated with a therapeutically effective amount of a compound of Formula I (or a pharmaceutically acceptable salt thereof); preferably the amount is sufficient to alter one or more symptoms of a CNS disorder. Compounds that act as agonists at $\alpha_2\beta_3\gamma_2$ and $\alpha_3\beta_3\gamma_2$ receptor subtypes are particularly useful in treating anxiety disorders such as panic disorder, obsessive compulsive disorder and generalized anxiety disorder; stress disorders including post-traumatic stress and acute stress disorders. Compounds that act as agonists at $\alpha_2\beta_3\gamma_2$ and $\alpha_3\beta_3\gamma_2$ receptor subtypes are also useful in treating depressive or bipolar disorders, schizophrenia and sleep disorders, and may be used in the treatment of age-related cognitive decline and Alzheimer's disease. Compounds that act as inverse agonists at the $\alpha_5\beta_3\gamma_2$ receptor subtype or $\alpha_1\beta_2\gamma_2$ and $\alpha_5\beta_3\gamma_2$ receptor subtypes are particularly useful in treating cognitive disorders including those resulting from Down's Syndrome, neurodegenerative diseases such as Alzheimer's disease, Parkinson's disease and stroke related dementia. Compounds that act as inverse agonists at the $\alpha_5\beta_3\gamma_2$ receptor subtype are particularly useful in treating cognitive disorders through the enhancement of memory, particularly short-term memory, in memory-impaired patients; while those that act as agonists at the $\alpha_5\beta_3\gamma_2$ receptor subtype are particularly useful for the induction of amnesia. Compounds that act as agonists at the $\alpha_1\beta_3\gamma_2$ receptor subtype are useful in treating sleep disorders and convulsive disorders such as epilepsy. Compounds that act as antagonists at the benzodiazepine site are useful in reversing the effect of benzodiazepine overdose and in treating drug and alcohol addiction.

CNS disorders that can be treated using compounds and compositions provided herein include:

Depression, e.g., major depression, dysthymic disorder, atypical depression, bipolar disorder, depressed phase of bipolar disorder.

Anxiety, e.g., general anxiety disorder (GAD), agoraphobia, panic disorder +/− agoraphobia, social phobia, specific phobia, Post traumatic stress disorder, obsessive compulsive disorder (OCD), dysthymia, adjustment disorders with disturbance of mood and anxiety, separation anxiety disorder, anticipatory anxiety acute stress disorder, adjustment disorders, cyclothymia.

Sleep disorders, e.g., primary insomnia, circadian rhythm sleep disorder, dyssomnia NOS, parasomnias, including nightmare disorder, sleep terror disorder, sleep disorders secondary to depression and/or anxiety or other mental disorders, and substance induced sleep disorder. Representative treatable symptoms of sleep disorders include, for example, difficulty falling asleep, excessive waking during the night, waking too early and waking feeling unrefreshed.

Cognition Impairment, e.g., Alzheimer's disease, Parkinson's disease, mild cognitive impairment (MCI), age-related cognitive decline (ARCD), stroke, traumatic brain injury, AIDS associated dementia, and dementia associated with depression, anxiety and psychosis (including schizophrenia and hallucinatory disorders).

Attention Deficit Disorders, e.g., attention deficit disorder (ADD) and attention deficit and hyperactivity disorder (ADHD).

Speech disorders, e.g., motor tic, clonic stuttering, dysfluency, speech blockage, dysarthria, Tourette's Syndrome and logospasm.

Compounds and compositions provided herein can also be used to improve short-term memory (working memory) in a patient. A preferred therapeutically effective amount of a compound for improving short-term memory loss is an amount sufficient to result in a statistically significant improvement in any standard test of short-term memory function, including forward digit span and serial rote learning. For example, such a test may be designed to evaluate the ability of a patient to recall words or letters. Alternatively, a more complete neurophysical evaluation may be used to assess short-term memory function. Patients treated in order to improve short-term memory may, but need not, have been diagnosed with memory impairment or be considered predisposed to development of such impairment.

In a separate aspect, the present invention provides methods for potentiating the action (or therapeutic effect) of other CNS agent(s). Such methods comprise administering a therapeutically effective amount of a compound provided herein in combination with a therapeutically effective amount of another CNS agent. Such other CNS agents include, but are not limited to the following: for anxiety, serotonin receptor (e.g., 5-$HT_{1A}$) agonists and antagonists; for anxiety and depression, neurokinin receptor antagonists or corticotropin releasing factor receptor ($CRF_1$) antagonists; for sleep disorders, melatonin receptor agonists; and for neurodegenerative disorders, such as Alzheimer's dementia, nicotinic agonists, muscarinic agents, acetylcholinesterase inhibitors and dopamine receptor agonists. Within certain embodiments, the present invention provides a method of potentiating the antidepressant activity of selective serotonin reuptake inhibitors (SSRIs) by co-administering a therapeutically effective amount of a $GABA_A$ agonist compound provided herein in combination with an SSRI. A therapeutically effective amount of compound, when co-administered with another CNS agent, is an amount sufficient to result in a detectable change in patient symptoms, when compared to a patient treated with the other CNS agent alone.

The present invention also pertains to methods of inhibiting the binding of benzodiazepine compounds (i.e., compounds that comprise the benzodiazepine ring structure), such as RO15-1788 or GABA, to $GABA_A$ receptor. Such methods involve contacting cells expressing $GABA_A$ receptor with a concentration of compound provided herein that is sufficient to inhibit the binding of $GABA_A$ receptor ligand to $GABA_A$ receptor in vitro, as determined using the assay described in Example 6. This method includes, but is not limited to, inhibiting the binding of benzodiazepine compounds to $GABA_A$ receptors in vivo (e.g., in a patient given an amount of a $GABA_A$ receptor modulator provided herein that results in a concentration of compound in cerebrospinal fluid that is sufficient to inhibit the binding of benzodiazepine compounds or GABA to $GABA_A$ receptor in vitro). In one embodiment, such methods are useful in treating benzodizepine drug overdose. The amount of $GABA_A$ receptor modulator that is sufficient to inhibit the binding of a benzodiazepine compound to $GABA_A$ receptor may be readily determined via a $GABA_A$ receptor binding assay as described in Example 6.

Within separate aspects, the present invention provides a variety of in vitro uses for the $GABA_A$ receptor modulators provided herein. For example, such compounds may be used as probes for the detection and localization of $GABA_A$ receptors, in samples such as tissue sections, as positive controls in assays for receptor activity, as standards and reagents for determining the ability of a candidate agent to bind to $GABA_A$ receptor, or as radiotracers for positron emission tomography (PET) imaging or for single photon emission computerized tomography (SPECT). Such assays can be used to characterize $GABA_A$ receptors in living subjects. Such compounds are also useful as standards and reagents in determining the ability of a potential pharmaceutical to bind to $GABA_A$ receptor.

Within methods for determining the presence or absence of $GABA_A$ receptor in a sample, a sample may be incubated with a compound as provided herein under conditions that permit binding of the compound to $GABA_A$ receptor. The amount of compound bound to $GABA_A$ receptor in the sample is then detected. For example, the compound may be labeled using any of a variety of well known techniques (e.g., radiolabeled with a radionuclide such as tritium, as described herein), and incubated with the sample (which may be, for example, a preparation of cultured cells, a tissue preparation or a fraction thereof). A suitable incubation time may generally be determined by assaying the level of binding that occurs over a period of time. Following incubation, unbound compound is removed, and bound compound detected using any method suitable for the label employed (e.g., autoradiography or scintillation counting for radiolabeled compounds; spectroscopic methods may be used to detect luminescent groups and fluorescent groups). As a control, a matched sample may be simultaneously contacted with radiolabeled compound and a greater amount of unlabeled compound. Unbound labeled and unlabeled compound is then removed in the same fashion, and bound label is detected. A greater amount of detectable label in the test sample than in the control indicates the presence of $GABA_A$ receptor in the sample. Detection assays, including receptor autoradiography (receptor mapping) of $GABA_A$ receptors in cultured cells or tissue samples may be performed as described by Kuhar in sections 8.1.1 to 8.1.9 of Current Protocols in Pharmacology (1998) John Wiley & Sons, New York.

For example, compounds provided herein may be used for detecting $GABA_A$ receptors in cell or tissue samples. This may be done using matched cell or tissue samples that have not previously been contacted with a $GABA_A$ receptor modulator, at least one of which is prepared as an experimental sample and at least one of which is prepared as a control sample. An experimental sample is prepared by contacting (under conditions that permit binding of RO15-1788 to $GABA_A$ receptors within cell and tissue samples) a sample with a detectably-labeled compound of Formula I. A control sample is prepared in the same manner as the experimental sample, except that it is also is contacted with unlabelled compound at a molar concentration that is greater than the concentration of labeled modulator.

The experimental and control samples are then washed to remove unbound detectably-labeled compound. The amount of remaining bound detectably-labeled compound is then measured and the amount of detectably-labeled compound in the experimental and control samples is compared. The detection of a greater amount of detectable label in the washed experimental sample(s) than in the washed control sample(s) demonstrates the presence of $GABA_A$ receptor in the experimental sample.

The detectably-labeled $GABA_A$ receptor modulator used in this procedure may be labeled with a radioactive label or a directly or indirectly luminescent label. When tissue sections are used in this procedure and the label is a radiolabel, the bound, labeled compound may be detected autoradiographically.

Compounds provided herein may also be used within a variety of well known cell culture and cell separation methods. For example, compounds may be linked to the interior surface of a tissue culture plate or other cell culture support, for use in immobilizing $GABA_A$ receptor-expressing cells for screens, assays and growth in culture. Such linkage may be performed by any suitable technique, such as the methods described above, as well as other standard techniques. Compounds may also be used to facilitate cell identification and sorting in vitro, permitting the selection of cells expressing a $GABA_A$ receptor. Preferably, the compound(s) for use in such methods are labeled as described herein. Within one preferred embodiment, a compound linked to a fluorescent marker, such as fluorescein, is contacted with the cells, which are then analyzed by fluorescence activated cell sorting (FACS).

Within other aspects, methods are provided for modulating binding of ligand to a $GABA_A$ receptor in vitro or in vivo, comprising contacting a $GABA_A$ receptor with a sufficient amount of a $GABA_A$ receptor modulator provided herein, under conditions suitable for binding of ligand to the receptor. The $GABA_A$ receptor may be present in solution, in a cultured or isolated cell preparation or within a patient. Preferably, the $GABA_A$ receptor is a present in the brain of a mammal. In general, the amount of compound contacted with the receptor should be sufficient to modulate ligand binding to $GABA_A$ receptor in vitro within, for example, a binding assay as described in Example 6.

Also provided herein are methods for altering the signal-transducing activity of cellular $GABA_A$ receptor (particularly the chloride ion conductance), by contacting $GABA_A$ receptor, either in vitro or in vivo, with a sufficient amount of a compound as described above, under conditions suitable for binding of Flumazenil to the receptor. The $GABA_A$ receptor may be present in solution, in a cultured or isolated cell or cell membrane preparation or within a patient, and the amount of compound may be an amount that would be sufficient to alter the signal-transducing activity of GABA$_A$ receptor in vitro. In certain embodiments, the amount or concentration of compound contacted with the receptor should be sufficient to modulate Flumazenil binding to GABA$_A$ receptor in vitro within, for example, a binding assay as described in Example 6. An effect on signal-transducing activity may be detected as an alteration in the electrophysiology of the cells, using standard techniques. The amount or concentration of a compound that is sufficient to alter the signal-transducing activity of GABA$_A$ receptors may be determined via a GABA$_A$ receptor signal transduction assay, such as the assay described in Example 7. The cells expressing the GABA receptors in vivo may be, but are not limited to, neuronal cells or brain cells. Such cells may be contacted with one or more compounds provided herein through contact with a body fluid containing the compound, for example through contact with cerebrospinal fluid. Alteration of the signal-transducing activity of GABA$_A$ receptors in cells in vitro may be determined from a detectable change in the electrophysiology of cells expressing GABA$_A$ receptors, when such cells are contacted with a compound of the invention in the presence of GABA.

Intracellular recording or patch-clamp recording may be used to quantitate changes in electrophysiology of cells. A reproducible change in behavior of an animal given a compound of the invention may also be taken to indicate that a change in the electrophysiology of the animal's cells expressing GABA$_A$ receptors has occurred.

Preparation of Compounds

Compounds provided herein may generally be prepared using standard synthetic methods. Starting materials are generally readily available from commercial sources, such as Sigma-Aldrich Corp. (St. Louis, Mo.), or may be prepared as described herein. Representative procedures suitable for the preparation of compounds of Formula I are outlined in the following Schemes, which are not to be construed as limiting the invention in scope or spirit to the specific reagents and conditions shown in them. Those having skill in the art will recognize that the reagents and conditions may be varied and additional steps employed to produce compounds encompassed by the present invention. In some cases, protection of reactive functionalities may be necessary to achieve the desired transformations. In general, such need for protecting groups, as well as the conditions necessary to attach and remove such groups, will be apparent to those skilled in the art of organic synthesis. Each variable in the following schemes refers to any group consistent with the description of the compounds provided herein.

Abbreviations used the following Schemes and the accompanying Examples are as follows:

Abbreviations Used
  Bu butyl
  Bu$_3$Sn tributyl tin
  CDCl$_3$ deuterated chloroform
  CNBr cyanogens bromide
  δchemical shift
  DCM dichloromethane
  DME ethylene glycol dimethyl ether
  DMF N,N-dimethylformamide
  DPPF 1,1'-bis(diphenylphosphino)ferrocene
  EtOAc ethyl acetate
  EtOH ethanol
  Eq. equivalent(s)
  HOAc acetic acid
  HPLC high pressure liquid chromatography
  $^1$H NMR proton nuclear magnetic resonance
  Hz hertz
  LC/MS liquid chromatography/mass spectrometry
  MeOH methanol
  MS mass spectrometry
  M+1 mass+1
  NaOEt sodium ethoxide
  NMP 1-methyl-2-pyrrolidinone
  n-BuLi n-butyl lithium
  Pd/C palladium on carbon catalyst.
  Pd(PPh$_3$)$_4$ tetrakis(triphenylphosphine) palladium (0)
  Pd(Ph$_3$P)$_2$Cl$_2$ dichlorobis(triphenylphosphine) palladium (II)
  Pd$_2$(dba)$_3$ tris(dibenzylidineacetone) dipalladium (0)
  Ph$_3$P (or PPh$_3$)triphenylphosphine
  Py pyridine
  PTLC preparative thin layer chromatography
  THF tetrahydrofuran
  TLC thin layer chromatography Reaction Schemes

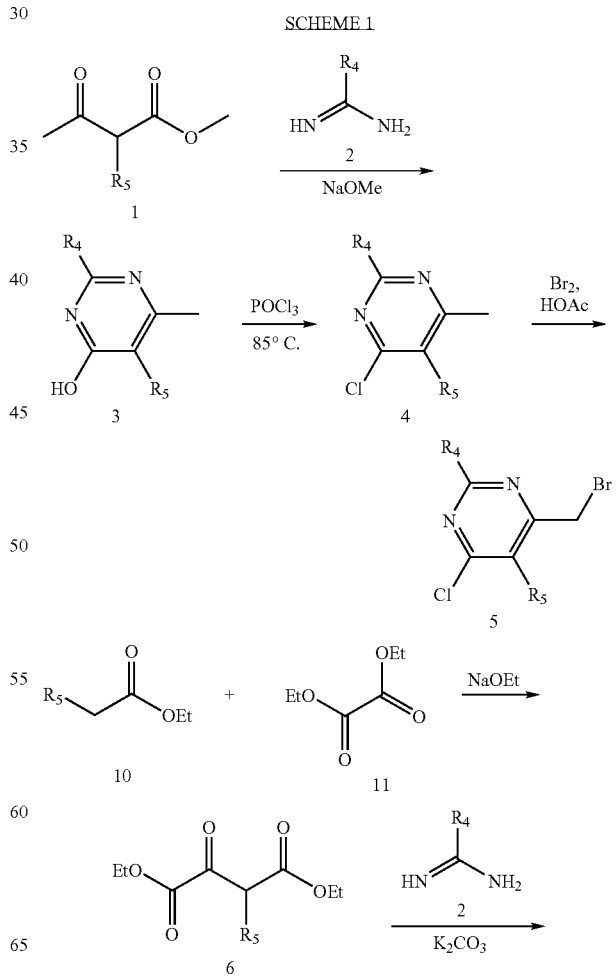

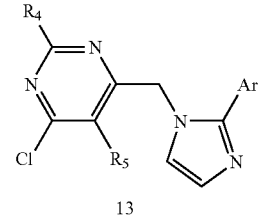

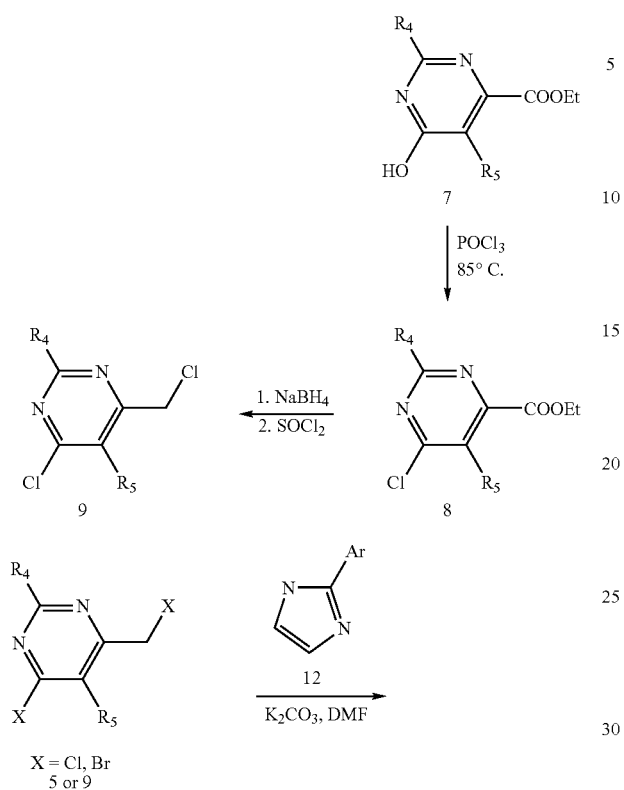

Intermediate 6-chloro pyrimidine compounds 13 are prepared from bromomethyl or chloromethyl compounds 5 and 9 as illustrated in Scheme 1. The condensation of ester 1 with amidine 2 is achieved by treatment with excess sodium methoxide in MeOH. Treatment of 3 with $POCl_3$ gives the chloro-pyrimidine 4, which can be converted to bromomethyl pyrimidine 5 by bromination with $Br_2$ in HOAc at 85° C. Similarly, the condensation of ethyl ester 10 and diethyl oxalate 11 is easily effected by treatment with sodium ethoxide in EtOH. The resulting diester 6 is reacted with the corresponding amidine 2 and excess $K_2CO_3$ in refluxing EtOH, to provide pyrimidinone 7. The transformation of 7 to the 6-chloro-pyrimidine ester 8 is effected by treatment with $POCl_3$ at 85° C. Compound 8 is then converted to chloromethyl pyrimidine 9 by $NaBH_4$ reduction followed by thionyl chloride treatment. The bromide 5 or chloride 9 is then reacted with imidazole 12 in DMF in the presence of excess $K_2CO_3$ to afford compound 13.

SCHEME 2

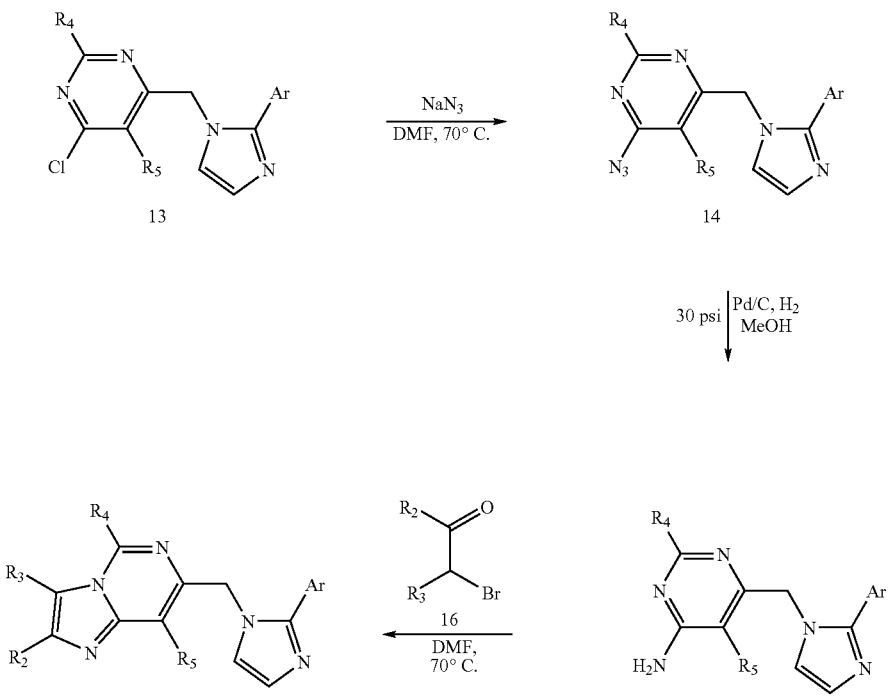

Scheme 2 illustrates the synthesis of compounds of formula 17 from compounds 13. Treatment of 13 with NaN₃ in DMF at 70° C. overnight provides the corresponding 4-azido-pyrimidine compound 14, which can be converted to the amino-pyrimidine 15 by hydrogenation. Finally, compound 15 reacts with various cc-bromo (chloro) aldehydes or ketones 16 in DMF to give the desired imidazole fused pyrimidine compound 17.

2 or 3–Cyano substituted compounds are prepared from the corresponding esters as illustrated in Scheme 3. Treatment of esters 18 or 19 (made according scheme 2) with excess ammonia in EtOH gives the amide 20 and 21, which can be converted into cyano compounds 22 and 23 by stirring with excess POCl₃ in pyridine.

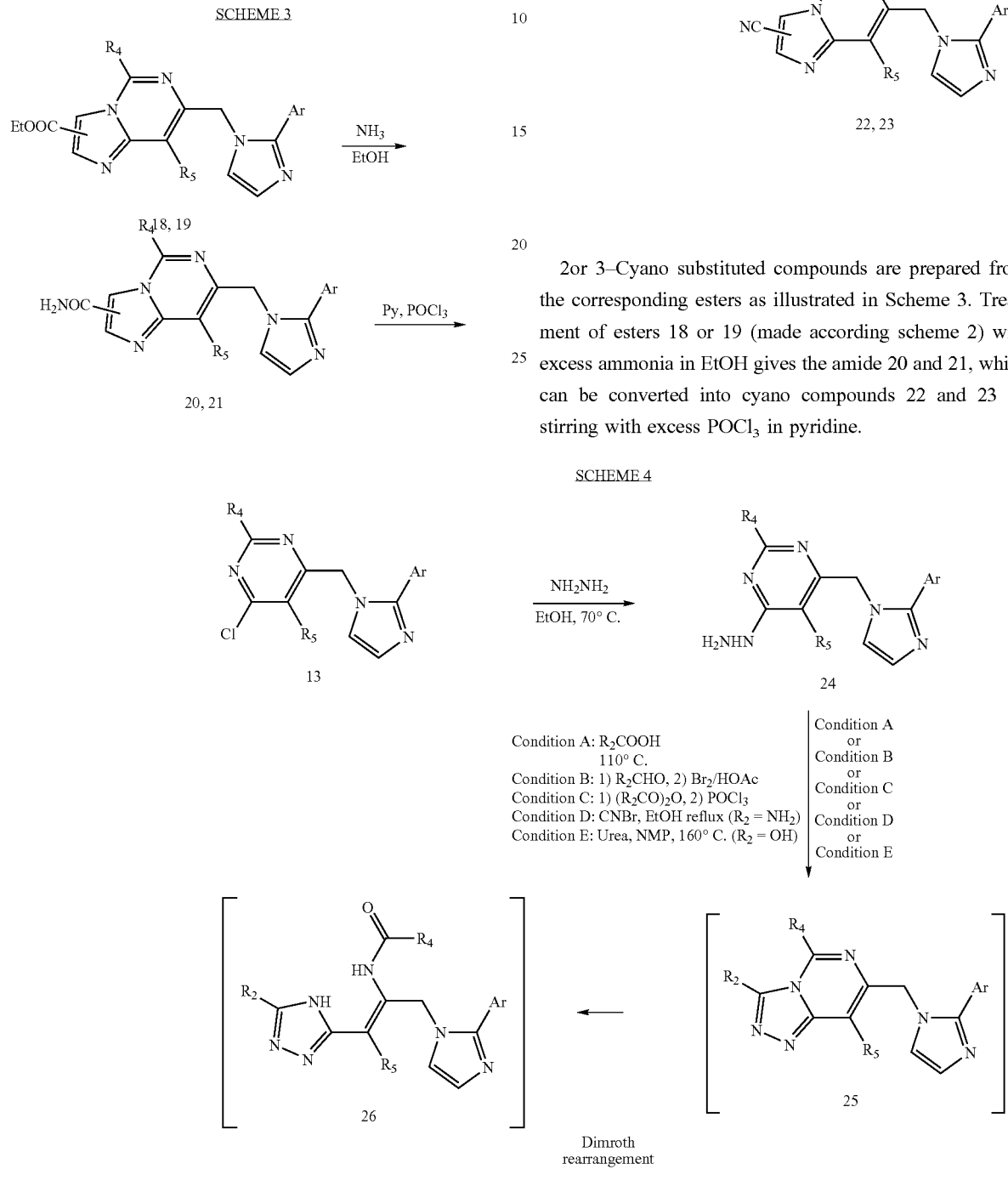

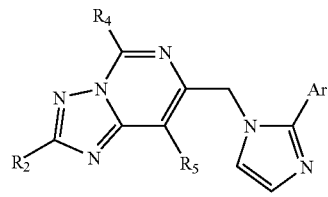

27

Scheme 4 illustrates the synthesis of [1,2,4]triazolo[1,5-c]pyrimidines 27. Treatment of compounds 13 with hydrazine gives intermediates 24. Conversion of compound 24 to compound 27 is achieved under conditions A-E via intermediates 25 (non-rearranged compound, 1,2,4-triazolo[4,3-c]pyrimidines) and 26 through Dimroth rearrangement. A variety of conditions may be used depending on the nature of $R_2$. In general, condition A is applied when $R_2$ is an unhindered aliphatic group; condition B is applied when $R_2$ is an aryl group; and condition C is applied when $R_2$ is a hindered aliphatic group. While condition D gives amino substituted [1,2,4]triazolo[1,5-c]pyrimidines (27, $R_2$=NH$_2$), hydroxyl substituted [1,2,4]triazolo[1,5-c]pyrimidines (27, $R_2$=OH) are obtained when condition E is applied. Under all of these conditions, the rearrangement reactions are essentially complete to give the rearranged products 27. The $R_2$ group in 27 can be further elaborated if necessary as demonstrated in the examples.

To synthesize the non-rearranged products, 1,2,4-triazolo[4,3-c]pyrimidines 25, milder conditions are used to effect the cyclization as illustrated by Scheme 5. Thus, compounds 25 are prepared from 24 via a variety of conditions (conditions A–C in Scheme 5) depending on the nature of the substitutions ($R_3$, $R_4$ and $R_5$) and starting material availability. In general, the hydrazines 24 are treated with an excess amount of the corresponding $R_3C(OR)_3$ or anhydride without solvent (Conditions A and C). The reaction temperature ranges from 50° C. to 100° C. depending on the nature of $R_3$, $R_4$ and $R_5$. In the case of $R_3$=H, cyclization is effected with diethoxymethyl acetate at room temperature for 5 to 10 minutes (Condition B). The varying conditions for the formation of differently substituted 1,2,4-triazolo[4,3-c]pyrimidines 25 are further illustrated in the following Examples.

Extended treatment of the hydrazines 24 with the cyclization reagents described in Scheme 5 may also produce 1,2,4-triazolo[1,5-c]pyrimidines 27 (via Dimroth rearrange-

SCHEME 5

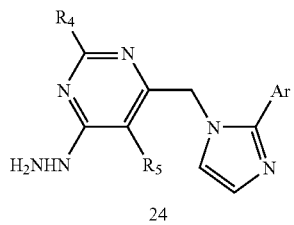

24

Condition A: $R_3C(OR)_3$
　　　　　　80° C. or 100° C.
Condition B: MeCOOCH(OEt)$_2$
　　　　　　rt, 5–10 min
Condition C: $(R_3CO)_2O$
　　　　　　50° C. or 100° C.

Condition A
or
Condition B
or
Condition C

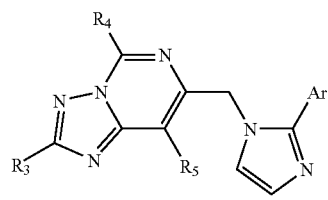

27

← Dimroth rearrangement

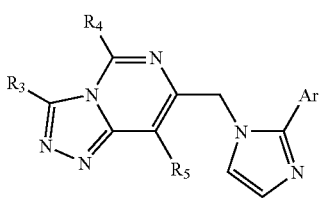

25 ment). Consistent with literature reports (Brown and Nagamatsu (1977) *Australian J. Chem.* 30:2515; and Brown and Nagamatsu (1978) *Australian J. Chem.* 31:2505 and references cited therein), the rearrangement of 1,2,4-triazolo[4,3-c]pyrimidines 25 to 1,2,4-triazolo[1,5-c]pyrimidines 27 is effected by a variety of conditions, including by treatment with acid or base, and even by extended treatment with $R_3C(OR)_3$. In addition, as illustrated by Scheme 4, other conditions effecting the rearrangement are (1) heating in a carboxylic acid; (2) treating the hydrazines 24 with an aldehyde, followed by reaction of bromine in acetic acid; (3) acylating the hydrazines 24 with an anhydride, followed by treatment with $POCl_3$; (4) heating the hydrazine 24 with cyanogen bromide; and (5) heating the hydrazine 24 with urea in NMP.

The isomeric products 1,2,4-triazolo[4,3-c]pyrimidines 25 and 1,2,4-triazolo[1,5-c]pyrimidines 27 are easily separable by PTLC or column chromatography. The 1,2,4-triazolo[4,3-c]pyrimidines 25 described herein are more polar than their corresponding isomers 27. All of 1,2,4-triazolo[4,3-c]pyrimidines 25 described herein are also readily distinguished from their isomers 27 by their $^1H$ NMR spectra. The structures of 1,2,4-triazolo[4,3-c]pyrimidines 25 described herein are further confirmed by converting them to their corresponding isomers 27 upon treatment with 0.1 N HCl at room temperature.

SCHEME 6

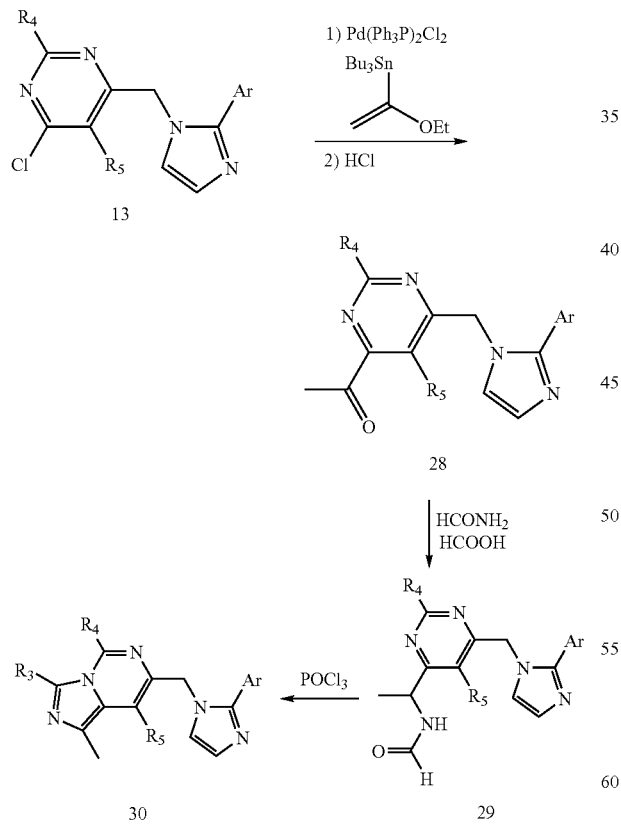

Scheme 6 illustrates the synthesis of imidazole fused pyrimidines 30. Intermediate 13 is coupled with tributyltinvinylethyl under $Pd(Ph_3P)_2Cl_2$ coupling conditions, followed by hydrolysis to give the ketone 28. Treatment of ketone 28 with formamide and formic acid, followed by $POCl_3$ affects cyclization to afford compound 30.

Compounds may be radiolabeled by carrying out their synthesis using precursors comprising at least one atom that is a radioisotope. Each radioisotope is preferably carbon (e.g., $^{14}C$), hydrogen (e.g. $^3H$), sulfur (e.g., $^{35}S$) or iodine (e.g., $^{125}I$). Tritium labeled compounds may also be prepared catalytically via platinum-catalyzed exchange in tritiated acetic acid, acid-catalyzed exchange in tritiated trifluoroacetic acid, or heterogeneous-catalyzed exchange with tritium gas using the compound as substrate. In addition, certain precursors may be subjected to tritium-halogen exchange with tritium gas, tritium gas reduction of unsaturated bonds, or reduction using sodium borotritide, as appropriate. Preparation of radiolabeled compounds may be conveniently performed by a radioisotope supplier specializing in custom synthesis of radiolabeled probe compounds.

The following Examples are offered by way of illustration and not by way of limitation. Unless otherwise specified, all reagents and solvents are of standard commercial grade and are used without further purification. Starting materials and intermediates described herein may generally be obtained from commercial sources, prepared from commercially available organic compounds or prepared using well known synthetic methods.

EXAMPLES

Starting materials and various intermediates described in the following Examples may be obtained from commercial sources, prepared from commercially available organic compounds, or prepared using known synthetic methods. Representative examples of methods suitable for preparing intermediates of the invention are also set forth below.

In the following Examples, LC-MS conditions for the characterization of the compounds herein are:

1. Analytical HPLC/MS instrumentation: Analyses are performed using a Waters 600 series pump (Waters Corporation, Milford, Mass.), a Waters 996 Diode Array Detector and a Gilson 215 auto-sampler (Gilson Inc, Middleton, Wis.), Micromass® LCT time-of-flight electrospray ionization mass analyzer. Data are acquired using MassLynx™ 4.0 software, with OpenLynx Global Server™, OpenLynx™ and AutoLynx™ processing.

2. Analytical HPLC conditions: 4.6×50 mm, Chromolith™ SpeedROD RP-18e column (Merck KGaA, Darmstadt, Germany); UV 10 spectra/sec, 220–340 nm summed; flow rate 6.0 mL/min; injection volume 1 µL;
    Gradient conditions—mobile phase A is 95% water, 5% MeOH with 0.05% TFA; mobile phase B is 95% MeOH, 5% water with 0.025% TFA, and the gradient is 0–0.5 minutes 10–100% B, hold at 100% B to 1.2 minutes, return to 10% B at 1.21 minutes inject-to-inject cycle time is 2.15 minutes.

3. Analytical MS conditions: capillary voltage 3.5 kV; cone voltage 30V; desolvation and source temperature are 350° C. and 120° C., respectively; mass range 181–750 with a scan time of 0.22 seconds and an inter scan delay of 0.05 minutes.

Example 1

Synthesis of Imidazo[1,2-c]Pyrimidines

A. 7-[2-(6-fluoro-pyridin-2-Yl)-imidazol-1-ylmethyl]-8-propyl-Imidazo[1,2-c]pyrimidine (106)

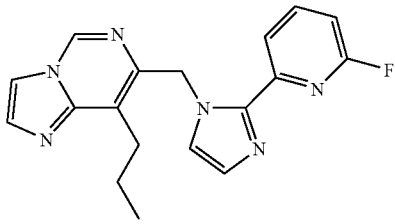

Step 1. Preparation of 5-propyl-6-methyl-pyrimidin-4-one (100)

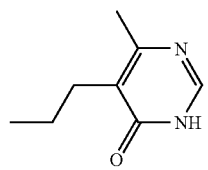

NaOMe (1.30 g, 24 mmol) is added to a stirred solution of formamidine (12 mmol) in MeOH (75 ml) at room temperature. The mixture is stirred for 15 minutes. 2-Acetylpentanoic acid methyl ester (10 mmol) is added and the mixture is stirred at room temperature overnight. Acetic acid (0.72 g, 12 mmol) is added and the solvent is removed in vacuo. Water (30 ml) is added to the residue and it is extracted with 2-butanone (3×30 ml). The combined extracts are washed with brine (40 ml), dried (Na$_2$SO$_4$) and evaporated, to provide a yellow solid (100), which is used in the next step without further purification.

Step 2. Preparation of 5-propyl-4-chloro-6-methyl-pyrimidine (101)

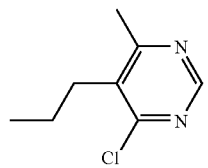

A mixture of 100 (10 mmol) and POCl$_3$ (25 ml) is heated at 85° C. for 4 hours. The solvent is removed in vacuo and EtOAc (30 ml) and water (30 ml) are added to the residue. NaHCO$_3$ is carefully added until the pH of aqueous layer is greater than 7. The layers are separated and the aqueous layer is extracted with EtOAc (2×30 ml). The combined extracts are washed with brine (50 mail), dried (Na$_2$SO$_4$) and evaporated. Flash column purification of the residue with 6:1 EtOAc:hexane provides the product. (101) as a light yellow oil.

Step 3. Preparation of 5-propyl-6-bromomethyl-4-chloro-pyrimidine (102)

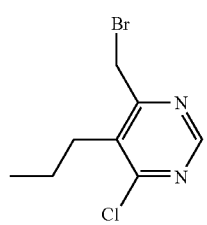

Br$_2$ (1.28 g, 8 mmol) is added dropwise to a stirred solution 101 in HOAc (20 ml) heated at 85° C. After addition, the mixture is stirred at 85° C. for 1 hour. The solvent is removed in vacuo and EtOAc (25 ml) and NaHCO$_3$ (25 ml) are added to the residue. The layers are separated and the organic layer is washed with Na$_2$S$_2$O$_3$ solution (sat. 15 ml) followed by brine (20 ml). The organic phase is dried (Na$_2$SO$_4$) and evaporated. The resulting yellow oil is purified by flash column (6:1 EtOAc, hexane) to afford the product (102) as a light yellow solid.

Step 4. Preparation of 6-chloro-4-[2-(6-fluoro-pyridin-2-yl)-imidazol-1-ylmethyl]-5-propyl-pyrimidine (103)

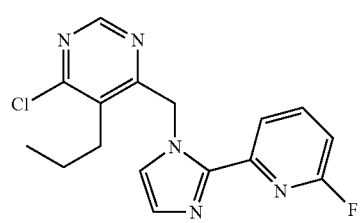

6-Fluoro-2-(1H-imidazol-2-yl)-pyridine is prepared as described in Example 16 of U.S. patent application Ser. No. 10/038,069, filed Dec. 12, 2001 and published as US 2003/0069257 on Apr. 10, 2003, which is hereby incorporated by reference at page 31 for its teaching regarding the synthesis of this compound. A mixture of 102 or 5-propyl-6-chloromethyl-4-chloro-pyrimidine (1 mmol of either), 6-fluoro-2-(1H-imidazol-2-yl)-pyridine (163 mg, 1 mmol) and K$_2$CO$_3$ (552 mg, 4 mmol) in DMF (6 ml) is stirred at room temperature overnight. The solvent is removed in vacuo and EtOAc (10 ml) and water (10 ml) are added to the residue. The layers are separated and the aqueous layer is extracted with EtOAc (10 ml). The combined extracts are washed with brine (10 ml), dried (Na$_2$SO$_4$) and evaporated. PTLC separation of the residue with 5% MeOH in CH$_2$Cl$_2$ provides the product (103) as a white solid.

Step 5. Preparation of 6-azido-4-[2-(6-fluoro-pyridin-2-yl)-imidazol-1-ylmethyl]-5-propyl-pyrimidine (104)

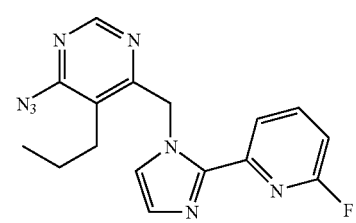

A solution of 103 (2.25 mmol) and NaN$_3$ (731 mg, 11.25 mmol) in DMF (15 ml) is heated at 70° C. in a sealed tube overnight. The solvent is removed in vacuo and water (10 ml) and EtOAc (10 ml) are added to the residue. The layers are separated and the aqueous layer is extracted with EtOAc (2×10 ml). The combined extracts are washed with brine (15 ml) and dried with $Na_2SO_4$. The solvent is removed in vacuo and the resulting yellow oil (104) is used in the next step without further purification.

Step 6. Preparation of 6-amino-4-[2-(6-fluoro-pyridin-2-yl)-imidazol-1-ylmethyl]-5-propyl-pyrimidine (105)

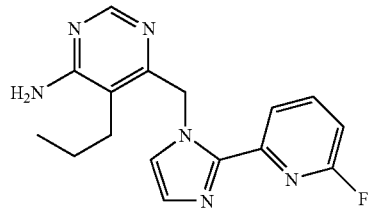

Pd/C (10%, 10 mg) is added to a solution of 104 (2 mmol) in MeOH (20 ml). The mixture is stirred under $H_2$ at 30 psi for 4 hours. The catalyst is removed by filtration and the filtrate is evaporated in vacuo. The light resulting yellow solid (105) is used in the next step without further purification.

Step 7. Preparation of 7-[2-(6-fluoro-pyridin-2-yl)-imidazol-1-ylmethyl]-8-propyl-imidazo[1,2-c]pyrimidine (106)

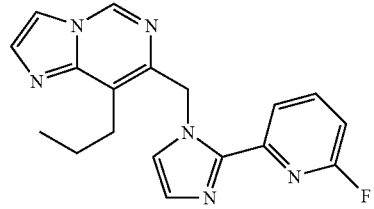

A solution of 105 (1.2 mmol) and chloroacetaldehyde (1 mL) in DMF (10 ml) is heated overnight at 70° C. in a sealed tube. The solvent is removed in vacuo and EtOAc (15 ml) and water (15 ml) are added to the residue. The layers are separated and the aqueous layer is extracted with EtOAc (15 ml). The combined extracts are washed with brine (15 ml), dried ($Na_2SO_4$) and evaporated. PTLC separation of the residue with 10% MeOH in $CH_2Cl_2$ provides the title compound as a white solid (106). $^1$H-NMR ($CDCl_3$) δ: 8.78 (s, 1H), 8.11 (dd, 1H), 7.83 (q, 1H), 7.65 (d, 1H), 7.56 (d, 1H), 7.18 (d, 1H), 7.15 (d, 1H), 6.83 (dd, 1H), 6.04 (s, 2H), 3.07–3.13 (m, 2H), 1.62–1.72 (m, 2H), 0.99 (t, 3H).

B. Synthesis of Additional Imidazo[1,2-c]pyrimidines

The compounds shown in Table 1 are synthesized via methods provided in Schemes 1 and 2 and further illustrated by Example 1A. All compounds in Table I exhibit a $K_i$ of less than 1 micromolar in the ligand binding assay of Example 6, as do compounds 106 (above) and 119, 127 and 129 (below).

TABLE 1

| | Compound | Name | LC-MS/NMR |
|---|---|---|---|
| 107. | | 7-[2-(6-Fluoro-pyridin-2-yl)-imidazol-1-ylmethyl]-2,3-dimethyl-8-propyl-imidazo[1,2-c]pyrimidine | LC-MS, M + 1 365.1; $^1$H-NMR ($CDCl_3$) δ: 8.52 (s, 1H), 8.10 (dd, 1H), 7.83 (q, 1H), 7.15 (s, 1H), 7.14 (s, 1H), 6.83 (dd, 1H), 6.03 (s, 2H), 3.04–3.08 (m, 2H), 2.41 (d, 6H), 1.64–1.70 (m, 2H), 0.96 (t, 3H). |
| 108. | | 2-Ethyl-7-[2-(6-fluoro-pyridin-2-yl)-imidazol-1-ylmethyl]-8-propyl-imidazo[1,2-c]pyrimidine | LC-MS, M + 1 365.2; $^1$H-NMR ($CDCl_3$) δ: 8.70 (s, 1H), 8.11 (dd, 1H), 7.83 (q, 1H), 7.31 (s, 1H), 7.26 (s, 1H), 7.15 (d, 1H), 6.83 (dd, 1H), 6.02 (s, 2H), 3.04–3.09 (m, 2H), 2.83 (q, 2H), 1.64–1.72 (m, 2H), 1.32 (t, 3H), 0.97 (t, 3H). |

TABLE 1-continued

| | Compound | Name | LC-MS/NMR |
|---|---|---|---|
| 109. | | 7-[2-(6-Fluoro-pyridin-2-yl)-imidazol-1-ylmethyl]-8-propyl-imidazo[1,2-c]pyrimidine-3-carboxylic acid ethyl ester | LC-MS, M + 1 409.2; $^1$H-NMR (CDCl$_3$) δ: 9.77 (s, 1H), 8.24 (s, 1H), 8.12 (dd, 1H), 7.82 (q, 1H), 7.21 (s, 1H), 7.18 (s, 1H), 6.82 (dd, 1H), 6.09 (s, 2H), 4.40 (q, 2H), 3.13–3.18 (m, 2H), 1.65–1.72 (m, 2H), 1.40 (t, 3H), 1.00 (t, 3H). |
| 110. | | 7-[2-(6-Fluoro-pyridin-2-yl)-imidazol-1-ylmethyl]-8-propyl-imidazo[1,2-c]pyrimidine-2-carboxylic acid ethyl ester | LC-MS, M + 1 409.2; $^1$H-NMR (CDCl$_3$) δ: 8.78 (s, 1H), 8.12 (s, 1H), 8.11 (dd, 1H), 7.81 (q, 1H), 7.18 (s, 1H), 7.17 (s, 1H), 6.81 (dd, 1H), 6.02 (s, 2H), 4.44 (q, 2H), 3.15–3.21 (m, 2H), 1.68–1.75 (m, 2H), 1.40 (t, 3H), 1.00 (t, 3H). |
| 111. | | 7-[2-(6-Fluoro-pyridin-2-yl)-imidazol-1-ylmethyl]-2-methyl-8-propyl-imidazo[1,2-c]pyrimidine | LC-MS, M + 1 351.1; $^1$H-NMR (CDCl$_3$) δ: 8.69 (s, 1H), 8.11 (dd, 1H), 7.83 (q, 1H), 7.30 (s, 1H), 7.16 (s, 1H), 7.15 (s, 1H), 6.83 (dd, 1H), 6.02 (s, 2H), 3.04–3.10 (m, 2H), 2.46 (s, 3H), 1.65–1.72 (m, 2H), 0.97 (t, 3H). |
| 112. | | 7-[2-(6-Fluoro-pyridin-2-yl)-imidazol-1-ylmethyl]-8-propyl-2-trifluoromethyl-imidazo[1,2-c]pyrimidine | LC-MS, M + 1 405.1; $^1$H-NMR (CDCl$_3$) δ: 8.79 (s, 1H), 8.10 (dd, 1H), 7.87 (s, 1H), 7.82 (q, 1H), 7.18 (s, 1H), 7.17 (s, 1H), 6.82 (dd, 1H), 6.04 (s, 2H), 3.12–3.17 (m, 2H), 1.68–1.76 (m, 2H), 0.97 (t, 3H). |
| 113. | | 8-Propyl-7-(2-pyridin-2-yl-imidazol-1-ylmethyl)-imidazo[1,2-c]pyrimidine | LC-MS, M + 1 319.1; $^1$H-NMR (CDCl$_3$) δ: 8.82 (s, 1H), 8.55 (dd, 1H), 8.21 (d, 1H), 7.73–7.78 (m, 1H), 7.65 (d, 1H), 7.57 (d, 1H), 7.20–7.27 (m, 1H), 7.20 (s, 1H), 7.15 (s, 1H), 6.10 (s, 2H), 3.04–3.10 (m, 2H), 1.63–1.70 (m, 2H), 0.96 (t, 3H). |
| 114. | | 8-Propyl-7-(2-pyridin-2-yl-imidazol-1-ylmethyl)-2-trifluoromethyl-imidazo[1,2-c]pyrimidine | LC-MS, M + 1 387.1; $^1$H-NMR (CDCl$_3$) δ: 8.80 (s, 1H), 8.51 (dd, 1H), 8.21 (d, 1H), 7.86 (d, 1H), 7.71–7.78 (m, 1H), 7.20–7.19 (m, 1H), 7.18 (s, 1H), 7.17 (s, 1H), 6.10 (s, 2H), 3.10–3.15 (m, 2H), 1.66–1.74 (m, 2H), 0.98 (t, 3H). |

| Compound | | Name | LC-MS/NMR |
|---|---|---|---|
| 115. | | 7-[2-(2,6-Difluoro-phenyl)-imidazol-1-ylmethyl]-8-propyl-imidazo[1,2-c]pyrimidine | LC-MS, M + 1 354.1; $^{1}$H-NMR (CDCl$_3$) δ: 8.81 (s, 1H), 7.65 (d, 1H), 7.58 (d, 1H), 7.38–7.48 (m, 1H), 7.23 (d, 1H), 7.19 (d, 1H), 7.01 (t, 2H), 5.12 (s, 2H), 2.69–2.74 (m, 2H), 1.51–1.59 (m, 2H), 0.90 (t, 3H). |
| 116. | | 7-[2-(2,6-Difluoro-phenyl)-imidazol-1-ylmethyl]-8-propyl-2-trifluoromethyl-imidazo[1,2-c]pyrimidine | LC-MS, M + 1 422.1; $^{1}$H-NMR (CDCl$_3$) δ: 8.82 (s, 1H), 7.89 (d, 1H), 7.44–7.49 (m, 1H), 7.25 (s, 1H), 7.20 (s, 1H), 7.00 (t, 2H), 5.13 (s, 2H), 2.70–2.76 (m, 2H), 1.53–1.61 (m, 2H), 0.89 (t, 3H). |
| 117. | | 7-[2-(3-Fluoro-pyridin-2-yl)-imidazol-1-ylmethyl]-8-propyl-imidazo[1,2-c]pyrimidine | LC-MS, M + 1 337.1; $^{1}$H-NMR (CDCl$_3$) δ: 8.80 (s, 1H), 8.44–8.46 (m, 1H), 7.64 (d, 1H), 7.57 (d, 1H), 7.51–7.55 (m, 1H), 7.28–7.34 (m, 1H), 7.24 (d, 1H), 7.20 (d, 1H), 5.77 (s, 2H), 2.91–2.96 (m, 2H), 1.59–1.67 (m, 2H), 0.96 (t, 3H). |
| 118. | | 7-[(pyridin-2-yl)-imidazol-1-ylmethyl]-2-phenyl-8-propyl-imidazo[1,2-c]pyrimidine | LC-MS, M + 1 394.5; $^{1}$H-NMR (CDCl$_3$) δ: 8.78 (s, 1H), 8.56 (d, 1H), 8.22 (d, 1H), 7.97 (s, 1H), 7.94 (s, 1H), 7.80 (s, 1H), 7.46 (t, 1H), 7.44 (t, 1H), 7.36 (q, 1H), 7.16–7.23 (m, 3H), 6.09 (s, 2H), 3.09–3.14 (m, 2H), 1.69–1.77 (m, 2H), 0.98 (t, 3H). |

C. 7-[2-(6-fluoro-pyridin-2-yl)-imidazol-1-ylmethyl]-5-methyl-8-propyl-imidazo[1,2-c]pyrimidine (119)

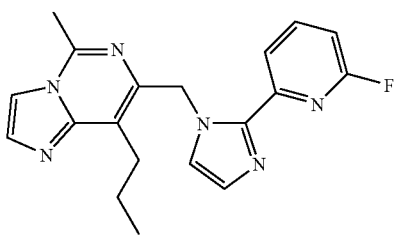

Step 1. Preparation of 2-oxo-3-propyl-succinic acid diethyl ester (120)

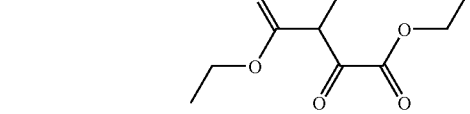

At room temperature, a mixture of pentanoic acid ethyl ester (0.4 mol) and diethyl oxalate (compound 11 in Scheme 1) (73.1 g, 0.5 mol) is added to a solution of NaOEt (32.7 g, 0.48 mol) in EtOH (250 ml). The mixture is stirred at room temperature for 30 minutes and EtOH is distilled away. The residue is then purified by vacuum distillation, which provides the product (120) as a clear oil.

Step 2. Preparation of 2-methyl-5-propyl-6-hydroxy-pyrimidine-4-carboxylic Acid Ethyl Ester (121)

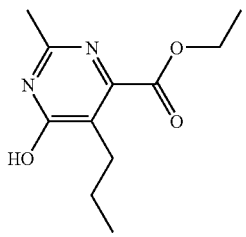

A mixture of 120 (20 mmol), acetamidine hydrochloride (40 mmol) and K₂CO₃ (6.9 g, 50 mmol) in EtOH (50 ml) is heated at 70° C. overnight. The solid is filtered and the residue is dissolved in water (30 ml). Acetic acid is added to adjust the pH to 4. The mixture is then extracted with CH₂Cl₂ (4×50 ml) and the combined extracts are washed with brine (100 ml). The solution is dried (Na₂SO₄) and evaporated in vacuo to give a light yellow solid (121), which is used directly in the next step.

Step 3. Preparation of 2-methyl-5-propyl-6-chloro-pyrimidine-4-carboxylic Acid Ethyl Ester (122)

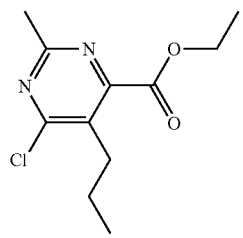

A mixture of 121 (10 mmol) and POCl₃ (25 ml) is heated at 85° C. for 4 hours. The solvent is removed in vacuo and EtOAc (40 ml) and water (30 ml) are added to the residue. NaHCO₃ is carefully added until the pH of the aqueous layer is greater than 7. The layers are separated and the aqueous layer is extracted with EtOAc (2×30 ml). The combined extracts are washed with brine (50 ml), dried (Na₂SO₄) and evaporated. Flash column purification of the residue with 3:1 EtOAc, hexane provides the product (122) as a light yellow oil.

Step 4. Preparation of 2-methyl-5-propyl-4-chloromethyl-6-chloro-pyrimidine (123)

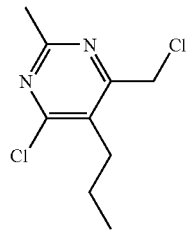

NaBH₄ (91 mg, 2.4 mmol) is added to a solution of 122 (0.48 mmol) in MeOH (10 ml), cooled to 0° C., and the mixture is stirred at room temperature overnight. The solvent is removed in vacuo and water (10 ml) and EtOAc (10 ml) are added to the residue. The layers are separated and the aqueous layer is extracted with EtOAc (10 ml). The combined extracts are washed with brine (20 ml), dried (Na₂SO₄) and evaporated. The resulting light oil is then dissolved in CH₂Cl₂ (5 ml) and thionyl chloride (1 ml) is added. The mixture is stirred at room temperature for 4 hours. The solvent is then removed. EtOAc (15 ml) is added to the residue and it is washed with NaHCO₃ (15 ml) and brine (15 ml), then dried (Na₂SO₄) and evaporated. Flash column chromatography of the residue provides the product (123) as a yellowish oil.

Step 5. Preparation of 4-chloro-6-[2-(6-fluoro-pyridin-2-yl)-imidazol-1-ylmethyl]-2-methyl-5-propyl-pyrimidine (124)

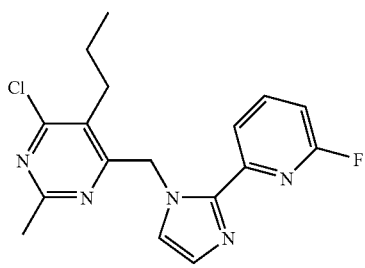

A mixture of 123 (1 mmol), 6-fluoro-2-1H-imidazol-2-yl)-pyridine prepared as described above (163 mg, 1 mmol) and K₂CO₃ (552 mg, 4 mmol) in DMF (6 ml) is stirred at room temperature overnight. The solvent is removed in vacuo and EtOAc (10 ml) and water (10 ml) are added to the residue. The layers are separated and the aqueous layer is extracted with EtOAc (10 ml). The combined extracts are washed with-brine (10 ml), dried (Na₂SO₄) and evaporated. PTLC separation of the residue with 5% MeOH in CH₂Cl₂ provides the product (124) as a white solid.

Step 6. Preparation of 4-azido-6-[2-(6-fluoro-pyridin-2-yl)-imidazol-1-ylmethyl]-2-methyl-5-propyl-pyrimidine (125)

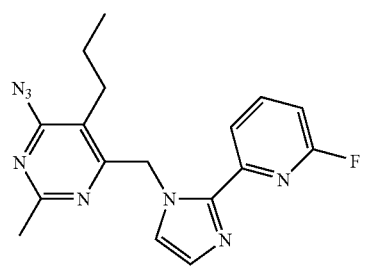

A solution of 124 (2.25 mmol) and NaN₃ (731 mg, 11.25 mmol) in DMF (15 ml) is heated at 70° C. in a sealed tube overnight. The solvent is removed in vacuo and water (10 ml) and EtOAc (10 ml) are added to the residue. The layers are separated and the aqueous layer is extracted with EtOAc (2×10 ml). The combined extracts are washed with brine (15 ml) and dried with Na₂SO₄. The solvent is removed in vacuo and the resulting yellow oil (125) is used in the next step without further purification.

Step 7. Preparation of 4-amino-6-[2-(6-fluoro-pyridin-2-yl)-imidazol-1-ylmethyl]-2-methyl-5-propyl-pyrimidine (126)

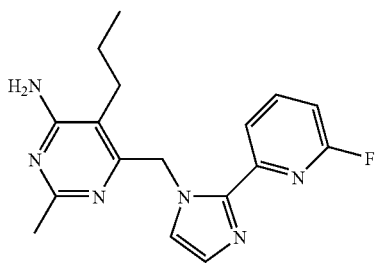

Pd/C (10%, 10 mg) is added to a solution of 4-azido-6-[2-(6-fluoro-pyridin-2-yl)-imidazol-1-ylmethyl]-2-methyl-5-propyl-pyrimidine (2 mmol) (125) in MeOH (20 ml) and the mixture is stirred under $H_2$ at 30 psi for 4 hours. The catalyst is filtered out and the filtrate is evaporated in vacuo. The resulting light yellow solid (126) is used in the next step without further purification.

Step 8. Preparation of 7-[2-(6-fluoro-pyridin-2-yl)-imidazol-1-ylmethyl]-5-methyl-8-propyl-imidazo[1,2-c]pyrimidine (119)

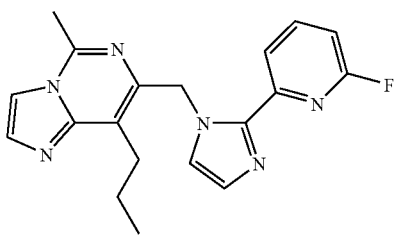

A solution of 126 (1.2 mmol) and chloroacetaldehyde (1 mL) in DMF (10 ml) is heated at 70° C. in a sealed tube overnight. The solvent is removed in vacuo and water (15 ml) and EtOAc (15 ml) are added to the residue. The layers are separated and the aqueous layer is extracted with EtOAc (15 ml). The combined extracts are washed with brine (15 ml), dried ($Na_2SO_4$) and evaporated. PTLC separation of the residue with 10% MeOH in $CH_2Cl_2$ provides the title compound (119) as a white solid; LC-MS, M+1 351.1; $^1$H-NMR (CDCl$_3$) δ: 8.10 (dd, 1H), 7.85 (q, 1H), 7.66 (d, 1H), 7.44 (d, 1H), 7.20 (d, 1H), 7.12 (d, 1H), 6.86 (dd, 1H), 6.02 (s, 2H), 3.01–3.07 (m, 2H), 2.69 (s, 3H), 1.60–1.67 (m, 2H), 0.94 (t, 3H).

D. Synthesis of 7-[2-(6-fluoro-pyridin-2-yl)-imidazol-1-ylmethyl]-8-propyl-imidazo[1,2-c]pyrimidine-2-carbonitrile (127)

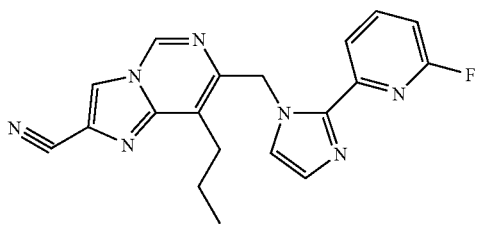

Step 1. Preparation of 7-[2-(6-fluoro-pyridin-2-yl)-imidazol-1-ylmethyl]-8-propyl-imidazo[1,2-c]pyrimidine-2-carboxylic acid amide (128)

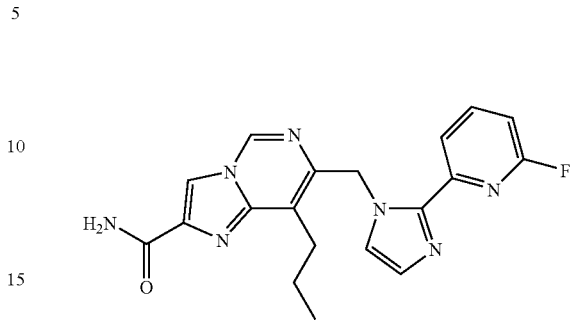

Ammonia gas is passed through a stirred solution of 7-[2-(6-fluoro-pyridin-2-yl)-imidazol-1-ylmethyl]-8-propyl-imidazo[1,2-c]pyrimidine-2-carboxylic acid ethyl ester (110, above) (1 mmol) in EtOH (7 ml) in a sealed tube for 20 minutes at 0° C. The tube is then sealed and heated at 90° C. for 2 days. The solvent is evaporated and the residue (128) is used directly in the next step without further purification.

Step 2. Preparation of 7-[2-(6-fluoro-pyridin-2-yl)-imidazol-1-ylmethyl]-8-propyl-imidazo[1,2-c]pyrimidine-2-carbonitrile (127)

POCl$_3$ (0.5 ml) is added to a solution of 128 (0.75 mmol) in pyridine (3 ml) and the mixture is stirred at room temperature overnight. The solvent is evaporated and the residue is purified by PTLC (5% MeOH in $CH_2Cl_2$) to afford the product (127); LC-MS, M+1 362.1; $^1$H-NMR (CDCl$_3$) δ: 8.77 (s, 1H), 8.11 (dd, 1H), 8.03 (s, 1H), 7.82 (q, 1H), 7.19 (s, 1H), 7.18 (s, 1H), 6.82 (dd, 1H), 6.03 (s, 2H), 3.11–3.17 (m, 2H), 1.67–1.75 (m, 2H), 1.01 (t, 3H).

E. 7-[2-(6-Fluoro-pyridin-2-yl)-imidazol-1-ylmethyl]-8-propyl-imidazo[1,2-c]pyrimidine-3-carbonitrile (129)

This compound is synthesized as described in the above Schemes 1 and 3 and as further illustrated in Example 1D.

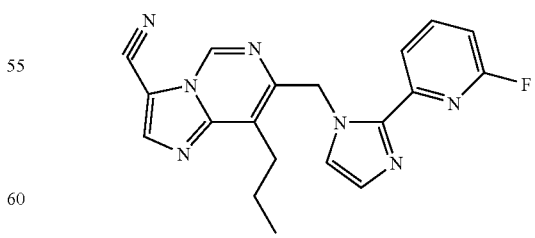

LC-MS, M+1 362.1; $^1$H-NMR (CDCl$_3$) δ: 8.95 (s, 1H), 8.17 (s, 1H), 8.14 (dd, 1H), 7.83 (q, (1H), 7.21 (s,1H), 7.20 (s, 1H), 6.82 (dd, 1H), 6.09 (s, 2H), 3.17–3.22 (m, 2H), 1.68–1.75 (m, 2H), 1.01 (t, 3H).

Example 2

Synthesis of [1,2,4]triazolo[1,5-c]pyrimidines

A. 7-[2-(3-Fluoro-pyridin-2-yl)-imidazol-1-ylmethyl]-2-methyl-8-propyl-[1,2,4]triazolo[1,5-c]pyrimidine (130)

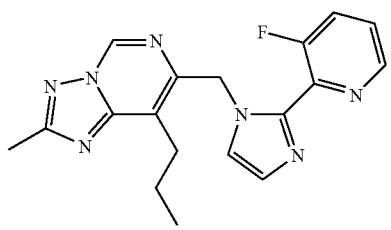

Step 1. Preparation of 3-fluoro-2-(1H-imidazol-2-yl)-pyridine

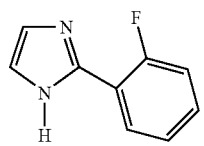

3-Fluoro-2-(1H-imidazol-2-yl)-pyridine, which is used as a starting material (e.g., in place 6-fluoro-2-(1H-imidazol-2-yl)-pyridine in the procedure given above) in the synthesis of certain compounds is prepared as follows: n-BuLi (2.5 M in hexane, 86 mL, 1.05 eq.) is added dropwise over a 90 minute interval to a solution of 3-fluoropyridine (20 g, 0.206 mol) and N,N,N'N'-tetramethylethylenediamine (31.3 mL, 0.206 mol) in ethyl ether (350 mL) at −78° C. under nitrogen. The mixture is stirred at this temperature for an additional 3 hours. Anhydrous DMF (45 mL) is then added at the same temperature. The mixture is allowed to warm to room temperature overnight. Water (170 mL) is added and organic layer separated. The aqueous layer is extracted with ether (3×200 mL), and then with ethyl acetate (2×200 mL). The combined organic layers are dried (MgSO₄) and solvent removed in vacuo. The crude is purified by column chromatography (hexane:ether 2:1) to give 3-fluoro-pyridine-2-carbaldehyde as a yellowish oil.

Glyoxal (40% w/w H₂O, 16.0 g, 0.110 mol) and ammonium hydroxide (con. 29 mL) are added to a solution of 3-fluoro-pyridine-2-carbaldehyde (11.5 g, 0.092 mol) in MeOH (450 mL) at 0° C. The mixture is allowed to warm gradually to room temperature over an 18 hour period. The solvent is removed. Water (100 mL) is added to the residue and the mixture is extracted with methylene chloride (5×150 mL). The combined organic layers are washed with brine (2×100 mL), dried and solvent removed. The crude is triturated with ethyl ether (200 mL) to give 3-fluoro-2-(1H-imidazol-2-yl)-pyridine as a solid.

Step 2. Preparation of {6-[2-(3-fluoro-pyridin-2-yl)-imidazol-1-ylmethyl]-5-propyl-pyrimidin-4-yl}-hydrazine (131)

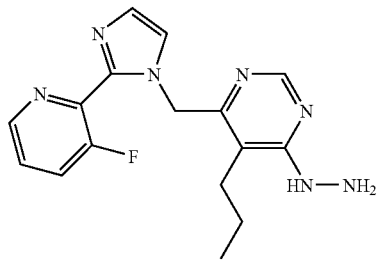

A mixture of 4-chloro-6-[2-(3-fluoro-pyridin-2-yl)-imidazol-1-ylmethyl]-5-propyl-pyrimidine (prepared from 5-propyl-6-bromomethyl-4-chloro-pyrimidine and 3-fluoro-2-(1H-imidazol-2-yl)-pyridine essentially as described in Example 1) (2.5 g, 7.5 mmol) and hydrazine monohydrate (1.37 g, 27.4 mmol) in EtOH (15 mL) is heated in a sealed tube at 70° C. overnight. The solvent is removed in vacuo and the residue is triturated with ethyl acetate and ethyl ether. Filtration gives a white solid (131) which is used in the next step without further purification.

Step 3. Preparation of 7-[2-(3-fluoro-pyridin-2-yl)-imidazol-1-yl-methyl]-2-methyl-8-propyl-[1,2,4]triazolo[1,5-c]-pyrimidine (130)

A solution of 131 (2.5 g) in acetic acid (25 mL) is heated in a sealed tube at 110° C. overnight. Excess acetic acid is removed in vacuo and to the residue is added NaHCO₃ (aq.) (50 mL) and dichloromethane (150 mL). The organic layer is separated and the aqueous layer is extracted with dichloromethane (2×40 mL). The combined organic layers are dried (NaSO₄) and solvent removed. The crude product (130) is separated by column chromatography (5% MeOH in dichloromethane); LC-MS, M+1 352.1; $^1$H-NMR (CDCl₃) δ: 9.03 (s, 1H), 8.38 (dt, 1H), 7.53 (td, 1H), 7.31–7.25 (m, 1H), 7.26, (d, 1H), 7.20 (d, 1H), 5.83 (s, 2H), 2.93 (t, 2H), 2.60 (s, 3H), 1.70–1.58 (m, 2H), 0.958 (t, 3H).

B. Synthesis of Additional [1,2,4]triazolo[1,5-c]pyrimidines

The compounds shown in Table 2 are synthesized via methods provided in Schemes 1 and 4 and further illustrated by Example 2A. All compounds in Table 2 exhibit a $K_i$ of less than 1 micromolar in the ligand binding assay provided in Example 6, as do compounds 130 (above) and compounds 155–158, 167, 171, 173–177 and 186–189 (below).

TABLE 2

| | Compound | Name | LC-MS/NMR |
|---|---|---|---|
| 132. | 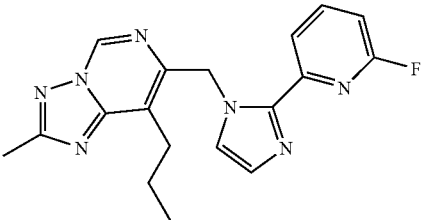 | 7-[2-(6-Fluoro-pyridin-2-yl)-imidazol-1-ylmethyl]-2-methyl-8-propyl-[1,2,4]triazolo[1,5-c]pyrimidine | LC-MS, M + 1 352.1; $^1$H-NMR (CDCl$_3$) δ: 9.01 (s, 1H), 8.12 (dd, 1H), 7.82 (dd, 1H), 7.00 (s, 2H), 6.80 (dd, 1H), 6.05 (s, 2H), 3.12 (q, 2H), 2.60 (s, 3H), 1.63–1.78 (m, 2H), 1.02 (t, 3H). |
| 133. | 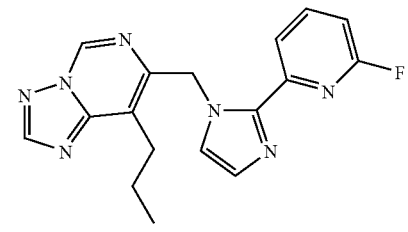 | 7-[2-(6-Fluoro-pyridin-2-yl)-imidazol-1-ylmethyl]-8-propyl-[1,2,4]triazolo[1,5-c]pyrimidine | LC-MS, M + 1 338.1; $^1$H-NMR (CDCl$_3$) δ: 9.15 (s, 1H), 8.39 (s, 1H), 8.13 (dd, 1H), 7.82 (dd, 1H), 7.22 (s, 1H), 7.20 (s, 1H), 6.80 (dd, 1H), 6.08 (s, 2H), 3.16 (q, 2H), 1.63–1.78 (m, 2H), 1.02 (t, 3H). |
| 134. | 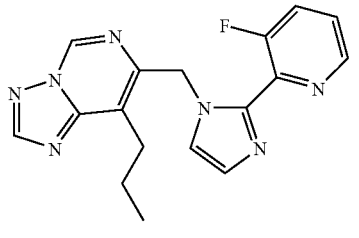 | 7-[2-(3-Fluoro-pyridin-2-yl)-imidazol-1-ylmethyl]-8-propyl-[1,2,4]triazolo[1,5-c]pyrimidine | LC-MS, M + 1 338.1; $^1$H-NMR (CDCl$_3$) δ: 9.16 (s, 1H), 8.40 (dt, 1H), 8.36 (s, 1H), 7.55 (dt, 1H), 7.26–7.32 (m, 2H), 7.22 (d, 1H), 5.88 (s, 2H), 2.99 (t, 2H), 1.62–1.71 (m, 2H), 0.98 (t, 3H). |
| 135. | 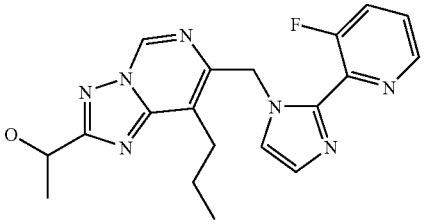 | 1-{7-[2-(3-Fluoro-pyridin-2-yl)-imidazol-1-ylmethyl]-8-propyl-[1,2,4]triazolo[1,5-c]pyrimidin-2-yl}-ethanol | LC-MS: Calc 381.4; Found 382.1 (M + 1). |
| 136. | 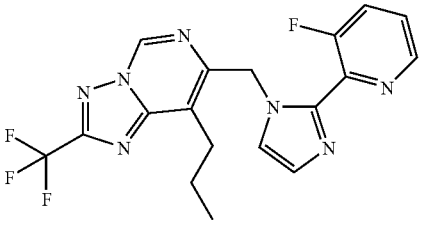 | 7-[2-(3-Fluoro-pyridin-2-yl)-imidazol-1-ylmethyl]-8-propyl-2-trifluoromethyl-[1,2,4]triazolo[1,5-c]pyrimidine | $^1$H-NMR (CDCl$_3$) δ: 9.19 (s, 1H); 8.35 (d, 1H), 7.55 (dd, 1H), 7.27–7.33 (m, 2H), 7.22 (s, 1H), 5.84 (s, 2H), 3.02 (q, 2H), 1.62–1.75 (m, 2H), 0.99 (t, 3H). |
| 137. | 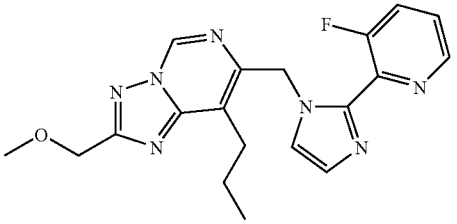 | 7-[2-(3-Fluoro-pyridin-2-yl)-imidazol-1-ylmethyl]-2-methoxymethyl-8-propyl[1,2,4]triazolo[1,5-c]pyrimidine | $^1$H-NMR (CDCl$_3$) δ: 9.08 (s, 1H), 8.38 (d, 1H), 7.55 (dd, 1H), 7.27–7.33 (m, 2H), 7.22 (s, 1H), 5.84 (s, 2H), 4.75 (s, 2H), 3.57 (s, 3H), 2.98 (q, 2H), 1.60–1.75 (m, 2H), 0.99 (t, 3H). |

TABLE 2-continued

| | Compound | Name | LC-MS/NMR |
|---|---|---|---|
| 138. | | 7-[2-(6-Fluoro-pyridin-2-yl)-imidazol-1-ylmethyl]-2-methoxymethyl-8-propyl-[1,2,4]triazolo[1,5-c]pyrimidine | $^1$H-NMR (CDCl$_3$) δ: 9.08 (s, 1H), 8.13 (dd, 1H), 7.82 (dd, 1H), 7.21 (s, 2H), 6.80 (dd, 1H), 6.06 (s, 2H), 4.75 (s, 2H), 3.57 (s, 3H), 3.15 (q, 2H), 1.63–1.79 (m, 2H), 1.01 (t, 3H). |
| 139. | | 2-Cyclobutyl-7-[2-(6-fluoro-pyridin-2-yl)-imidazol-1-ylmethyl]-8-propyl-[1,2,4]triazolo[1,5-c]pyrimidine | $^1$H-NMR (CDCl$_3$) δ: 9.02 (s, 1H), 8.13 (dd, 1H), 7.82 (dd, 1H), 7.21 (s, 2H), 6.80 (dd, 1H), 6.06 (s, 2H), 3.75–3.86 (m, 1H), 3.12 (q, 2H), 2.41-2.55 (m, 4H), 1.95–2.05 (m, 1H), 1.63–1.79 (m, 3H), 1.01 (t, 3H). |
| 140. | | 8-Propyl-7-(2-pyridin-2-yl-imidazol-1-ylmethyl)-[1,2,4]triazolo[1,5-c]pyrimidine | $^1$H-NMR (CDCl$_3$) δ: 9.19 (s, 1H), 8.48 (dd, 1H), 8.39 (s, 1H), 8.25 (dd, 1H), 7.78 (dd, 1H), 7.17–7.28 (m, 3H), 6.18 (s, 2H), 3.11 (q, 2H), 1.65–1.78 (m, 2H), 0.99 (t, 3H). |
| 141. | | 7-[2-(2,5-Difluoro-phenyl)-imidazol-1-ylmethyl]-2-methyl-8-propyl-[1,2,4]triazolo[1,5-c]pyrimidine | $^1$H-NMR (CDCl$_3$) δ: 9.05 (s, 1H), 7.31–7.38 (m, 1H), 7.08–7.22 (m, 4H), 5.22 (s, 2H), 2.75 (q, 2H), 2.61 (s, 3H), 1.48–1.60 (m, 2H), 0.92 (t, 3H). |
| 142. | | 7-[2-(6-Methoxy-pyridin-2-yl)-imidazol-1-ylmethyl]-8-propyl-[1,2,4]triazolo[1,5-c]pyrimidine | $^1$H-NMR (CDCl$_3$) δ: 9.21 (s, 1H), 8.39 (s, 1H), 7.85 (d, 1H), 7.68 (t, 1H), 7.15 (s, 1H), 7.01 (s, 1H), 6.74 (d, 1H), 6.25 (s, 2H), 3.85 (s, 3H), 2.93 (q, 2H), 1.51–1.62 (m, 2H), 0.88 (t, 3H). |
| 143. | | 2-Methyl-8-propyl-7-(2-thiazol-2-yl-imidazol-1-ylmethyl)-[1,2,4]triazolo[1,5-c]pyrimidine | $^1$H-NMR (CDCl$_3$) δ: 9.06 (s, 1H), 7.77 (d, 1H), 7.31 (d, 1H), 7.20 (s, 1H), 7.14 (s, 1H), 6.08 (s, 2H), 3.08 (q, 2H), 2.60 (s, 3H), 1.63–1.71 (m, 2H), 0.97 (t, 3H). |

TABLE 2-continued

| Compound | Name | LC-MS/NMR |
|---|---|---|
| 144. | 2-Methyl-8-propyl-7-(2-pyridin-2-yl-imidazol-1-ylmethyl)-[1,2,4]triazolo[1,5-c]pyrimidine | $^1$H-NMR (CDCl$_3$) δ: 9.04 (s, 1H), 8.48 (s, 1H), 8.23 (d, 1H), 7.73 (dd, 1H), 7.13–7.22 (m, 3H), 6.13 (s, 2H), 3.06 (q, 2H), 2.60 (s, 3H), 1.62–1.78 (m, 2H), 0.98 (t, 3H). |
| 145. | 6-[1-(8-Propyl-[1,2,4]triazolo[1,5-c]pyrimidin-7-ylmethyl)-1H-imidazol-2-yl]-pyridin-2-ol | LC-MS: Calc 335.4; found 336.1 (M + 1). |
| 146. | 7-[2-(2,6-Difluoro-phenyl)-imidazol-1-ylmethyl]-8-propyl-[1,2,4]triazolo[1,5-c]pyrimidine | $^1$H-NMR (CDCl$_3$) δ: 9.19 (s, 1H), 8.39 (s, 1H), 7.39–7.48 (m, 1H), 7.26 (s, 1H), 7.21 (s, 1H), 6.95–7.03 (m, 2H), 5.20 (s, 2H), 2.71 (q, 2H), 1.46–1.60 (m, 2H), 0.89 (t, 3H). |
| 147. | 8-Propyl-7-(2-thiophen-2-yl-imidazol-1-ylmethyl)-[1,2,4]triazolo[1,5-c]pyrimidine | $^1$H-NMR (CDCl$_3$) δ: 9.24 (s, 1H), 8.41 (s, 1H), 7.42 (d, 1H), 7.36 (d, 1H), 7.15 (s, 1H), 7.10 (dd, 1H), 7.03 (s, 1H), 5.46 (s, 2H), 2.89 (q, 2H), 1.60–1.71 (m, 2H), 0.99 (t, 3H). |
| 148. | 2-Methyl-8-propyl-7-(2-pyridazin-3-yl-imidazol-1-ylmethyl)-[1,2,4]triazolo[1,5-c]pyrimidine | $^1$H-NMR (CDCl$_3$) δ: 9.05 (dd, 1H), 9.01 (s, 1H), 8.39 (dd, 1H), 7.52 (dd, 1H), 7.25 (s, 1H), 7.22 (s, 1H), 6.21 (s, 2H), 3.08 (q, 2H), 2.59 (s, 3H), 1.63–1.77 (m, 2H), 0.98 (t, 3H). |
| 149. | 7-[2-(2,5-Difluoro-phenyl)-imidazol-1-ylmethyl]-8-ethyl-[1,2,4]triazolo[1,5-c]pyrimidine | $^1$H NMR (CDCl$_3$) δ: 1.14 (t, 3H, J = 7.5 Hz), 2.85 (q, 2H, J = 7.5 Hz), 5.26 (s, 2H), 7.05–7.35 (m, 5H), 8.38 (s, 1H), 9.19 (s, 1H). LC-MS (M + 1) 341.11. |
| 150. | 7-[2-(2,5-Difluoro-phenyl)-imidazol-1-ylmethyl]-8-ethyl-2-methyl-[1,2,4]triazolo[1,5-c]pyrimidine | $^1$H NMR δ (CDCL$_3$) 1.11 (t, 3H, J = 7.5 Hz), 2.60 (s, 3H), 2.82 (q, 2H, J = 7.5 Hz), 5.22 (s, 2H), 7.05–7.35 (m, 5H), 9.06 (s, 1H). LC-MS (M + 1) 355.12. |

TABLE 2-continued

| Compound | Name | LC-MS/NMR |
|---|---|---|
| 151. | 8-Ethyl-7-[2-(5-fluoro-2-methyl-phenyl)-imidazol-1-ylmethyl]-[1,2,4]triazolo[1,5-c]pyrimidine | ¹H NMR δ (CDCl₃) 1.15 (t, 3H, J = 7.5 Hz), 2.16 (s, 3H), 2.78 (q, 2H, J = 7.5 Hz), 5.11 (s, 2H), 7.01–7.30 (m, 5H), 8.38 (s, 1H), 9.20 (s, 1H). LC-MS (M + 1) 337.15. |
| 152. | 8-Ethyl-7-[2-(5-fluoro-2-methyl-phenyl)-imidazol-1-ylmethyl]-2-methyl-[1,2,4]triazolo[1,5-c]pyrimidine | ¹H NMR δ (CDCl₃) 1.12 (t, 3H, J = 7.5 Hz), 2.16 (s, 3H), 2.61 (s, 3H), 2.78 (q, 2H, J = 7.5 Hz), 5.08 (s, 2H), 7.01–7.30 (m, 5H), 9.07 (s, 1H). LC-MS (M + 1) 351.16. |
| 153. | 2-Ethyl-7-[2-(3-fluoro-pyridin-2-yl)-imidazol-1-ylmethyl]-8-propyl-[1,2,4]triazolo[1,5-c]pyrimidine | ¹H NMR δ (CDCl₃) 0.95 (t, 3H, J = 5.4 Hz), 1.39 (t, 3H, J = 5.7 Hz), 1.63 (p, 2H, J = 5.4 Hz), 2.93 (m, 4H), 5.83 (s, 2H), 7.19 (d, 1H, J = 0.6 Hz), 7.25–7.30 (m, 2H), 7.53 (t, 1H, J = 7.2 Hz), 8.39 (d, 1H, J = 3.3 Hz), 9.04 (s, 1H). LC-MS (M + 1) 366.15. |
| 154. | 2-Difluoromethyl-7-[2-(3-fluoro-pyridin-2-yl)-imidazol-1-ylmethyl]-8-propyl-[1,2,4]triazolo[1,5-c]pyrimidine | ¹H NMR δ (CDCl₃) 9.16 (s, 1H), 8.35 (dt, 1H), 7.54 (td, 1H), 7.26–7.31 (m, 2H), 7.22 (d, 1H), 6.87 (t, 1H), 5.90 (s, 2H), 3.03 (t, 2H), 1.64–1.74 (m, 2H), 0.99 (t, 3H). LC-MS (M + 1) 388.16. |

C. 7-[2-(3-fluoro-pyridin-2-yl)-imidazol-1-ylmethyl]-2-phenyl-8-propyl-[1,2,4]triazolo[1,5-c]pyrimidine (155)

A mixture of {6-[2-(3,-fluoro-pyridin-2-yl)-imidazol-1-ylmethyl]-5-propyl-pyrimidin-4-yl}-hydrazine (131) (60 mg, 0.18 mmol), benzaldehyde (21 mg, 0.2 mmol) in EtOH is refluxed for 4 hours. Solvent is removed in vacuo. HOAc (2 mL) is added to the residue, and then bromine (0.3 mmol) is slowly added. The mixture is stirred at room temperature overnight. Solvent is removed in vacuo and the residue is treated with NaHCO₃ (aq) and DCM. The organic layer is separated and the aqueous layer is extracted with DCM (2×0 mL). The combined organic layers are dried (MgSO₄), the solvent is removed, and the crude purified by PTLC (10% MeOH in DCM) to give a white solid; ¹H-NMR (CDCl₃) δ: 8.93 (s, 1H), 8.44 (dd, 1H), 7.78–7.88 (m, 2H), 7.51–7.63 (m, 4H), 7.22–7.36 (m, 3H), 5.82 (s, 2H), 3.05 (q, 2H), 1.70–1.80 (m, 2H), 1.02 (t, 3H).

D. 7-[2-(3-Fluoro-pyridin-2-yl)-imidazol-1-ylmethyl]-2-isopropyl-8-propyl-[1,2,4]triazolo[1,5-c]pyrimidine (156)

Isobutyric anhydride (0.5 mL) is added to a mixture of 131 (45 mg) in methylene chloride (10 mL). The mixture is stirred at room temperature for 1 hour. The solvent is removed to get residue, LC-MS (M+1) 398.17. The residue is dissolved in POCl₃ (1 mL), and the mixture is heated at 85° C. for 1 hour. Excess POCl₃ is removed. The residue is dissolved in methylene chloride, and washed with sat. NaHCO₃, dried, and purified by TLC with 5% MeOH in methylene chloride to give the title product (156). ¹H NMR δ (CDCl$_3$) 1.02 (t, 3H, J=5.4 Hz), 1.43 (d, 6H, J=6.0 Hz), 1.71 (p, 2H, J=5.4 Hz), 2.93 (m, 2H), 3.29 (sep, 1H, J=6.0 Hz), 5.57 (s, 2H), 7.22–7.36 (m, 2H), 7.70–7.82 (m, 2H), 8.82 (d, 1H, J=3.3 Hz), 9.04 (s, 1H). LC-MS (M+1) 380.17.

E. 2-Fluoromethyl-7-[2-(3-fluoro-pyridin-2-yl)-imidazol-1-ylmethyl]-8-propyl-[1,2,4]triazolo[1,5-c]pyrimidine (157)

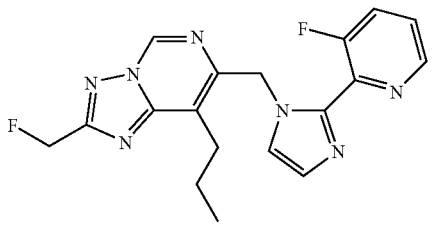

To a solution {7-[2-(3-fluoro-pyridin-2-yl)-imidazol-1-ylmethyl]-8-propyl-[1,2,4]triazolo[1,5-c]pyrimidin-2-yl}-methanol (compound 223, below) (31 mg, 0.08 mmol) in dichloromethane (5 mL) is added bis(2-methoxyethyl)aminosulfur trifluoride (0.2 ml, 50% in THF) at room temperature under N$_2$. The mixture is stirred for two hours, and is poured into saturated NaHCO$_3$ (10 mL), and after CO$_2$ evolution ceases it is extracted into dichloromethane, dried (MgSO$_4$), filtered and evaporated in vacuo. PTLC by 5% MeOH/dichloromethane gives the pure product (157). $^1$H NMR: 0.98 (3H, t, J=5.4 Hz), 1.67 (2H, m), 2.99 (2H, m), 5.69 (2H, d, J=35.1 Hz), 5.88 (2H, s), 7.22 (1H, s), 7.22–7.31 (2H, m), 7.54 (1H, t, J=6.0 Hz), 8.39 (1H, s), 9.13 (1H, s). LCMS (M+1) 370.20.

F. 8-(2,2-Difluoro-ethyl)-7-[2-(3-fluoro-pyridin-2-yl)-imidazol-1-ylmethyl]-2-methyl-[1,2,4]triazolo[1,5-c]pyrimidine (158)

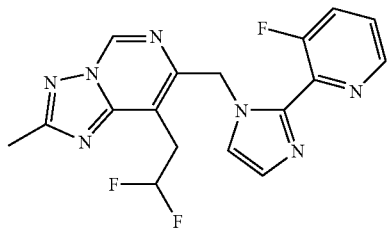

Step 1. Preparation of 2-(2-benzyloxy-ethyl)-3-oxo-butyric Acid Methyl Ester (159)

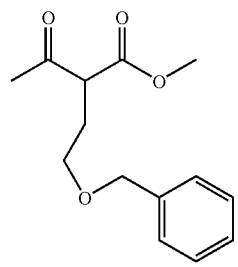

To a suspension of NaH (2.0 g, 60% in mineral oil) in DME (50 ml) at 0° C. is added dropwise a solution of methyl acetoacetate (5.8 g, 50 mmol) in DME (10 mL). The solution is stirred at room temperature for 30 minutes. NaI (7.5 g) is added in one portion and then benzyl bromoethyl ether (10.7 5 g, 50 mmol). The mixture is stirred at 70–80° C. overnight. After the formed solid is removed, the solvent is removed. The residue is purified by column with 4:1 of hexane to ethyl acetate to a colorless oil (159).

Step 2. Preparation of 5-(2-benzyloxy-ethyl)-6-methyl-pyrimidin-4-ol (160)

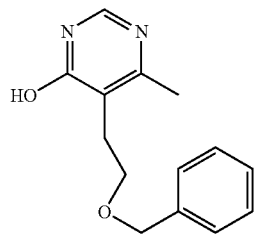

NaOMe (2.75 g, 50 mmol) is added to a stirred solution of formamidine acetate (25 mmol) in MeOH (75 ml) at room temperature. The mixture is stirred for 15 minutes. 2-(2-Benzyloxy-ethyl)-3-oxo-butyric acid methyl ester (20 mmol) is added and the mixture is stirred at room temperature overnight. Acetic acid (1.5 g, 20 mmol) is added and the solvent is removed in vacuo. Water (30 ml) is added to the residue and the mixture is extracted with 2-butanone (3×30 ml). The combined extracts are washed with brine (40 ml), dried (Na$_2$SO$_4$) and evaporated, to provide a yellow solid (160).

Step 3. Preparation of 5-(2-Benzyloxy-ethyl)-4-chloro-6-methyl-pyrimidine (161)

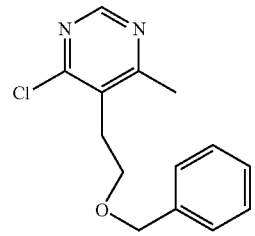

A mixture of 160 (4.1 g, 17 mmol) and POCl$_3$ (10 ml) is heated at 100° C. for 3 hours. The solvent is removed in vacuo and EtOAc (30 ml) and water (30 ml) are added to the residue. NaHCO$_3$ (aq.) is carefully added until the pH of the aqueous layer is greater than 7. The layers are separated and the aqueous layer is extracted with EtOAc (2×30 ml). The combined extracts are washed with brine (50 ml), dried (Na$_2$SO$_4$) and solvent evaporated. Flash column purification of the residue (EtOAc:hexane=1:2) provides the product (161) as a light yellow oil.

Step 4. Preparation of Acetic Acid 2-(4-bromomethyl-6-chloro-pyrimidin-5-yl)-ethyl Ester (162) and 5-(2-benzyloxy-ethyl)-4-bromomethyl-6-chloropyrimidine

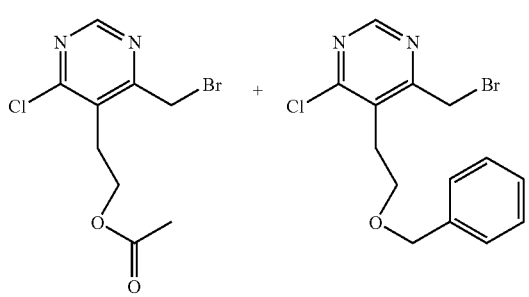

Br$_2$ (1.4 g, 8 mmol) is added drop wise to a stirred solution of 5-(2-benzyloxy-ethyl)-4-chloro-6-methyl-pyrimidine (2.1 g, 8 mmol) in HOAc (20 ml) at 85° C. After addition, the mixture is stirred at 85° C. for an additional 1 hour. The solvent is removed in vacuo and EtOAc (25 ml) and NaHCO$_3$ (25 ml) are added to the residue. The layers are separated and the organic layer is washed with Na$_2$S$_2$O$_3$ solution (sat. 15 ml) followed by brine (20 ml). The organic phase is dried (Na$_2$SO$_4$) and solvent evaporated. The resulting yellow oil is purified by flash column (EtOAc:hexane=6:1) to afford 5-(2-benzyloxy-ethyl)-4-bromomethyl-6-chloro-pyrimidine as a light yellow solid and acetic acid 2-(4-bromomethyl-6-chloro-pyrimidin-5-yl)-ethyl ester (162).

Step 5. Preparation of Acetic Acid 2-{4-chloro-6-[2-(3-fluoro-pyridin-2-yl)-imidazol-1-ylmethyl]-pyrimidin-5-yl}-ethyl ester (163)

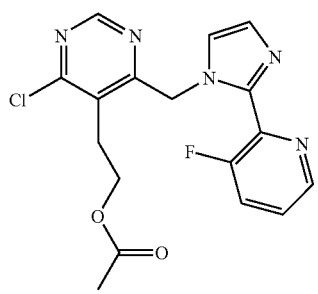

A mixture of 162 (8.4 mmol), 3-fluoro-2-(1H-imidazol-2-yl)-pyridine (described above) (1.38 g, 8.4 mmol) and K$_2$CO$_3$ (1.17 g, 8.4 mmol) in DMF (6 ml) is stirred at room temperature overnight. To the mixture are added EtOAc (20 ml) and water (10 ml). The organic layer is separated and the aqueous layer is extracted with EtOAc (3×10 ml). The combined extracts are washed with brine (10 ml), dried (Na$_2$SO$_4$) and solvent evaporated. PTLC separation of the residue (5% MeOH in CH$_2$Cl$_2$) gives the product (163) as a white solid.

Step 6. Preparation of 2-{4-[2-(3-fluoro-pyridin-2-yl)-imidazol-1-ylmethyl]-6-hydrazino-pyrimidin-5-yl}-ethanol (164)

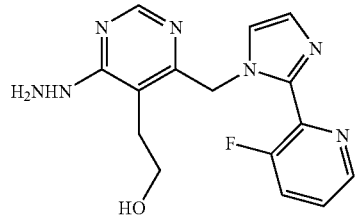

A mixture of 163 (1.72 g, 4.6 mmol) and hydrazine monohydrate (0.95 g, 19 mmol) in EtOH (20 mL) is heated at 70° C. overnight. The solvent is removed in vacuo and the residue is triturated with ethyl acetate and ethyl ether. Filtration gives the product (164) as a white solid.

Step 7. Preparation of 2-{7-[2-(3-fluoro-pyridin-2-yl)-imidazol-1-ylmethyl]-2-methyl-[1,2,4]triazolo[1,5-c]pyrimidin-8-yl}ethanol (165)

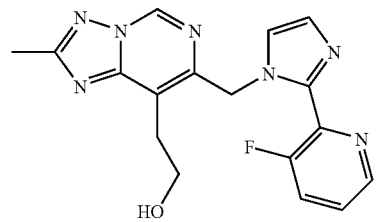

A suspension of 164 in acetic acid (15 mmol) is stirred at 100° C. overnight. Acetic acid is removed in vacuo and to the residue is added NaHCO$_3$ (aq.) (50 mL) and dichloromethane (150 mL). The organic layer is separated and the aqueous layer is extracted with dichloromethane (2×40 mL). The combined organic layers are dried (NaSO$_4$) and solvent is removed. The crude product is stirred with 10% of HCl for one hour. The mixture is neutralized with saturated NaHCO$_3$, extracted with dichloromethane, dried and the solvent is removed. The crude product is separated by column chromatography (5% MeOH in dichloromethane) to give the product (165).

Step 8. Preparation of {7-[2-(3-fluoro-pyridi-2-yl)-imidazol-1-ylmethyl]-2-methyl-[1,2,4]triazolo[1,5-c]pyrimidin-8-yl}-acetaldehyde (166)

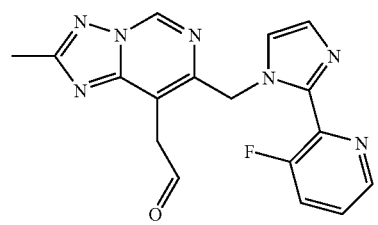

A solution of Dess-Martin (1.56 g, 3.67 mmol) in methylene chloride (8 mL) is added to a solution of 165 (1.3 g, 3.67 mmol) in methylene chloride (10 mL). After two hours, the homogenous reaction mixture is diluted with ether. The mixture is washed with 1.3M NaOH solution and dried (MgSO$_4$). TLC with 5% MeOH/methylene chloride gives the product 166.

Step 9. Preparation of 8-(2,2-difluoro-ethyl)-7-[2-(3-fluoro-pyridin-2-yl)-imidazol-1-ylmethyl]-2-methyl-[1,2,4]triazolo[1,5-c]pyrimidine (158)

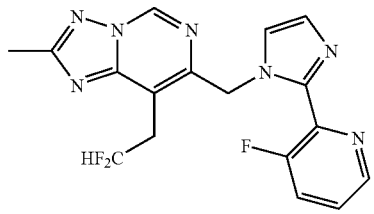

To a solution of 166 (30 mg, 0.085 mmol) in dichloromethane (5 mL) at 0° C. is added bis(2-methoxyethyl)aminosulfur trifluoride (0.5 ml, 50% in THF) under N$_2$. The mixture is heated at 60° C. for two hours and is poured into saturated NaHCO$_3$ (10 mL). After CO$_2$ evolution ceases, the mixture is extracted into dichloromethane, dried (MgSO$_4$), filtered and evaporated in vacuo. PTLC in 5% MeOf/dichloromethane gives the pure title product (158). 1H NMR: 2.59 (3H, s), 1.67 (2H, m), 3.72 (2H, m), 5.88 (2H, s), 6.25 (1H, tt, J=42.3, 3.3 Hz), 7.26–7.3 (3H, m), 7.543 (1H, t, J=6.0 Hz), 8.35 (1H, s), 9.10 (1H, s). LCMS (M+1) 374.07.

G. 2-[1-(8-Propyl-[1,2,4]triazolo[1,5-c]pyrimidin-7-ylmethyl)-1H-imidazol-2-yl]-nicotinonitrile (167)

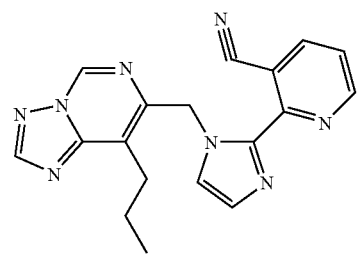

Step 1. Preparation of 7-methyl-8-propyl-[1,2,4]triazolo[1,5-c]pyrimidine (168)

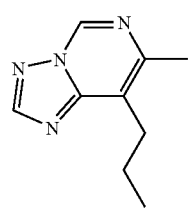

A mixture of 4-chloro-6-methyl-5-propyl-pyrimidine (101) (500 mg, 2.93 mmol) and hydrazine monohydrate (880 mg, 17.6 mmol) in EtOH (15 mL) is heated in a sealed tube at 100° C. overnight. On cooling, the solvent is removed and to the residue is added water (15 mL). The solid is filtered and washed with water (5 mL) and ether (10 mL). The solid is then heated in acetic acid (10 mL) in a sealed tube at 110° C. overnight. The excess acetic acid is removed under vacuum. The residue is neutralized with aqueous sodium bicarbonate and then extracted with ethyl acetate. On drying, the solvent is removed to give the product (168).

Step 2. Preparation 7-bromomethyl-8-propyl-[1,2,4]triazolo[1,5-c]pyrimidine (169)

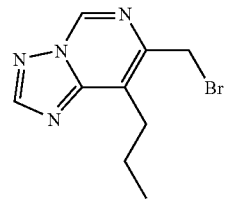

A mixture of 168 (523 mg, 2.75 mmol) and bromine (1.12 g, 7 mmol) in acetic acid (15 mL) is heated in a sealed tube at 110° C. over the weekend. The solvent is removed and the residue is neutralized with aqueous sodium bicarbonate and extracted with ethyl acetate. On drying, the solvent is removed and the crude is purified by PTLC (ethyl acetate: hexanes 1:1) to give the product (169).

Step 3. Preparation of 2-(1H-imidazol-2-yl)-nicotinonitrile (170)

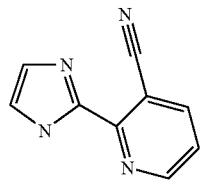

A mixture of 3-bromo-2-(1H-imidazol-2-yl)-pyridine (prepared from 3-bromo-pyridine-2-carbonitrile essentially as described by Clews et al., *Synthesis* (2001):1549) (675 mg, 3 mmol), zinc cyanide (223 mg, 1.9 mmol), Pd$_2$(dba)$_3$ (137 mg, 0.15 mmol), DPPF (160 mg, 0.3 mmol) and water (0.2 mL) in DMF (15 mL) is degassed with argon for 15 minutes. The mixture is then heated at 40° C. overnight in a sealed tube. Solvent is removed, water (30 mL) is added and the mixture is extracted with methylene chloride. On drying (MgSO$_4$), the solvent is removed and the resulting solid is washed with ether (5×10 mL) to give the product (170).

Step 4. Preparation of 2-[1-(8-propyl-[1,2,4]triazolo [1,5-c]pyrimidin-7-ylmethyl)-1H-imidazol-2-yl]-nicotinonitrile (167)

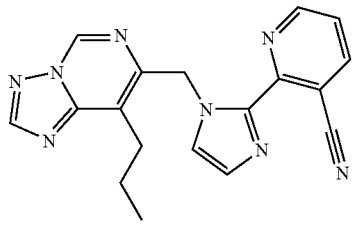

A mixture of 169 (56 mg, 0.22 mmol), 170 (42 mg, 0.25 mmol) and K$_2$CO$_3$ (138 mg) in DMF (4 mL) is stirred at room temperature overnight. Solvent is removed in vacuo. Water (10 mL) is added and the mixture is extracted with ethyl acetate (3×25 mL). The combined organic layers are dried and solvent removed. The crude is purified by PTLC (5% MeOH in methylene chloride) to give the title product (167) as a solid. $^1$H NMR 9.13 (s, 1H), 8.64–8.66 (m, 1H), 8.36 (s, 1H), 8.07–8.10 (m, 1H), 7.29–7.34 (m, 1H), 7.32 (s, 1H), 7.23 (s, 1H), 5.94 (s, 2H), 3.02–3.08 (m, 2H) 1.66–1.74 (m, 2H), 1.00 (t, 3H).

H. 6-[1-(8-Propyl-[1,2,4]triazolo[1,5-c]pyrimidin-7-ylmethyl)-1H-imidazol-2-yl]-pyridine-2-carbonitrile (171)

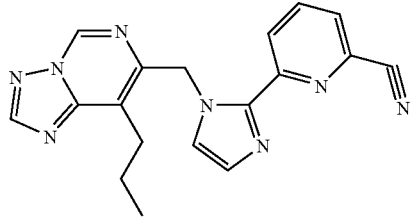

Step 1. Preparation of 6-(1H-imidazol-2-yl)-pyridine-2-carbonitrile (172)

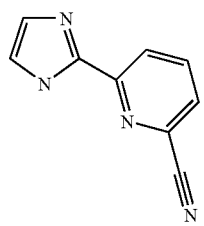

Glyoxal (40% w/w H$_2$O, 20 mL) and ammonium hydroxide (con. 40 mL) are added to a solution of 6-chloro-pyridine-2-carbaldehyde (0.127 mol; prepared from 2-chloro-6-methyl-pyridine essentially as described by Vacher et al. (1998) *J. Med. Chem.* 41:5080) in MeOH (620 mL) at 0° C. The mixture is allowed to warm gradually to room temperature over an 18 hour period. The solvent is removed. Water (125 mL) is added to the residue and the mixture is extracted with methylene chloride (5×150 mL). The combined organic layers are washed with brine (2×100 mL), dried and solvent removed. The crude product is triturated with ethyl ether (200 mL) to give 2-chloro-6-(1H-imidazol-2-yl)-pyridine as a solid.

A mixture of 2-chloro-6-(1H-imidazol-2-yl)-pyridine (800 mg, 4.45 mmol), zinc cyanide (313 mg, 2.68 mmol), Pd$_2$(dba)$_3$ (122 mg, 0.133 mmol), DPPF (144 mg, 0.27 mmol) and water (0.1 mL) in DMF (10 mL) is degassed with argon for 15 minutes. The mixture is then heated at 40° C. overnight in a sealed tube. Solvent is removed and water (30 mL) is added and the mixture is extracted with methylene chloride. On drying (MgSO$_4$), the solvent is removed. Column separation gives the product (172).

Step 2. Preparation of 6-[1-(8-propyl-[1,2,4]triazolo [1,5-c]pyrimidin-7-ylmethyl) -1H-imidazol-2-yl]-pyridine-2-carbonitrile (171)

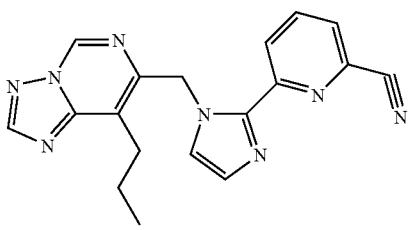

A mixture of 169 (97 mg, 0.38 mmol), 172 (64 mg, 0.38 mmol) and K$_2$CO$_3$ (160 mg) in DMF (4 mL) is stirred at room temperature overnight. Solvent is removed in vacuo. Water (10 mL) is added and the mixture is extracted with ethyl acetate (3×25 mL). The combined organic layers are dried and solvent removed. The crude is purified by PTLC (5% MeOH in methylene chloride) to give the title product (171) as a solid. $^1$H NMR 9.12 (s, 1H), 8.49 (q, 1H), 8.36 (s, 1H), 7.87 (t, 1H), 7.56 (q, 1H), 7.21 (s, 2H), 6.11 (s, 2H), 3.13–3.19 (m, 2H), 1.71–1.79 (m, 2H), 1.02 (t, 3H).

I. 7-{[2-(3-fluoropyridin-2-yl)-1H-imidazol-1-yl]methyl}-8-propyl-2-pyrrolidin-1-yl[1,2,4]triazolo[1, 5-c]pyrimidine (173)

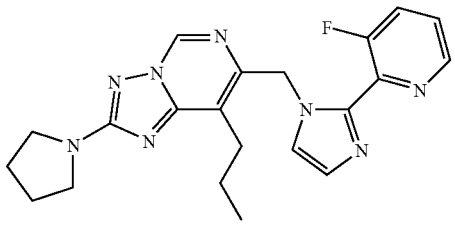

Step 1. Preparation of 7-{[2-(3-fluoropyridin-2-yl)-1H-imidazol-1-yl]methyl}-8-propyl[1,2,4]triazolo[1,5-c]pyrimidin-2-amine (174)

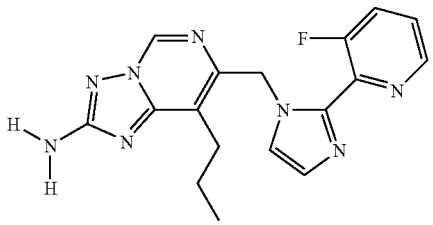

A solution of 131 (2.46 g, 7.52 mmol) and cyanogen bromide (879 mg, 8.3 mmol) in EtOH (18 ml) is refluxed for 4 hours. The solvent is removed in vacuo and the residue is partitioned between saturated aqueous NaHCO$_3$ solution (20 ml) and EtOAc (20 ml). The layers are separated and the aqueous layer is extracted with EtOAc (2×30 ml). The combined extracts are washed with brine (15 ml), dried (Na$_2$SO$_4$) and evaporated. The solid thus obtained is washed with ether (10 ml), which provides a light yellow solid 174.

Step 2. Preparation of 2-bromo-7-[2-(3-fluoro-pyridin-2-yl)-imidazol-1-ylmethyl]-8-propyl-[1,2,4]triazolo[1,5-c]pyrimidine (175)

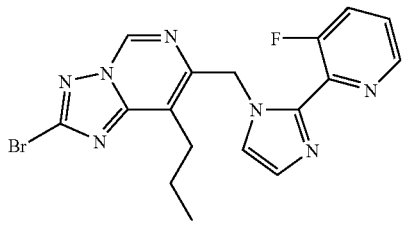

To a solution of 174 (788 mg, 2.24 mmol) in aqueous HBr (48%, 8 ml) cooled to 0° C. is added dropwise a solution of NaNO$_2$ (232 mg, 3.36 mmol) in water (2 ml). The mixture is stirred at 0° C. for 30 minutes and CuBr (482 mg, 3.36 mmol) is added in 3 portions. The mixture is stirred at 0° C. for 30 minutes then allowed to warm to room temperature in 2 hours. Concentrated NH$_4$OH is added dropwise to the solution until the pH≧7. The mixture is then extracted with EtOAc (3×15 ml) and the combined extracts are washed with brine (15 ml), dried (Na$_2$SO$_4$) and evaporated. The brown solid obtained it washed with ether (4 ml) then hexane (6 ml), which gives 175 as a light brown solid.

Step 3. Preparation of 7-{[2-(3-fluoropyridin-2-yl)-1H-imidazol-1-yl]methyl}-8-propyl-2-pyrrolidin-1-yl[1,2,4]triazolo[1,5-c]pyrimidine (173)

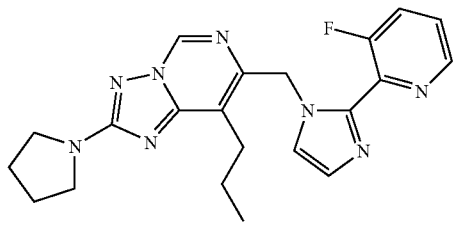

A mixture of 175 (77 mg, 0.185 mmol) and pyrrolidine (0.5 ml) is stirred at room temperature for 4 hours. The solvent is removed in vacuo and the residue is partitioned between water (5 ml) and EtOAc (5 ml). The layers are separated and the aqueous layer is extracted with EtOAc (2×5 ml). The combined extracts are washed with brine (5 ml), dried (Na$_2$SO$_4$) and evaporated. PTLC separation of the residue with 5% MeOH in CH$_2$Cl$_2$ gives the title compound 173 as a white solid. H$^1$ NMR (δ, CDCl$_3$): 8.84 (s, 1H), 8.40 (m, 1H), 7.51–7.56 (m, 1H), 7.21–7.31 (m, 2H), 7.18 (s, 1H), 5.76 (s, 2H), 3.53–3.57 (m, 4H), 2.80–2.84 (m, 2H), 1.99–2.02 (m, 4H), 1.58–1.64 (m, 2H), 0.93 (t, 3H). LC-MS (M+1), 407.10.

J. 7-[2-(3-Fluoro-pyridin-2-yl)-imidazol-1-ylmethyl]-2-isopropoxy-8-propyl-[1,2,4]-triazolo[1,5-c]pyrimidine (176)

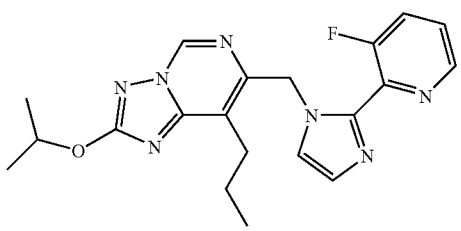

Step 1. Preparation of 7-[2-(3-fluoro-pyridin-2-yl)-imidazol-1-ylmethyl]-8-propyl-[1,2,4]triazolo[1,5-c]pyrimidin-2-ol (177)

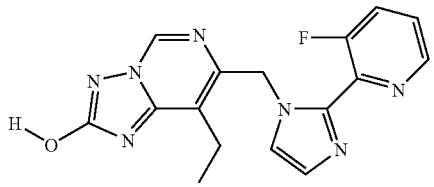

To the solution of 131 (3.27, 10 mmol) in anhydrous NMP (3.6 mL) under nitrogen is added urea (1.60 g, 26 mmol). The resulting mixture is heated to 160° C. and stirred for 6 hours. On cooling, the reaction mixture is poured into water (80 mL), pH is adjusted to 7 with hydrochloric acid, and the solution is extracted with dichloromethane (50 ml×4). The organic solution is dried with anhydrous sodium sulfate and concentrated to give the crude product 177 as an oil which is used directly in the next step reaction.

Step 2. Preparation of 7-[2-(3-fluoro-pyridin-2-yl)-imidazol-1-ylmethyl]-2-isopropoxy-8-propyl-[1,2,4]-triazolo[1,5-c]pyrimidine (176)

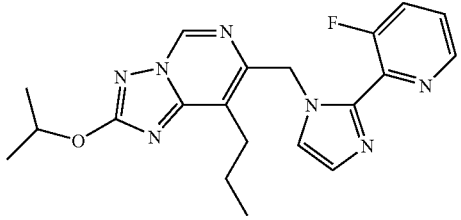

To the solution of compound 177 in DMF (10 mL) is added anhydrous potassium carbonate (2 eq.) and 2-iodopropane (2 eq.). The resulting mixture is stirred at 60° C.

overnight. On cooling the reaction mixture is poured into water (50 mL) and the mixture extracted with dichloromethane, dried over sodium sulfate. The organic solution is concentrated and purified with PTLC to give product 176 as sticky oil. LCMS (M+1) 396.3.

K. Synthesis of Additional[1,2,4]triazolo[1,5-c]pyrimidines

The compounds shown in Table 3 are synthesized as illustrated above.

TABLE 3

| | Compound | Name | LC-MS (M + 1) |
|---|---|---|---|
| 178 | | 7-{[2-(5-fluoropyridin-2-yl)-1H-imidazol-1-yl]methyl}-2-methyl-8-propyl[1,2,4]triazolo[1,5-c]pyrimidine | 352.34 |
| 179 | | 3-{1-[(8-ethyl[1,2,4]triazolo[1,5-c]pyrimidin-7-yl)methyl]-1H-imidazol-2-yl}benzonitrile | 330.37 |
| 180 | | 8-ethyl-7-{[2-(5-fluoro-2-methoxyphenyl)-1H-imidazol-1-yl]methyl}[1,2,4]triazolo[1,5-c]pyrimidine | 353.36 |
| 181 | | 8-ethyl-7-{[2-(3-fluorophenyl)-1H-imidazol-1-yl]methyl}[1,2,4]triazolo[1,5-c]pyrimidine | 323.35 |
| 182 | | 7-{[2-(6-chloropyridin-2-yl)-1H-imidazol-1-yl]methyl}-8-ethyl[1,2,4]triazolo[1,5-c]pyrimidine | 340.33 |
| 183 | | 7-{[2-(2-chlorophenyl)-1H-imidazol-1-yl]methyl}-8-ethyl[1,2,4]triazolo[1,5-c]pyrimidine | 339.33 |

TABLE 3-continued

| Compound | | Name | LC-MS (M + 1) |
|---|---|---|---|
| 184 | (structure) | 7-{[2-(3-fluoropyridin-2-yl)-1H-imidazol-1-yl]methyl}-8-propyl[1,2,4]triazolo[1,5-c]pyrimidine-2-carboxylic acid | 382.34 |
| 185 | (structure) | 6-{1-[(8-ethyl[1,2,4]triazolo[1,5-c]pyrimidin-7-yl)methyl]-1H-imidazol-2-yl}pyridine-2-carbonitrile | 331.37 |

Example 3 synthesis of [1,2,4]triazolo[4,3C]pyrimidines

A. 7-[2-(3-fluoro-pyridin-2-yl)-imidazol-1-yl-methyl]-3-methyl-8-propyl-[1,2,4]triazolo[4,3-c]pyrimidine (186)

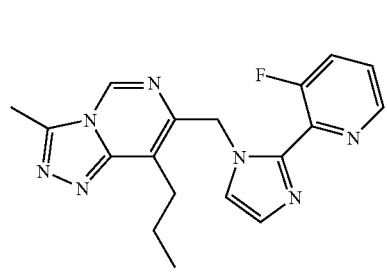

A suspension of 131 (620 mg, 0.7 mmol) and acetic anhydride (2 mL) is stirred at 110° C. for one hour. NaHCO₃ (aq.) (10 mL) and dichloromethane (10 mL) are added. The organic layer is separated and the aqueous layer is extracted with dichloromethane (2×10 mL). The combined organic layers are dried (NaSO₄) and solvent removed. The crude product is separated by PTLC (5% methanol in dichloromethane) to yield 186; LC-MS, M+1 352.18; ¹H-NMR (CDCl₃) δ: 8.59 (s, 1H), 8.42 (d, 1H), 7.54 (t, 1H), 7.23–7.35 (m, 2H), 7.21 (s, 1H), 5.77 (s, 2H), 2.98 (t, 2H), 2.78 (s, 3H), 1.62–1.74 (m, 2H), 0.97 (t, 3H).

B. 7-[2-(3-Fluoro-pyridin-2-YL)-imidazol-1-ylmethyl]-8-propyl-[1,2,4]triazolo[4,3-c]-pyrimidine (187)

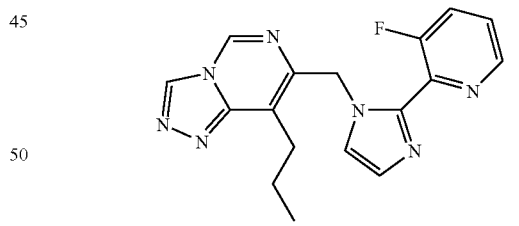

A suspension of 131 (30 mg, 0.09 mmol) and diethoxymethyl acetate (1 mL) is stirred at room temperature for 10 minutes. NaHCO₃ (aq.) (10 mL) and dichloromethane (10 mL) are added. The organic layer is separated and the aqueous layer is extracted with dichloromethane (2×10 mL). The combined organic layers are dried (NaSO₄) and solvent removed. The crude product is separated by PTLC (10% methanol in dichloromethane) to yield 187; LC-MS, M+1 338.15; ¹H-NMR (CDCl₃) δ: 8.87 (s, 1H), 8.83 (s, 1H), 8.42 (s, 1H), 7.54 (t, 1H), 7.23–7.34 (m, 3H), 5.79 (s, 2H), 3.02 (t, 2H), 1.66–1.76 (m, 2H), 0.99 (t, 3H).

C. 7-[2-(3-Fluoro-pyridin-2-YL)-imidazol-1-ylm-ethyl]-3-phenyl-8-propyl-[1,2,4]-triazolo[4,3-c]pyrimidine (188)

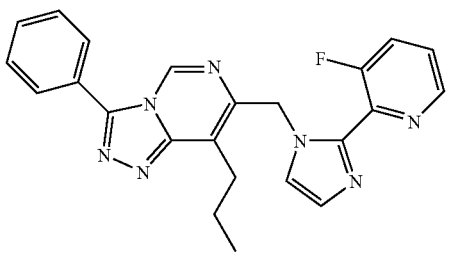

A suspension of 131 (0.5 g, 1.5 mmol) and trimethyl orthobenzioate (2 mL) is stirred at 110° C. for 2 hours. NaHCO₃ (aq.) (10 mL) and dichloromethane (10 mL) are added. The organic layer is separated and the aqueous layer is extracted with dichloromethane (2×10 mL). The combined organic layers are dried (NaSO₄) and solvent removed. The crude product is separated by PTLC (2.1 acetone:ethyl acetate) to yield 188; LC-MS, M+1 414.15; ¹H-NMR (CDCl₃) δ: 8.93 (s, 1H), 8.42 (d, 1H), 7.79–7.81 (m, 2H), 7.52–7.59 (m, 4H), 7.23–7.34 (m, 3H), 5.82 (s, 2H), 3.06 (t, 2H), 1.70–1.80 (m, 2H), 1.02 (t, 3H).

D. 3-Difluoromethyl-7-[2-(3-fluoro-pyridin-2-yl)-imidazol-1-ylmethyl]-8-propyl-[1,2,4]triazolo[4,3C]pyrimidine (189)

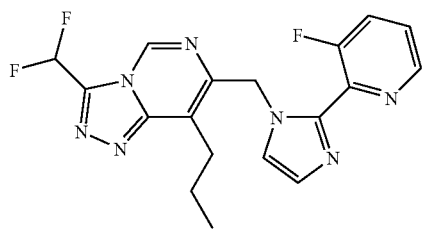

A suspension of 131 (230 mg, 0.7 mmol) and difluoroacetic anhydride (2 mL) is stirred at 50° C. for one hour. NaHCO₃ (aq.) (10 mL) and dichloromethane (10 mL) are added. The organic layer is separated and the aqueous layer is extracted with dichloromethane (2×10 mL). The combined organic layers are dried (NaSO₄) and solvent removed. The crude product is separated by PTLC (12:1 ethyl acetate:acetone) to yield 189; LC-MS, M+1 388.13; ¹H-NMR (CDCl₃) δ: 8.95 (s, 1H), 8.34 (d, 1H), 7.51 (t 1H), 7.02–7.37 (m, 4H), 5.81 (s. 2H), 3.01 (t, 2H), 1.62–1.73 (m, 21H), 0.96 (t, 3H).

E. 8-Ethyl-7-[2-(3-trifluoromethyl-phenyl)-imidazol-1-ylmethyl]-[1,2,4]triazolo[4,3-c]pyrimidine (190) is synthesized as illustrated above. LC-MS (M+1) 373.34.

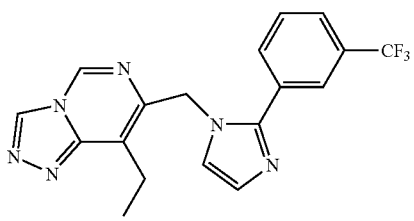

F. Synthesis of Additional [1,2,4]triazolo[4,3C]pyrimidines

The compounds shown in Table 4 are synthesized as illustrated above, and as exemplified in Examples 3A–D.

TABLE 4

| Compound | | Structure |
|---|---|---|
| 191 | 7-[2-(6-Fluoro-pyridin-2-yl)-imidazol-1-ylmethyl]-3-methyl-8-propyl-[1,2,4]triazolo[4,3-c]-pyrimidine | |
| 192 | 7-[2-(6-Fluoro-pyridin-2-yl)-imidazol-1-ylmethyl]-8-propyl-[1,2,4]triazolo[4,3-c]pyrimidine | |

TABLE 4-continued

| Compound | Structure |
|---|---|
| 193 7-[2-(3-Fluoro-pyridin-2-yl)-imidazol-1-ylmethyl]-8-propyl-[1,2,4]triazolo[4,3-c]pyrimidine | 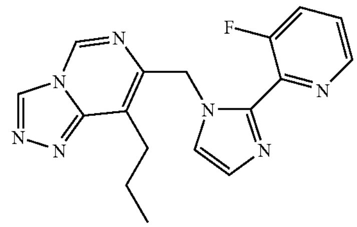 |
| 194 1-{7-[2-(3-Fluoro-pyridin-2-yl)-imidazol-1-ylmethyl]-8-propyl-[1,2,4]triazolo[4,3-c]pyrimidin-3-yl}-ethanol | 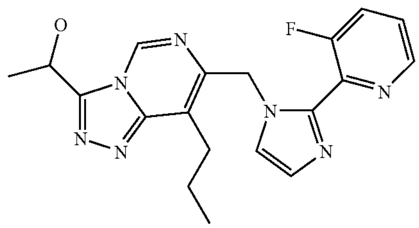 |
| 195 7-[2-(3-Fluoro-pyridin-2-yl)-imidazol-1-ylmethyl]-8-propyl-3-trifluoromethyl-[1,2,4]triazolo[4,3-c]pyrimidine | 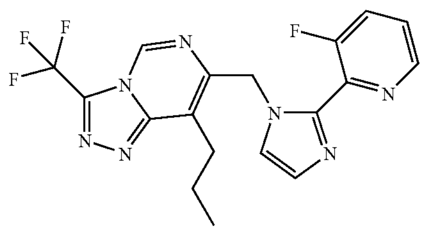 |
| 196 7-[2-(3-Fluoro-pyridin-2-yl)-imidazol-1-ylmethyl]-3-methoxy-methyl-8-propyl-[1,2,4]triazolo[4,3-c]pyrimidine | 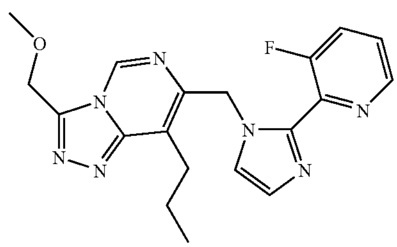 |
| 197 7-[2-(6-Fluoro-pyridin-2-yl)-imidazol-1-ylmethyl]-3-methoxymethyl-8-propyl-[1,2,4]triazolo[4,3-c]pyrimidine | 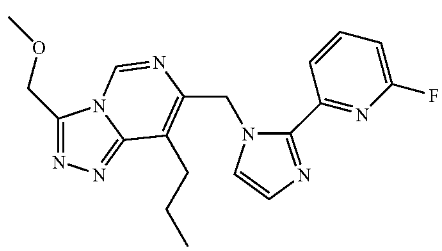 |
| 198 3-Cyclobutyl-7-[2-(6-fluoro-pyridin-2-yl)-imidazol-1-ylmethyl]-8-propyl-[1,2,4]triazolo[4,3-c]pyrimidine | 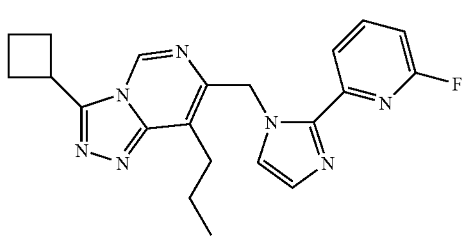 |

TABLE 4-continued

| Compound | Structure |
|---|---|
| 199 8-Propyl-7-(2-pyridin-2-yl-imidazol-1-ylmethyl)-[1,2,4]-triazolo[4,3-c]pyrimidine | 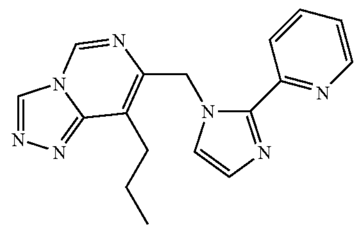 |
| 200 7-[2-(2,5-Difluoro-phenyl)-imidazol-1-ylmethyl]-3-methyl-8-propyl-[1,2,4]triazolo[4,3-c]pyrimidine | 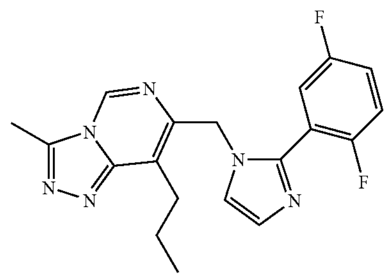 |
| 201 7-[2-(6-Methoxy-pyridin-2-yl)-imidazol-1-ylmethyl]-8-propyl-[1,2,4]triazolo[4,3-c]pyrimidine | 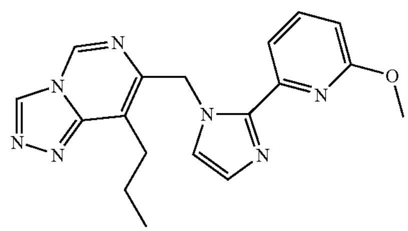 |
| 202 3-Methyl-8-propyl-7-(2-thiazol-2-yl-imidazol-1-ylmethyl)-[1,2,4]triazolo[4,3-c]pyrimidine | 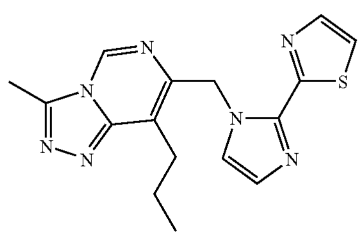 |
| 203 3-Methyl-8-propyl-7-(2-pyridin-2-yl-imidazol-1-ylmethyl)-[1,2,4]triazolo[4,3-c]pyrimidine | 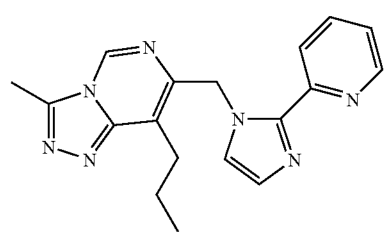 |
| 204 6-[1-(8-Propyl-[1,2,4]triazolo[4,3-c]pyrimidin-7-ylmethyl)-1H-imidazol-2-yl]-pyridin-2-ol | 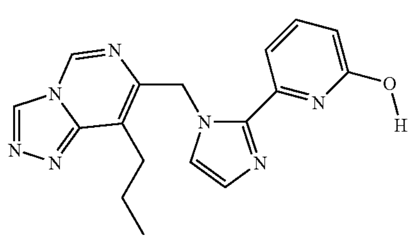 |

TABLE 4-continued

| Compound | Structure |
|---|---|
| 205 7-[2-(2,6-Difluoro-phenyl)-imidazol-1-ylmethyl]-8-propyl-[1,2,4]triazolo[4,3-c]pyrimidine | 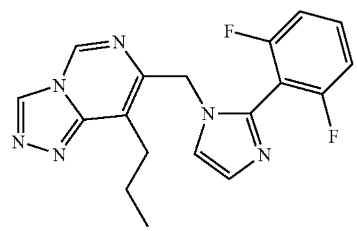 |
| 206 8-Propyl-7-(2-thiophen-2-yl-imidazol-1-ylmethyl)-[1,2,4]-triazolo[4,3-c]pyrimidine | 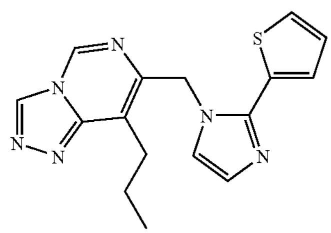 |
| 207 3-Methyl-8-propyl-7-(2-pyridazin-3-yl-imidazol-1-ylmethyl)-[1,2,4]triazolo[4,3-c]pyrimidine | 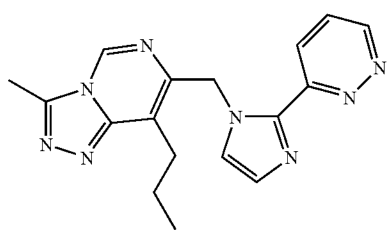 |
| 208 7-[2-(2,5-Difluoro-phenyl)-imidazol-1-ylmethyl]-8-ethyl-[1,2,4]triazolo[4,3-c]pyrimidine | 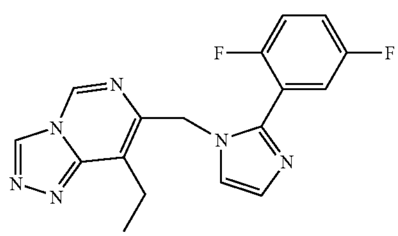 |
| 209 7-[2-(2,5-difluoro-phenyl)-imidazol-1-ylmethyl]-8-ethyl-3-methyl-[1,2,4]triazolo[4,3-c]pyrimidine | 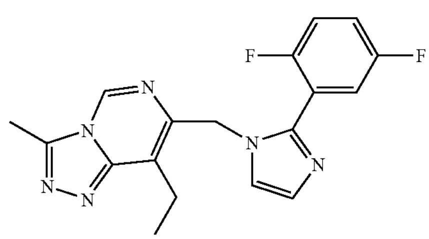 |
| 210 8-Ethyl-7-[2-(5-fluoro-2-methyl-phenyl)-imidazol-1-ylmethyl]-[1,2,4]triazolo[4,3-c]pyrimidine | 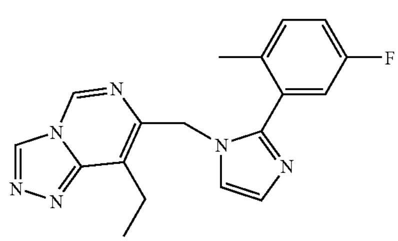 |

TABLE 4-continued

| Compound | Structure |
|---|---|
| 211 8-Ethyl-7-[2-(5-fluoro-2-methyl-phenyl)-imidazol-1-yl-methyl]-3-methyl-[1,2,4]triazolo[4,3-c]pyrimidine | 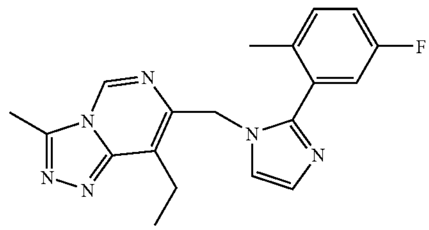 |
| 212 3-Ethyl-7-[2-(3-fluoro-pyridin-2-yl)-imidazol-1-ylmethyl]-8-propyl-[1,2,4]triazolo[4,3-c]pyrimidine | 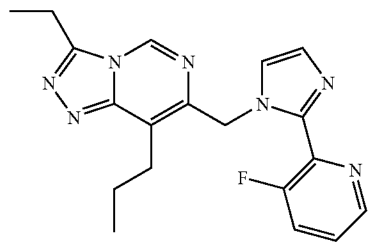 |

Example 4

Synthesis of imidazo[1,5-c]pyrimidines

A. 7-[2-(6-fluoro-pyridin-2-yl)-imidazol-1-ylmethyl]-1-methyl-8-propyl-imidazo[1,5-c]pyrimidine (213)

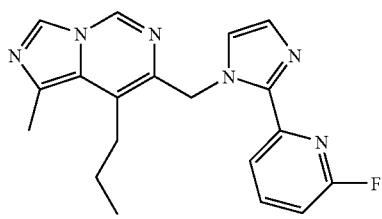

Step 1. Preparation of 1-{6-[2-(6-fluoro-pyridin-2-yl)-imidazol-1-ylmethyl]-5-propyl-pyrimidin-4-yl}-ethanone (214)

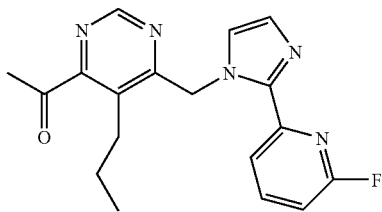

Tributyltinvinylethylether (0.27 g) and Pd(Ph₃P)₂Cl₂ (30 mg) are added to a solution of 4-chloro-6-[2-(6-fluoro-pyridin-2-yl)-imidazol-1-ylmethyl]-5-propyl-pyrimidine (103) (0.168 g) in toluene (30 mL). The mixture is degassed for 10 minutes, and then heated at 110° C. overnight. The solvent is removed under vacuum to obtain crude product. LC-MS: (M+1) 368.13. The above crude product is dissolved in MeOH (15 mL). 6N of HCl (10 mL) is added and the mixture is stirred at room temperature for 3 hours. The solvent is removed, neutralized with saturated NaHCO₃, and extracted with ethyl acetate. The combined organic layers are dried, solvent removed to give crude product, which is purified by TLC with 5% MeOH in dichloromethane to give the product (214). $^1$H NMR δ (CDCL₃) 1.01 (t, 3H, J=7.5 Hz), 1.67 (p, 2H, J=7.2 Hz), 2.66 (s, 3H), 2.94 (t, 2H, J=7.5 Hz), 6.05 (s, 2H), 6.74 (dd, 1H, J=6.0, 2.7 Hz), 7.10 (s, 1H), 7.25 (s, 1H), 7.83 (q, 1H, J=6.0 Hz), 8.13 (d, 1H, J=6.0 Hz), 8.90 (s, 1H). LC-MS: (M+1) 340.14.

Step 2. Preparation, of N-(1-{6-[2-(6-fluoro-pyridin-2-yl)-imidazol-1-ylmethyl]-5-propyl-pyrimidin-4-yl}-ethyl)-formamide (215)

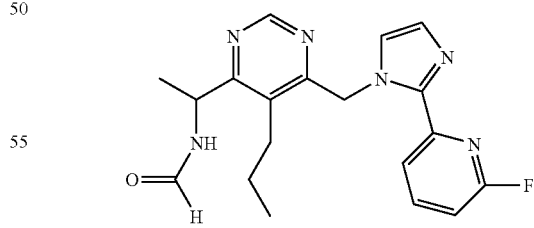

214 (0.1 g) and formic acid (0.1 mL) are added to 2 mL of formamide at 160–180° C. The mixture is heated at 160–180° C. for an additional 3 hours. During this period, additional formic acid (0.2 mL) is added. The mixture is cooled to room temperature and poured into water (10 mL). The solution is made alkaline to at least pH 11 with concentrated sodium hydroxide. The solution is extracted with ethyl acetate. The combined organic layers are dried over MgSO₄, and the solvent is removed to give the crude product. PTLC separation with 10% MeOH in methylene chloride gives the title product (215). ¹H NMR δ (CDCL₃) 1.06 (t, 3H, J=7.5 Hz), 1.43 (d, 3H, J=5.1 Hz), 1.55 –1.72 (m, 2H), 2.72–2.80 (m, 1H), 2.86–2.95 (m, 1H), 5.52 (p, 1H, J=5.4 Hz), 5.81 (d, 1H, J=12.3 Hz), 6.08 (d, 1H, J=12.3 Hz), 6.73 (dd, 1 H, J=6, 2.1 Hz)), 6.99 (d, 1H, J=5.7 Hz), 7.12 (d, 1H, J=2.7 Hz), 7.23 (d, 1H, J=2.7 Hz), 7.78 (q, 1H, J=6.0 Hz), 8.12 (dd, 1H, J=6.0, 2.1 Hz), 8.18 (s, 1H), 8.79 (s, 1H). LC-MS: (M+1) 369.13.

Step 3. Preparation of 7-[2-(6-fluoro-pyridin-2-yl)-imidazol-1-ylmethyl]-1-methyl-8-propyl-imidazo[1,5-c]pyrimidine (213)

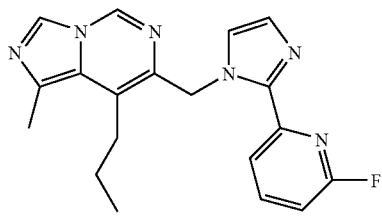

A mixture of 215 (20 mg) and POCl₃ (2 ml) is heated at reflux for 3 hours. The excess of POCl₃ is removed. Ethyl acetate (10 mL) is added, and the mixture is washed with saturated NaHCO₃ (5 mL), brine (5 mL), and dried over MgSO₄. After evaporation of the solvent, the residue is purified by PTLC with 5% MeOH in dichloromethane to give the title product (213). ¹H NMR δ (CDCL₃) 0.99 (t, 3H, J=7.5 Hz), 1.55 (p, 2H, J=7.2 Hz), 2.62 (s, 3H), 2.92 (t, 2H, J=7.5 Hz), 5.92 (s, 2H), 6.87 (dd, 1H, J=8.1, 3 Hz), 7.15 (s, 1H), 7.22 (s, 1H), 7.85 (q, 1H, J=8.1 Hz), 8.06 (s, 1H), 8.14 (d, 1H, J=8.1 Hz), 8.57 (s, 1H). LC-MS: (M+1) 351.12.

B. 7-[2-(3-fluoro-pyridin-2-yl)-imidazol-1-ylm-ethyl]-1-methyl-8-propyl-imidazo[1,5-c]pyrimidine (216)

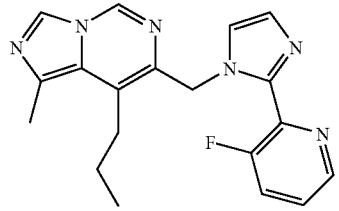

¹H NMR δ (CDCl₃) 0.94 (t, 3H, J=7.5 Hz), 1.48 (p, 2H, J=7.2 Hz), 2.58 (s, 3H), 2.72 (t, 2H, J=7.5 Hz), 5.61 (s, 2H), 7.18 (d, 1H, J=2.7 Hz), 7.20 (s, 1H), 7.33 (m, 1H), 7.55 (t, 1H, J=9.6 Hz), 8.05 (s, 1H), 8.47 (d, 1H, J=4.5 Hz), 8.54 (s, 1H). LC-MS: (M+1) 351.14.

Example 5

Additional Imidazopyrimidines and Triazolopyrimidines

The compounds shown in Tables 5 and 6, below, are synthesized via the methods illustrated in the above Schemes and the previous Examples. In some cases, additional steps of functional group transformation well known to those or ordinary skill in the art are employed to produce the compounds. An asterisk in the column titled "$K_i$" indicates that the compound exhibits a $K_i$ of less than 1 micromolar in the ligand binding assay provided in Example 6. Compounds 213 and 216, above, also exhibit a $K_i$ value of less than 1 micromolar. LCMS data, where indicated, was obtained as described above and is given as M+1.

TABLE 5

| | Compound | Name | $K_i$ | LCMS |
|---|---|---|---|---|
| 217 | | 7-[2-(6-Fluoro-pyridin-2-yl)-imidazol-1-ylmethyl]-2,5-dimethyl-8-propyl-[1,2,4]triazolo[1,5-c]pyrimidine | * | 366.27 |
| 218 | | 2-Ethyl-7-[2-(6-fluoro-pyridin-2-yl)-imidazol-1-ylmethyl]-5-methyl-8-propyl-[1,2,4]triazolo[1,5-c]pyrimidine | * | 380.29 |

TABLE 5-continued

| | Compound | Name | $K_i$ | LCMS |
|---|---|---|---|---|
| 219 | | 2,8-Diethyl-7-[2-(5-fluoro-2-methyl-phenyl)-imidazol-1-ylmethyl]-[1,2,4]triazolo[1,5-c]pyrimidine | * | 364.18 |
| 220 | | 7-[2-(3-Fluoro-pyridin-2-yl)-imidazol-1-ylmethyl]-8-methoxymethyl-2-methyl-[1,2,4]triazolo[1,5-c]pyrimidine | * | 354.14 |
| 221 | | 1-{7-[2-(6-Fluoro-pyridin-2-yl)-imidazol-1-ylmethyl]-2-methyl-[1,2,4]triazolo[1,5-c]pyrimidin-8-yl}-propan-1-ol | * | 368.16 |
| 222 | | 1-{7-[2-(3-Fluoro-pyridin-2-yl)-imidazol-1-ylmethyl]-2-methyl-[1,2,4]triazolo[1,5-c]pyrimidin-8-yl}-propan-1-ol | * | 368.16 |
| 223 | | {7-[2-(3-Fluoro-pyridin-2-yl)-imidazol-1-ylmethyl]-8-propyl-[1,2,4]triazolo[1,5-c]pyrimidin-2-yl}-methanol | * | 368.16 |
| 224 | | 7-[2-(3-Fluoro-pyridin-2-yl)-imidazol-1-ylmethyl]-2-methyl-8-propenyl-[1,2,4]triazolo[1,5-c]pyrimidine | * | 350.15 |

TABLE 5-continued

| | Compound | Name | $K_i$ | LCMS |
|---|---|---|---|---|
| 225 | | 7-[2-(3-Fluoro-pyridin-2-yl)-imidazol-1-ylmethyl]-8-propyl-2-pyridin-3-yl-[1,2,4]triazolo[1,5-c]pyrimidine | * | 415.22 |
| 226 | | 8-(3-Benzyloxy-propyl)-7-[2-(3-fluoro-pyridin-2-yl)-imidazol-1-ylmethyl]-2-methyl[1,2,4]triazolo[1,5-c]pyrimidine | * | 458.27 |
| 227 | | 8-(2-Benzyloxy-ethyl)-7-[2-(3-fluoro-pyridin-2-yl)-imidazol-1-ylmethyl]-2-methyl-[1,2,4]triazolo[1,5-c]pyrimidine | * | 444.25 |
| 228 | | 3-{7-[2-(3-Fluoro-pyridin-2-yl)-imidazol-1-ylmethyl]-2-methyl-[1,2,4]triazolo[1,5-c]pyrimidin-8-yl}-propan-1-ol | * | 368.17 |
| 229 | | 8-(2-Fluoro-ethyl)-7-[2-(3-fluoro-pyridin-2-yl)-imidazol-1-ylmethyl]-2-methyl-[1,2,4]triazolo[1,5-c]pyrimidine | * | 356.14 |

TABLE 5-continued

| Compound | Name | $K_i$ | LCMS |
|---|---|---|---|
| 230 | 8-(3-Chloro-propyl)-7-[2-(3-fluoro-pyridin-2-yl)-imidazol-1-ylmethyl]-2-methyl-[1,2,4]triazolo[1,5-c]pyrimidine | * | 386.83 |
| 231 | 2-{7-[2-(3-Fluoro-pyridin-2-yl)-imidazol-1-ylmethyl]-2-methyl-[1,2,4]triazolo[1,5-c]pyrimidin-8-yl}-ethanol | * | 354.14 |
| 232 | 8-(3-Fluoro-propyl)-7-[2-(3-fluoro-pyridin-2-yl)-imidazol-1-ylmethyl]-2-methyl-[1,2,4]triazolo[1,5-c]pyrimidine | * | 370.17 |
| 233 | 8-(3-Fluoro-propyl)-7-[2-(3-fluoro-pyridin-2-yl)-imidazol-1-ylmethyl]-[1,2,4]triazolo[1,5-c]pyrimidine | * | 356.15 |
| 234 | 8-ethyl-7-{[2-(3-fluoropyridin-2-yl)-1H-imidazol-1-yl]methyl}[1,2,4]triazolo[1,5-c]pyrimidine | * | 324.22 |
| 235 | 8-Propyl-7-[2-(6-trifluoromethyl-pyridin-2-yl)-imidazol-1-ylmethyl]-[1,2,4]triazolo[1,5-c]pyrimidine | * | 388.18 |

TABLE 5-continued

| | Compound | Name | $K_i$ | LCMS |
|---|---|---|---|---|
| 236 | 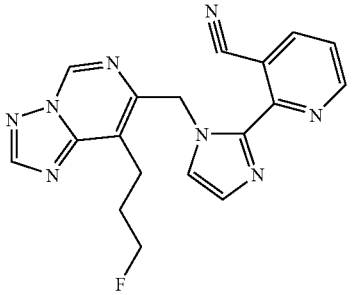 | 2-{1-[8-(3-Fluoro-propyl)-[1,2,4]triazolo[1,5-c]pyrimidin-7-ylmethyl]-1H-imidazol-2-yl}-nicotinonitrile | * | 363.17 |
| 237 | 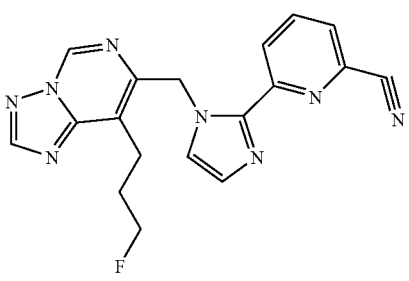 | 6-{1-[8-(3-Fluoro-propyl)-[1,2,4]triazolo[1,5-c]pyrimidin-7-ylmethyl]-1H-imidazol-2-yl}-pyridine-2-carbonitrile | * | 363.17 |
| 238 | 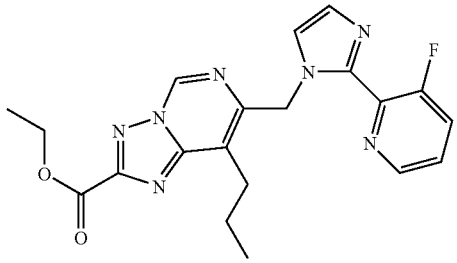 | 7-[2-(3-Fluoro-pyridin-2-yl)-imidazol-1-ylmethyl]-8-propyl-[1,2,4]triazolo[1,5-c]pyrimidine-2-carboxylic acid ethyl ester | * | 410.4 |
| 239 | 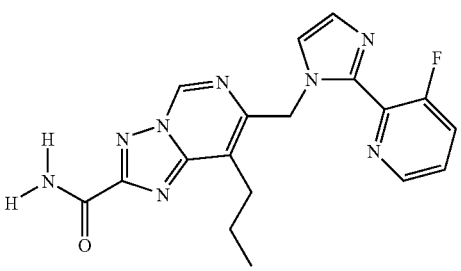 | 7-[2-(3-Fluoro-pyridin-2-yl)-imidazol-1-ylmethyl]-8-propyl-[1,2,4]triazolo[1,5-c]pyrimidine-2-carboxylic acid amide | * | 381.3 |
| 240 | 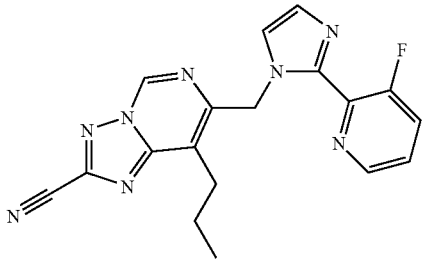 | 7-[2-(3-Fluoro-pyridin-2-yl)-imidazol-1-ylmethyl]-8-propyl-[1,2,4]triazolo[1,5-c]pyrimidine-2-carbonitrile | * | 363.12 |

TABLE 5-continued

| | Compound | Name | $K_i$ | LCMS |
|---|---|---|---|---|
| 241 | | 7-[4-Chloro-2-(3-fluoro-pyridin-2-yl)-imidazol-1-ylmethyl]-8-propyl-[1,2,4]triazolo[1,5-c]pyrimidine | * | 372.14 |
| 242 | | 2-[1-(2-methyl-8-propyl-[1,2,4]triazolo[1,5-c]pyrimidin-7-ylmethyl)-1H-imidazol-2-yl]-nicotinonitrile | * | 359.4 |
| 243 | | 8-Ethoxy-7-[2-(3-fluoro-pyridin-2-yl)-imidazol-1-ylmethyl]-2-methyl-[1,2,4]triazolo[1,5-c]pyrimidine | * | 354.24 |
| 244 | | 8-ethyl-7-{[2-(3-fluoropyridin-2-yl)-1H-imidazol-1-yl]methyl}-2-methyl[1,2,4]triazolo[1,5-c]pyrimidine | * | 338.23 |
| 245 | | 8-ethoxy-7-{[2-(3-fluoropyridin-2-yl)-1H-imidazol-1-yl]methyl}[1,2,4]triazolo[1,5-c]pyrimidine | * | 340.20 |
| 246 | | 7-{[2-(3-fluoropyridin-2-yl)-1H-imidazol-1-yl]methyl}-2-methoxy-8-propyl[1,2,4]triazolo[1,5-c]pyrimidine | * | 368.26 |

TABLE 5-continued

| | Compound | Name | K$_i$ | LCMS |
|---|---|---|---|---|
| 247 | | 2-ethoxy-7-{[2-(3-fluoropyridin-2-yl)-1H-imidazol-1-yl]methyl}-8-propyl[1,2,4]triazolo[1,5-c]pyrimidine | * | 382.28 |
| 248 | | 7-{[2-(3-fluoropyridin-2-yl)-1H-imidazol-1-yl]methyl}-8-propyl[1,2,4]triazolo[1,5-c]pyrimidin-2-amine | * | 353.19 |
| 249 | | 2-(7-{[2-(3-fluoropyridin-2-yl)-1H-imidazol-1-yl]methyl}-8-propyl[1,2,4]triazolo[1,5-c]pyrimidin-2-yl)propan-2-ol | * | 396.22 |
| 250 | | 2-(ethoxymethyl)-7-{[2-(6-fluoropyridin-2-yl)-1H-imidazol-1-yl]methyl}-8-propyl[1,2,4]triazolo[1,5-c]pyrimidine | * | 396.22 |
| 251 | | methyl 7-{[2-(3-fluoropyridin-2-yl)-1H-imidazol-1-yl]methyl}-8-propyl[1,2,4]triazolo[1,5-c]pyrimidine-2-carboxylate | * | 396.19 |
| 252 | | 2-(7-{[2-(6-fluoropyridin-2-yl)-1H-imidazol-1-yl]methyl}-8-propyl[1,2,4]triazolo[1,5-c]pyrimidin-2-yl)propan-2-ol | * | 396.22 |

TABLE 5-continued

| | Compound | Name | $K_i$ | LCMS |
|---|---|---|---|---|
| 253 | 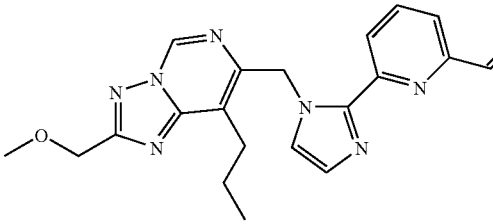 | 6-(1-{[2-(methoxymethyl)-8-propyl[1,2,4]triazolo[1,5-c]pyrimidin-7-yl]methyl}-1H-imidazol-2-yl)pyridine-2-carbonitrile | * | 389.21 |
| 254 | 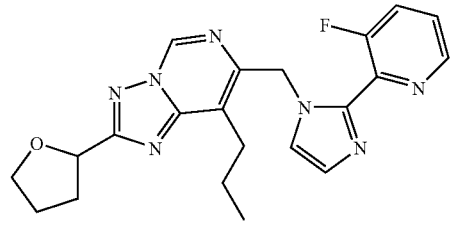 | 7-{[2-(3-fluoropyridin-2-yl)-1H-imidazol-1-yl]methyl}-8-propyl-2-(tetrahydrofuran-2-yl)[1,2,4]triazolo[1,5-c]pyrimidine | * | 408.21 |
| 255 | 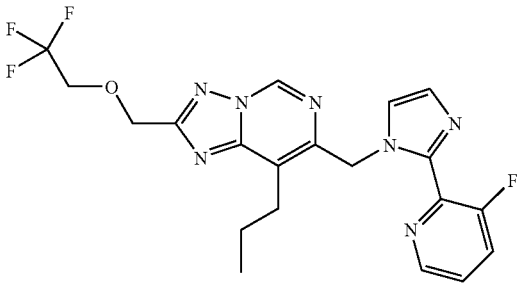 | 7-{[2-(3-fluoropyridin-2-yl)-1H-imidazol-1-yl]methyl}-8-propyl-2-[(2,2,2-trifluoroethoxy)methyl][1,2,4]triazolo[1,5-c]pyrimidine | * | 450.23 |
| 256 | 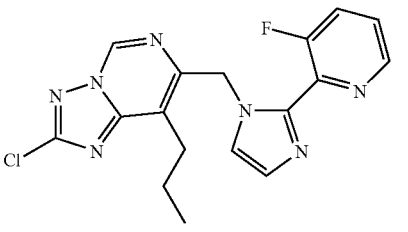 | 2-chloro-7-{[2-(3-fluoropyridin-2-yl)-1H-imidazol-1-yl]methyl}-8-propyl[1,2,4]triazolo[1,5-c]pyrimidine | * | 372.14 |
| 257 | 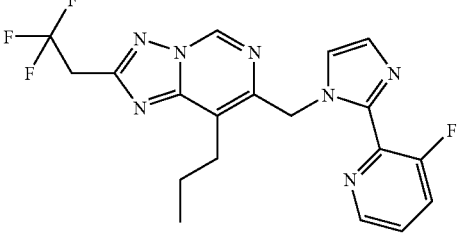 | 7-{[2-(3-fluoropyridin-2-yl)-1H-imidazol-1-yl]methyl}-8-propyl-2-(2,2,2-trifluoroethyl)[1,2,4]triazolo[1,5-c]pyrimidine | * | 420.18 |
| 258 | 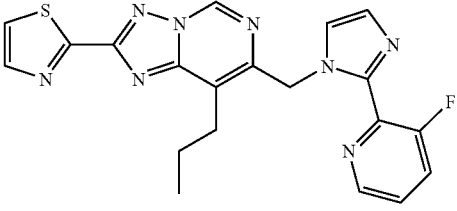 | 7-{[2-(3-fluoropyridin-2-yl)-1H-imidazol-1-yl]methyl}-8-propyl-2-(1,3-thiazol-2-yl)[1,2,4]triazolo[1,5-c]pyrimidine | * | 421.16 |

TABLE 5-continued

| | Compound | Name | $K_i$ | LCMS |
|---|---|---|---|---|
| 259 | | 7-{[2-(3-fluoropyridin-2-yl)-1H-imidazol-1-yl]methyl}-N,N,8-tripropyl[1,2,4]triazolo[1,5-c]pyrimidin-2-amine | * | 437.27 |
| 260 | | 6-(1-{[2-(ethoxymethyl)-8-propyl[1,2,4]triazolo[1,5-c]pyrimidin-7-yl]methyl}-1H-imidazol-2-yl)pyridine-2-carbonitrile | * | 403.22 |
| 261 | | 2-(ethoxymethyl)-7-{[2-(3-fluoropyridin-2-yl)-1H-imidazol-1-yl]methyl}-8-propyl[1,2,4]triazolo[1,5-c]pyrimidine | * | 396.22 |
| 262 | | 6-{1-[(2-methyl-8-propyl[1,2,4]triazolo[1,5-c]pyrimidin-7-yl)methyl]-1H-imidazol-2-yl}pyridine-2-carbonitrile | * | 359.20 |
| 263 | | 7-{[2-(3-fluoropyridin-2-yl)-1H-imidazol-1-yl]methyl}-2-(isopropoxymethyl)-8-propyl[1,2,4]triazolo[1,5-c]pyrimidine | * | 410.23 |
| 264 | | 6-(1-{[2-(isopropoxymethyl)-8-propyl[1,2,4]triazolo[1,5-c]pyrimidin-7-yl]methyl}-1H-imidazol-2-yl)pyridine-2-carbonitrile | * | 417.24 |

TABLE 5-continued

| Compound | | Name | $K_i$ | LCMS |
|---|---|---|---|---|
| 265 | | 2-[(cyclopentyloxy)methyl]-7-{[2-(3-fluoropyridin-2-yl)-1H-imidazol-1-yl]methyl}-8-propyl[1,2,4]triazolo[1,5-c]pyrimidine | * | 436.25 |

TABLE 6

| Compound | | Name |
|---|---|---|
| 266 | | 7-[2-(6-Fluoro-pyridin-2-yl)-imidazol-1-ylmethyl]-3,5-dimethyl-8-propyl-[1,2,4]triazolo[4,3-c]pyrimidine |
| 267 | | 3-Ethyl-7-[2-(6-fluoro-pyridin-2-yl)-imidazol-1-ylmethyl]-5-methyl-8-propyl-[1,2,4]triazolo[4,3-c]pyrimidine |
| 268 | | 3,8-Diethyl-7-[2-(5-fluoro-2-methyl-phenyl)-imidazol-1-ylmethyl]-[1,2,4]triazolo[4,3-c]pyrimidine |
| 269 | | 7-[2-(3-Fluoro-pyridin-2-yl)-imidazol-1-ylmethyl]-8-methoxymethyl-[1,2,4]triazolo[4,3-c]pyrimidine |
| 270 | | 7-[2-(3-Fluoro-pyridin-2-yl)-imidazol-1-ylmethyl]-3-isopropyl-8-propyl-[1,2,4]triazolo[4,3-c]pyrimidine |

TABLE 6-continued

| | Compound | Name |
|---|---|---|
| 271 | | 1-{7-[2-(6-Fluoro-pyridin-2-yl)-imidazol-1-ylmethyl]-3-methyl-[1,2,4]triazolo[4,3-c]pyrimidin-8-yl}-propan-1-ol |
| 272 | | 1-{7-[2-(3-Fluoro-pyridin-2-yl)-imidazol-1-ylmethyl]-3-methyl-[1,2,4]triazolo[4,3-c]pyrimidin-8-yl}-propan-1-ol |
| 273 | | {7-[2-(3-Fluoro-pyridin-2-yl)-imidazol-1-ylmethyl]-8-propyl-[1,2,4]triazolo[4,3-c]pyrimidin-3-yl}-methanol |
| 274 | | 7-[2-(3-Fluoro-pyridin-2-yl)-imidazol-1-ylmethyl]-3-methyl-8-propenyl-[1,2,4]triazolo[4,3-c]pyrimidine |
| 275 | | 7-[2-(3-Fluoro-pyridin-2-yl)-imidazol-1-ylmethyl]-8-propyl-3-pyridin-3-yl-[1,2,4]triazolo[4,3-c]pyrimidine |
| 276 | | 7-[2-(3-Fluoro-pyridin-2-yl)-imidazol-1-ylmethyl]-8-methoxymethyl-3-methyl-[1,2,4]triazolo[4,3-c]pyrimidine |

TABLE 6-continued

| Compound | | Name |
|---|---|---|
| 277 | | 3-{7-[2-(3-Fluoro-pyridin-2-yl)-imidazol-1-ylmethyl]-3-methyl-[1,2,4]triazolo[4,3-c]pyrimidin-8-yl}-propan-1-ol |
| 278 | | 8-(2-Fluoro-ethyl)-7-[2-(3-fluoro-pyridin-2-yl)-imidazol-1-ylmethyl]-3-methyl-[1,2,4]triazolo[4,3-c]pyrimidine |
| 279 | | 2-{7-[2-(3-Fluoro-pyridin-2-yl)-imidazol-1-ylmethyl]-3-methyl-[1,2,4]triazolo[4,3-c]pyrimidin-8-yl}-ethanol |
| 280 | | 8-(3-Fluoro-propyl)-7-[2-(3-fluoro-pyridin-2-yl)-imidazol-1-ylmethyl]-3-methyl-[1,2,4]triazolo[4,3-c]pyrimidine |
| 281 | | 8-(3-Fluoro-propyl)-7-[2-(3-fluoro-pyridin-2-yl)-imidazol-1-ylmethyl]-[1,2,4]triazolo[4,3-c]pyrimidine |
| 282 | | 8-Propyl-7-[2-(6-trifluoromethyl-pyridin-2-yl)-imidazol-1-ylmethyl]-[1,2,4]triazolo[4,3-c]pyrimidine |

TABLE 6-continued

| Compound | Name |
| --- | --- |
| 283 | 2-{1-[8-(3-Fluoro-propyl)-[1,2,4]triazolo[4,3-c]pyrimidin-7-ylmethyl]-1H-imidazol-2-yl}-nicotinonitrile |
| 284 | 6-{1-[8-(3-Fluoro-propyl)-[1,2,4]triazolo[4,3-c]pyrimidin-7-ylmethyl]-1H-imidazol-2-yl}-pyridine-2-carbonitrile |
| 285 | 7-[2-(3-Fluoro-pyridin-2-yl)-imidazol-1-ylmethyl]-8-propyl-[1,2,4]triazolo[4,3-c]pyrimidine-3-carboxylic acid ethyl ester |
| 286 | 7-[2-(3-Fluoro-pyridin-2-yl)-imidazol-1-ylmethyl]-8-propyl-[1,2,4]triazolo[4,3-c]pyrimidine-3-carboxylic acid amide |
| 287 | 7-[2-(3-Fluoro-pyridin-2-yl)-imidazol-1-ylmethyl]-8-propyl-[1,2,4]triazolo[4,3-c]pyrimidine-3-carbonitrile |

TABLE 6-continued

| Compound | | Name |
|---|---|---|
| 288 | [structure] | 7-[4-Chloro-2-(3-fluoro-pyridin-2yl)-imidazol-1-ylmethyl]-8-propyl-[1,2,4]triazolo[4,3-c]pyrimidine |
| 289 | [structure] | 2-[1-(3-methyl-8-propyl-[1,2,4]triazolo[4,3-c]pyrimidin-7-ylmethyl)-1H-imidazol-2-yl]-nicotinonitrile |

Example 6

Ligand Binding Assay

A. Purified Rat Cortical Membranes

Purified Rat Cortical Membranes are Prepared According to Procedure 1 or Procedure 2:

Procedure 1: Frozen rat cortex is homogenized in ice cold 50 mM Tris 7.4 (1 g cortex/150 ml buffer) using a POLYTRON homogenizer (setting 5 for 30 seconds). The suspension is poured into centrifuge tubes, and then centrifuged for 15 minutes at 20,000 rpm in a SS34 rotor (48,000×g). The supernatants are discarded and the pellets are washed twice with same buffer and centrifuge speed. The final pellets are stored in covered centrifuge tubes at −80° C. Prior to use, the washed rat cortical membrane is thawed and re-suspended in ice cold 50 mM Tris 7.4 (6.7 mg frozen cortex weight/ml buffer).

Procedure 2: Rat cortical tissue is dissected and homogenized in 25 volumes (w/v) of Buffer A (0.05 M Tris HCl buffer, pH 7.4 at 4° C.). The tissue homogenate is centrifuged in the cold (4° C.) at 20,000×g for 20 minutes. The supernatant is decanted, the pellet rehomogenized in the same volume of buffer, and centrifuged again at 20,000×g. The supernatant of this centrifugation step is decanted and the pellet stored at −20° C. overnight. The pellet is then thawed and resuspended in 25 volumes of Buffer A (original wt/vol), centrifuged at 20,000×g and the supernatant decanted. This wash step is repeated once. The pellet is finally resuspended in 50 volumes of Buffer A.

B. Radioligand Binding Assays

The affinity of compounds provided herein for the benzodiazepine site of the $GABA_A$ receptor is confirmed using a binding assay essentially described by Thomas and Tallman (*J. Bio. Chem.* (1981) 156:9838–9842, and *J. Neurosci.* (1983) 3:433–440). Membranes prepared via Procedure 1 are assayed according to Method 1. and membranes prepared via Procedure 2 are assayed according to Method 2.

Method 1: Incubations are carried out at 1.2 mg membrane/well. Duplicate samples containing 180 μL of membrane suspension, 20 μL of $^3$H-Ro15-1788 ($^3$H-Flumazenil (PerkinElmer Life Sciences, Boston, Mass.) and 2 μL of test compound or control in DMSO (total volume of 202 μL) are incubated at 4° C. for 60 minutes. The incubation is terminated by rapid filtration through untreated 102×258 mm filter mats on Tomtec filtration manifold (Hamden, Conn.) and the filters are rinsed three times with ice cold 50 mM Tris 7.4. The filters are air dried and counted on a Wallac 1205 Betaplate Liquid Scintillation Counter. Nonspecific binding (control) is determined by displacement of $^3$H-RO15-1788 by $10^{-6}$ M 4-oxo-4,5,6,7-tetrahydro-1H-indole-3-carboxylic acid [4-(2-propylamino-ethoxy)-phenyl]-amide. Percent inhibition of total specific binding (Total Specific Binding=Total−Nonspecific) is calculated for each compound.

Method 2: Incubations contain 100 μl of tissue homogenate, 100 μl of radioligand (0.5 nM $^3$H-RO15-1788, specific activity 80 Ci/mmol) and test compound or control (see below), and are brought to a total volume of 500 μl with Buffer A. Incubations are carried out for 30 minutes at 4° C. and then rapidly filtered through Whatman GFB filters to separate free and bound ligand. Filters are washed twice with fresh Buffer A and counted in a liquid scintillation counter. Nonspecific binding (control) is determined by displacement of $^3$H RO15-1788 with 10 μM Diazepam (Research Biochemicals International, Natick, Mass.). Data are collected in triplicate, averaged, and percent inhibition of total specific binding (Total Specific Binding=Total−Nonspecific) is calculated for each compound.

Analysis: A competition binding curve is obtained with up to 11 points (e.g., 7 points) spanning the test compound concentration range from $10^{-12}$M or $10^{-11}$ M to $10^{-5}$M. $IC_{50}$ and Hill coefficient ("nH") are determined by fitting the displacement binding data with the aid of SIGMAPLOT software (SPSS Inc., Chicago, Ill.). The $K_i$ is calculated using the Cheng-Prusoff equation (*Biochemical Pharmacology* 22:3099–3108 (1973)): $K_i=IC_{50}/(1+[L]/K_d)$, where $IC_{50}$ is determined as by SIGMAPLOT as the concentration of compound which displaces ½ the maximal $^3$H-Ro15-1788 binding, [L] is the $^3$H-Ro15-1788 concentration used to label the target, and $K_d$ is the binding dissociation constant of $^3$H-Ro15-1788, previously determined to be 1.0 nM. Preferred compounds of the invention exhibit $K_i$ values of less than 100 nM and more preferred compounds of the invention exhibit $K_i$ values of less than 10 nM.

Example 7

Electrophysiology

The following assay is used to determine if a compound of the invention alters the electrical properties of a cell and if it acts as an agonist, an antagonist or an inverse agonist at the benzodiazepine site of the $GABA_A$ receptor.

Assays are carried out essentially as described in White and Gurley (NeuroReport 6:1313–1316, 1995) and White, Gurley, Hartnett, Stirling and Gregory (Receptors and Channels 3:1–5, 1995) with modifications. Electrophysiological recordings are carried out using the two electrode voltage-clamp technique at a membrane holding potential of −70 mV. *Xenopus laevis* oocytes are enzymatically isolated and injected with non-polyadenylated cRNA mixed in a ratio of 4:1:4 for α, β and γ subunits, respectively. Of the nine combinations of α, β and γ subunits described in the White et al. publications, preferred combinations are $\alpha_1\beta_2\gamma_2$, $\alpha_2\beta_3\gamma_2$, $\alpha_3\beta_3\gamma_2$ and $\alpha_5\beta_3\gamma_2$. Preferably all of the subunit cRNAs in each combination are human clones or all are rat clones. Each of these cloned subunits is described in GENBANK, e.g., human $\alpha_1$, GENBANK accession no. X14766, human $\alpha_2$, GENBANK accession no. A28100; human $\alpha_3$, GENBANK accession no. A28102; human $\alpha_5$, GENBANK accession no. A28104; human $\beta_2$, GENBANK accession no. M82919; human $\beta_3$, GENBANK accession no. Z20136; human $\gamma_2$, GENBANK accession no. X15376; rat $\alpha_1$, GENBANK accession no. L08490, rat $\alpha_2$, GENBANK accession no. L08491; rat $\alpha_3$, GENBANK accession no. L08492; rat $\alpha_5$, GENBANK accession no. L08494; rat $\beta_2$, GENBANK accession no. X15467; rat $\beta_3$, GENBANK accession no. X15468; and rat $\gamma_2$, GENBANK accession no. L08497. For each subunit combination, sufficient message for each constituent subunit is injected to provide current amplitudes of >10 nA when 1 µM GABA is applied.

Compounds are evaluated against a GABA concentration that evokes <10% of the maximal evocable GABA current (e.g., 1 µM–9 µM). Each oocyte is exposed to increasing concentrations of a compound being evaluated (test compound) in order to evaluate a concentration/effect relationship. Test compound efficacy is calculated as a percent-change in current amplitude: $100*((Ic/I)-1)$, where Ic is the GABA evoked current amplitude observed in the presence of test compound and I is the GABA evoked current amplitude observed in the absence of the test compound.

Specificity of a test compound for the benzodiazepine site is determined following completion of a concentration/effect curve. After washing the oocyte sufficiently to remove previously applied test compound, the oocyte is exposed to GABA+1 µM RO15-1788, followed by exposure to GABA+1 µM RO15-1788+test compound. Percent change due to addition of compound is calculated as described above. Any percent change observed in the presence of RO15-1788 is subtracted from the percent changes in current amplitude observed in the absence of 1 µM RO15-1788. These net values are used for the calculation of average efficacy and $EC_{50}$ values by standard methods. To evaluate average efficacy and $EC_{50}$ values, the concentration/effect data are averaged across cells and fit to the logistic equation.

Example 8

MDCK Toxicity Assay

This Example illustrates the evaluation of compound toxicity using a Madin Darby canine kidney (MDCK) cell cytotoxicity assay.

1 µL of test compound is added to each well of a clear bottom 96-well plate (PACKARD, Meriden, Conn.) to give final concentration of compound in the assay of 10 micromolar, 100 micromolar or 200 micromolar. Solvent without test compound is added to control wells.

MDCK cells, ATCC no. CCL-34 (American Type Culture Collection, Manassas, Va.), are maintained in sterile conditions following the instructions in the ATCC production information sheet. Confluent MDCK cells are trypsinized, harvested and diluted to a concentration of $0.1 \times 10^6$ cells/ml with warm (37° C.) medium (VITACELL Minimum Essential Medium Eagle, ATCC catalog # 30-2003). 100 µL of diluted cells is added to each well, except for five standard curve control wells that contain 100 µL of warm medium without cells. The plate is then incubated at 37° C. under 95% $O_2$, 5% $CO_2$ for 2 hours with constant shaking. After incubation, 50 µL of mammalian cell lysis solution is added per well, the wells are covered with PACKARD TOPSEAL stickers, and plates are shaken at approximately 700 rpm on a suitable shaker for 2 minutes.

Compounds causing toxicity will decrease ATP production, relative to untreated cells. The PACKARD, (Meriden, Conn.) ATP-LITE-M Luminescent ATP detection kit, product no. 6016941, is generally used according to the manufacturer's instructions to measure ATP production in treated and untreated MDCK cells. PACKARD ATP LITE-M reagents are allowed to equilibrate to room temperature. Once equilibrated, the lyophilized substrate solution is reconstituted in 5.5 ml of substrate buffer solution (from kit). Lyophilized ATP standard solution is reconstituted in deionized water to give a 10 mM stock. For the five control wells, 10 µL of serially diluted PACKARD standard is added to each of the standard curve control wells to yield a final concentration in each subsequent well of 200 nM, 100 nM, 50 nM, 25 nM and 12.5 nM. rACKARD substrate solution (50 µL) is added to all wells, which are then covered, and the plates are shaken at approximately 700 rpm on a suitable shaker for 2 minutes. A white PACKARD sticker is attached to the bottom of each plate and samples are dark adapted by wrapping plates in foil and placing in the dark for 10 minutes. Luminescence is then measured at 22° C. using a luminescence counter (e.g.; PACKARD TOPCOUNT Microplate Scintillation and Luminescence Counter or TECAN SPECTRAFLUOR PLUS), and ATP levels calculated from the standard curve. ATP levels in cells treated with test compound(s) are compared to the levels determined for untreated cells. Cells treated with 10 µM of a preferred test compound exhibit ATP levels that are at least 80%, preferably at least 90%, of the untreated cells. When a 100 µM concentration of the test compound is used, cells treated with preferred test compounds exhibit ATP levels that are at least 50%, preferably at least 80%, of the ATP levels detected in untreated cells.

What is claimed is:

1. A compound of the formula:

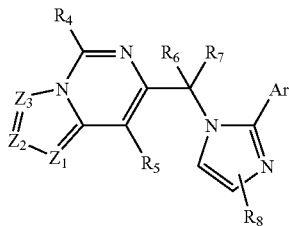

or a pharmaceutically acceptable salt thereof, wherein:
$Z_1$ is nitrogen,
$Z_2$ is nitrogen or $CR_2$, and
$Z_3$ is nitrogen or $CR_3$, such that no more than two, of $Z_1$, $Z_2$ and $Z_3$ are nitrogen; or
$Z_1$ is $CR_1$, $Z_2$ is nitrogen, and $Z_3$ is $CR_3$;
$R_1$, $R_2$, and $R_3$ are each independently selected from:
(a) hydrogen, halogen, nitro and cyano; and
(b) groups of the formula:

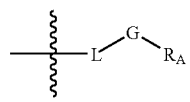

wherein:
L is a bond or $C_1$–$C_8$alkylene;
G is a bond, $N(R_B)$, O C(=O), C(=O)O, C(=O)N$(R_B)$, $N(R_B)$C(=O), $S(O)_m$, $CH_2C$(=O), $S(O)_mN(R_B)$ or $N(R_B)S(O)_m$; wherein m is 0, 1 or 2; and
$R_A$ and each $R_B$ are independently selected from:
(i) hydrogen; and
(ii) $C_1$–$C_8$alkyl, $C_2$–$C_8$alkenyl, $C_2$–$C_8$alkynyl, ($C_3$–$C_8$cycloalkyl)$C_0$–$C_4$alkyl, (3-to 7-membered heterocycloalkyl)$C_0$–$C_4$alkyl, ($C_6$–$C_{10}$aryl)$C_0$–$C_2$alkyl or (5-to 10-membered heteroaryl)$C_0$–$C_2$alkyl, each of which is substituted with from 0 to 4 substituents independently selected from halogen, hydroxy, nitro, cyano, amino, $C_1$–$C_4$alkyl, $C_1$–$C_4$alkoxy, $C_1$–$C_4$alkanoyl, mono- and di($C_1$–$C_4$alkyl)amino, $C_1$–$C_4$haloalkyl and $C_1$–$C_4$haloalkoxy;
$R_4$ is hydrogen, $C_1$–$C_8$alkyl, $C_2$–$C_8$alkenyl, $C_2$–$C_8$alkynyl, or ($C_3$–$C_8$cycloalkyl)$C_0$–$C_4$alkyl;
$R_5$ is:
(a) hydrogen, halogen or cyano; or
(b) $C_1$–$C_6$alkyl, $C_2$–$C_6$alkenyl, $C_2$–$C_6$alkynyl, $C_1$–$C_4$alkoxy or mono- or di-($C_{1–C4}$alkyl)amino, each of which is substituted with from 0 to 5 substituents independently chosen from halogen, hydroxy, nitro, cyano, amino, $C_1$–$C_4$alkoxy, $C_1$–$C_2$haloalkyl, $C_1$–$C_2$haloalkoxy, mono- and di-($C_1$–$C_4$alkyl)amino, $C_3$-$C_8$cycloalkyl, phenyl, phenyl$C_1$–$C_4$alkoxy and 5- or 6-membered heteroaryl;
$R_6$ and $R_7$ are independently hydrogen, methyl, ethyl or halogen;
$R_8$ represents 0, 1 or 2 substituents independently chosen from halogen, hydroxy, nitro, cyano, amino, $C_1$–$C_4$alkyl, $C_1$–$C_4$alkoxy, mono- and di($C_1$–$C_4$alkyl)amino, $C_3$-$C_7$cycloalkyl, $C_1$–$C_2$haloalkyl and $C_1$–$C_2$haloalkoxy; and Ar represents phenyl, naphthyl, pyridyl, pyridazinyl, pyrimidinyl, thiazolyl or thienyl, each of which is substituted with from 0 to 4 substituents independently chosen from halogen, hydroxy, nitro, cyano, amino, $C_1$–$C_8$alkyl, $C_2$–$C_8$alkenyl, $C_2$–$C_8$alkynyl, $C_1$–$C_8$alkoxy, ($C_3$–$C_7$cycloalkyl )$C_0$–$C_4$alkyl, ($C_3$–$C_7$cycloalkyl)$C_1$–$C_4$alkoxy, $C_2$–$C_8$alky ether, $C_3$–$C_8$alkanone, $C_1$–$C_8$alkanoyl, (3- to 7-membered heterocycloalkyl)$C_0$–$C_4$alkyl, $C_1$–$C_8$haloalkyl, $C_1$–$C_8$haloalkoxy, $C_1$–$C_8$hydroxyalkyl, $C_1$–$C_8$aminoalkyl, and mono- and di-($C_1$–$C_8$alkyl) amino $C_0$–$C_8$alkyl.

2. A compound or salt according to claim 1, wherein $R_8$ represents 0 substituents or 1 substituent selected from halogen, $C_1$–$C_2$alkyl and $C_1$–$C_2$alkoxy.

3. A compound or salt according to claim 1, wherein Ar is substituted with 0, 1, 2 or 3 substituents independently selected from halogen, hydroxy, amino, cyano, $C_1$–$C_4$alkyl, $C_1$–$C_4$alkoxy, mono- or di-($C_1$–$C_4$alkyl)amino, $C_2$-$C_4$alkanoyl, ($C_3$–$C_7$cycloalkyl)$C_0$–$C_2$alkyl, $C_1$–$C_2$haloalkyl and $C_1$–$C_2$haloalkoxy.

4. A compound or salt according to claim 3, wherein Ar represents phenyl, pyridyl, thiazolyl, thienyl or pyridazinyl, each of which is substituted with from 0 to 3 substituents independently selected from chloro, fluoro, hydroxy, cyano, amino, $C_1$–$C_4$alkyl, $C_1$–$C_4$alkoxy, mono- or di-($C_1$–$C_2$alkyl) amino, $C_1$–$C_2$haloalkyl and $C_1$-$C_2$haloalkoxy.

5. A compound or salt according to claim 4, wherein Ar represents phenyl, pyridin-2-yl, 1,3-thiazol-2-yl, thien-2-yl or pyridazin-3-yl, each of which is substituted with from 0 to 3 substituents independently selected from fluoro, chloro, hydroxy, $C_1$–$C_2$alkyl, cyano and $C_1$–$C_2$alkoxy.

6. A compound or salt according to claim 4, wherein Ar represents 2,6-difluoro-phenyl, 2,5-difluoro-phenyl, 5-fluoro-2-methyl-phenyl, pyridine-2-yl, 3-fluoro-pyridin-2-yl, 3-cyano-pyridi n-2y1,3-trifluoromethyl-pyridin-2-yl, 3-hydroxy-pyridin-2-yl, 3methoxy-pyridi n-2-yl, 6-fluoro-pyridin-2-yl, 6-cyano-pyridin-2-yl, 6-trifiuoromethyl-pyridin-2-yl, 6-hydroxy-pyridin-2-yl or 6-methoxy-pyridin-2-yl.

7. A compound or salt according to claim 1, wherein $R_1$, $R_2$, and $R_3$ are independently selected from:
(a) hydrogen, halogen or cyano; and
(b) groups of the formula:

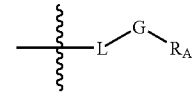

wherein:
(i) L is a bond;
(ii) G is a bond, NH, $N(R_B)$, O, C(=O)O or C(=O); and
(iii) $R_A$ and $R_B$ are independently selected from (1) hydrogen and (2) $C_1$–$C_6$alkyl, $C_2$–$C_6$alkenyl, ($C_3$–$C_7$cycloalkyl)$C_0$–$C_2$alkyl, ($_3$- to $_7$-membered heterocycloalkyl)$C_0$–$C_2$alkyl, phenyl, thienyl, pyridyl, pyrimidinyl, thiazolyl and pyrazinyl, each of which is substituted with from 0 to 4 substituents independently selected from hydroxy, halogen, cyano, amino, $C_1$–$C_2$alkyl and $C_1$–$C_2$alkoxy.

8. A compound or salt according to claim 7 wherein $R_1$, $R_2$, and $R_3$ are independently selected from hydrogen, hydroxy, halogen, cyano, carboxamido, $C_1$–$C_6$alkyl, $C_1$–$C_6$alkoxy, $C_2$–$C_6$alkyl ether, $C_3$–$C_7$cycloalkyl, $C_1$–$C_4$hydroxyalkyl, $C_1$–$C_2$haloalkyl, $C_1$–$C_2$haloalkoxy, $C_1$–$C_6$alkoxycarbonyl, mono- and di -($C_1$–$C_4$alkyl)amino, phenyl and pyridyl.

9. A compound or salt according to claim 8, wherein $R_1$ and $R_4$ are independently selected from hydrogen, methyl and ethyl.

10. A compound or salt according to claim 1, wherein $Z_1$ and $Z_3$ are nitrogen and $Z_2$ is $CR_2$.

11. A compound or salt according to claim 10, wherein $R_2$ is selected from hydrogen, cyano, carboxamido, $C_1$–$C_4$alkyl, $C_1$–$C_4$alkoxy, $C_1$-$C_4$alkoxycarbonyl, $C_2$–$C_4$alkyl ether, $C_3$–$C_7$cycloalkyl, $C_1$–$C_2$hydroxyalkyl, fluoromethyl, difluoromethyl, trifluoromethyl, phenyl and pyridyl.

12. A compound or salt according to claim 1, wherein $Z_1$ is nitrogen, $Z_2$ is $CR_2$ and $Z_3$ is $CR_3$.

13. A compound or salt according to claim 12, wherein $R_2$ and $R_3$ are independently selected from hydrogen, cyano, carboxamido, $C_1$–$C_4$alkyl, $C_1$-$C_4$alkoxy, trifluoromethyl, phenyl, pyridyl, methylcarboxylate and ethylcarboxylate.

14. A compound or salt according claim 1, wherein $_1$, is $CR_1$, $Z_2$ is nitrogen and $Z_3$ is $CR_3$.

15. A compound or salt according to claim 14, wherein $R_3$ is hydrogen or methyl.

16. A compound or salt according to claim 1, wherein $Z_1$ and $Z_2$ are nitrogen and $Z_3$ is $CR_3$.

17. A compound or salt according to claim 15, wherein $R_3$ is hydrogen, cyano, $C_1$–$C_6$alkyl, $C_1$–$C_6$hydroxyalkyl, $C_3$–$C_7$cycloalkyl, $C_2$–$C_6$alkylether, $C_1$–$C_6$haloalkyl, $C_1$–$C_6$alkanoyl, pyridyl or carboxamido.

18. A compound or salt according to claim 1, wherein $R_6$ and $R_7$ are both hydrogen.

19. A compound or salt according to claim 1, wherein $R_5$ is $C_1$–$C_6$ alkyl, $C_2$–$C_6$ alkenyl, $C_1$–$C_4$ alkoxy, or mono- or di-$C_1$–$C_4$alkylamino, each of which is substituted with from 0 to 3 substituents independently selected from halogen, hydroxy, $C_1$–$C_2$alkoxy, $C_3$–$C_8$cycloalkyl, phenyl and phenyl$C_1$–$C_2$alkoxy.

20. A compound or salt according to claim 19, wherein $R_5$ is ethyl, propyl, butyl, ethoxy or methoxymethyl.

21. A compound or salt according to claim 1, wherein the compound has the formula:

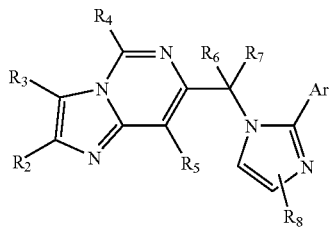

wherein:
$R_2$ and $R_3$ are independently selected from hydrogen, hydroxy, halogen, cyano, carboxamido, $C_1$–$C_6$alkyl, $C_1$–$C_6$alkoxy, $C_3$–$C_7$cycloalkyl, $C_2$–$C_6$alkyl ether, $C_1$–$C_4$hydroxyalkyl, $C_1$–$C_2$haloalkyl, $C_1$–$C_2$haloalkoxy, $C_1$–$C_4$alkoxycarbonyl, mono- and di-($C_1$–$C_4$alkyl)amino, phenyl and pyridyl;
$R_4$ is hydrogen, methyl or ethyl;
$R_5$ is $C_1$–$C_6$ alkyl, $C_2$–$C_6$ alkenyl, $C_1$–$C_4$ alkoxy, or mono- or di-$C_1$–$C_4$alkylamino, each of which is substituted with from 0 to 3 substituents independently selected from halogen, hydroxy, $C_1$–$C_2$alkoxy, $C_3$–$C_8$cycloalkyl, phenyl and phenyl$C_1$–$C_2$alkoxy;
$R_6$ and $R_7$ are independently hydrogen, methyl, ethyl or halogen;
$R_8$ represents 0 or 1 substituent selected from halogen, $C_1$–$C_2$alkyl and $C_1$–$C_2$alkoxy;
and
Ar represents phenyl, 2-pyridyl, 1,3-thiazol-2-yl, 2-thienyl or 3-pyridazinyl, each of which is substituted with from 0 to 3 substituents independently selected from fluoro, chloro, hydroxy, $C_1$–$C_2$alkyl, $C_1$–$C_2$haloalkyl, cyano and $C_1$–$C_2$alkoxy.

22. A compound or salt according to claim 1, wherein the compound has the formula:

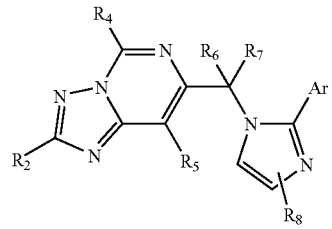

wherein:
$R_2$ is selected from hydrogen, hydroxy, halogen, cyano, carboxamido, $C_1$–$C_6$alkyl, $C_1$–$C_6$alkoxy, $C_3$–$C_7$cycloalkyl, $C_2$–$C_6$alkyl ether, $C_1$–$C_4$hydroxyalkyl, $C_1$–$C_2$ haloalkyl, $C_1$–$C_2$haloalkoxy, $C_1$–$C_4$alkoxycarbonyl, mono- and di-($C_1$–$C_4$alkyl)amino, phenyl and pyridyl;
$R_4$ is hydrogen, methyl or ethyl;
$R_5$ is $C_1$–$C_6$ alkyl, $C_2$–$C_6$alkenyl, $C_1$–$C_4$ alkoxy, or mono- or di-$C_1$–$C_4$alkylamino, each of which is substituted with from 0 to 3 substituents independently selected from halogen, hydroxy, $C_1$–$C_2$alkoxy, $C_3$–$C_8$cycloalkyl, phenyl and phenyl$C_1$–$C_2$alkoxy;
$R_6$ and $R_7$ are independently hydrogen, methyl, ethyl or halogen;
$R_8$ represents 0 or 1 substituent selected from halogen, $C_1$–$C_2$alkyl and $C_1$–$C_2$alkoxy;
and
Ar represents phenyl, 2-pyridyl, 1,3-thiazol-2-yl, 2-thienyl or 3-pyridazinyl, each of which is substituted with from 0 to 3 substituents independently selected from fluoro, chloro, hydroxy, $C_1$–$C_2$alkyl, $C_1$–$C_2$haloalkyl, cyano and $C_1$–$C_2$alkoxy.

23. A compound or salt according to claim 1, wherein the compound has the formula:

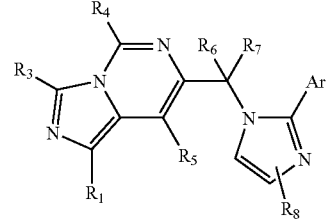

wherein:
$R_1$ is hydrogen, halogen or $C_1$–$C_6$alkyl;
$R_3$ is selected from hydrogen, hydroxy, halogen, cyano, carboxamido, $C_1$–$C_6$alkyl, $C_1$–$C_6$alkoxy, $C_3$–$C_7$cycloalkyl, $C_2$–$C_6$alkyl ether, $C_1$–$C_4$hydroxyalkyl, $C_1$–$C_2$haloalkyl, $C_1$–$C_2$haloalkoxy, $C_1$–$C_4$alkoxycarbonyl, mono- and di-($C_1$–$C_4$alkyl)amino, phenyl and pyridyl;

$R_4$ is hydrogen, methyl or ethyl;

$R_5$ is $C_1$–$C_6$ alkyl, $C_2$–$C_6$ alkenyl, $C_1$–$C_4$ alkoxy, or mono- or di-$C_1$–$C_4$alkylamino, each of which is substituted with from 0 to 3 substituents independently selected from halogen, hydroxy, $C_1$–$C_2$alkoxy, $C_3$–$C_8$cycloalkyl, phenyl and phenyl$C_1$–$C_2$alkoxy;

$R_6$ and $R_7$ are independently hydrogen, methyl, ethyl or halogen;

$R_8$ represents 0 or 1 substituent selected from halogen, $C_1$–$C_2$alkyl and $C_1$–$C_2$alkoxy;

and

Ar represents phenyl, 2-pyridyl, 1,3-thiazol-2-yl, 2-thienyl or 3-pyridazinyl, each of which is substituted with from 0 to 3 substituents independently selected from fluoro, chloro, hydroxy, $C_1$–$C_2$alkyl, $C_1$–$C_2$haloalkyl, cyano and $C_1$–$C_2$alkoxy.

24. A compound or salt according to claim 1, wherein the compound has the formula:

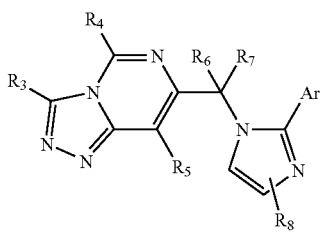

wherein:

$R_3$ is selected from hydrogen, hydroxy, halogen, cyano, carboxamido, $C_1$–$C_6$alkyl, $C_1$–$C_6$alkoxy, $C_3$–$C_7$cycloalkyl, $C_2$–$C_6$alkyl ether, $C_1$–$C_4$hydroxyalkyl, $C_1$–$C_2$haloalkyl, $C_1$–$C_2$haloalkoxy, $C_1$–$C_4$alkoxycarbonyl, mono- and di-($C_1$–$C_4$alkyl)amino, phenyl and pyridyl;

$R_4$ is hydrogen, methyl or ethyl;

$R_5$ is $C_1$–$C_6$ alkyl, $C_2$–$C_6$ alkenyl, $C_1$–$C_4$ alkoxy, or mono- or di-$C_1$–$C_4$alkylamino, each of which is substituted with from 0 to 3 substituents independently selected from halogen, hydroxy, $C_1$–$C_2$alkoxy, $C_3$–$C_8$cycloalkyl, phenyl and phenyl$C_1$–$C_2$alkoxy;

$R_6$ and $R_7$ are independently hydrogen, methyl, ethyl or halogen;

$R_8$ represents 0 or 1 substituent selected from halogen, $C_1$–$C_2$alkyl and $C_1$–$C_2$alkoxy;

and

Ar represents phenyl, 2-pyridyl, 1,3-thiazol-2-yl, 2-thienyl or 3-pyridazinyl, each of which is substituted with from 0 to 3 substituents independently selected from fluoro, chloro, hydroxy, $C_1$–$C_2$alkyl, $C_1$–$C_2$haloalkyl, cyano and $C_1$–$C_2$alkoxy.

25. A compound or salt according to claim 1, wherein the compound exhibits a $K_i$ of 1 micromolar or less in a competitive assay of $GABA_A$ receptor binding using $^3$H-Ro15-1788, wherein $K_i$ is calculated using the equation $K_i = IC_{50}/(1+/K_d)$, in which $IC_{50}$ is the concentration of compound which displaces ½ the maximal $^3$H-Ro15-1788 binding, is the $^3$H-Ro15-1788 concentration, and $K_d$ is 1.0 nM.

26. A compound or salt according to claim 25, wherein the compound exhibits a $K_i$ of 100 nanomolar or less in the competitive assay of $GABA_A$ receptor binding using $^3$H-Ro15-1788.

27. A compound or salt according to claim 26, wherein the compound exhibits a $K_i$ of 10 nanomolar or less in the competitive assay of $GABA_A$ receptor binding using $^3$H-Ro15-1788.

28. A pharmaceutical composition comprising a compound or salt according to claim 1 in combination with a physiologically acceptable carrier or excipient.

29. A pharmaceutical composition according to claim 28, wherein the pharmaceutical composition is formulated as an injectible fluid, an aerosol, a cream, a gel, a pill, a capsule, a syrup or a transdermal patch.

30. A method for the treatment of anxiety or depression comprising administering to a patient in need of such treatment a therapeutically effective amount of a compound or salt according to claim 1.

31. A packaged pharmaceutical preparation comprising a pharmaceutical composition according to claim 28 in a container and instructions for using the composition to treat a patient suffering from anxiety, depression, or a sleep disorder.

32. A compound or salt according to claim 1, wherein the compound is 7-[2-(6-fluoro-pyridin-2-yl)-imidazol-1 -ylmethyl]-8-propyl-imidazo[1,2-c]pyrimidine.

33. A compound or salt according to claim 1, wherein the compound is 7-[2-(6-fluoro-pyridin-2-yl )-imidazol-1-ylmethyl]-2,3-dimethyl-8-propyl-imidazo [1,2-c]pyrimidine.

34. A compound or salt according to claim 1, wherein the compound is 2-ethyl-7-[2-(6-fluoro-pyridin-2-yl)-imidazol-1-ylmethyl]-8-propyl-imidazo[1,2-c]pyrimidine.

35. A compound or salt according to claim 1, wherein the compound is 7-[2-(6-fluoro-pyridin-2-yl )-imidazol-1 -ylmethyl]-8-propyl-imidazo[1,2-c]pyrimidine-3-carboxylic acid ethyl ester.

36. A compound or salt according to claim 1, wherein the compound is 7-[2-(6-fluoro-pyridin-2-yl)-imidazol-1-ylmethyl]-8-propyl-imidazo[1,2-c]pyrimidine-2-carboxylic acid ethyl ester.

37. A compound or salt according to claim 1, wherein the compound is 7-[2-(6-fluoro-pyridin-2-yl)-imidazol-1 -ylmethyl]-2-methyl-8-propyl-imidazo[1,2-c]pyrimidine.

38. A compound or salt according to claim 1, wherein the compound is 7-[2-(6-fluoro-pyridin-2-yl)-imidazol-1-ylmethyl]-8-propyl-2-trifluoromethyl-imidazo [1,2-c]pyrimidine.

39. A compound or salt according to claim 1, wherein the compound is 8-propyl-7-(2-pyridin-2-yl-imidazol-1 -ylmethyl)-imidazo[1,2-c]pyrimidine.

40. A compound or salt according to claim 1, wherein the compound is 8-propyl-7-(2-pyridin-2-yl-imidazol-1 -ylmethyl )-2-trifluoromethyl-imidazo[1,2-c ]pyrimidine.

41. A compound or salt according to claim 1, wherein the compound is 7-[2-(2,6-difluoro-phenyl )-imidazol-1-ylmethyl]-8-propyl-imidazo[1,2-c ]pyrimidine.

42. A compound or salt according to claim 1, wherein the compound is 7-[2-(2,6-difluoro-phenyl )-imidazol-1-ylmethyl]-8-propyl-2-trifluoromethyl-imidazo [1,2-c]pyrimidine.

43. A compound or salt according to claim 1, wherein the compound is 7-[2-(3-fluoro-pyridin-2-yl)-imidazol-1 -ylmethyl]-8-propyl-imidazo[1,2-c ]pyrimidine.

44. A compound or salt according to claim 1, wherein the compound is 7-[(pyridin-2-yl )-imidazol-1-ylmethyl]-2-phenyl-8-propyl-imidazo[1,2-c]pyrimidine.

45. A compound or salt according to claim 1, wherein the compound is 7-[2-(6-fluoro-pyridin-2-yl)-imidazol-1-ylmethyl]-5-methyl-8-propyl-imidazo[1,2-c]pyrimidine.

46. A compound or salt according to claim 1, wherein the compound is 7-[2-(6-fluoro-pyridin-2-yl)-imidazol-1-ylmethyl]-8-propyl-imidazo[1,2-c]pyrimidine-2-carbonitrile.

47. A compound or salt according to claim 1, wherein the compound is 7-[2-(6-fluoro-pyridin-2-yl)-imidazol-1-ylmethyl]-8-propyl-imidazo[1,2-c]pyrimidine-3-carbonitrile.

48. A compound or salt according to claim 1, wherein the compound is 7-[2-(3-fluoro-pyridin-2-yl)-imidazol-1-ylmethyl]-2-methyl-8-propyl-[1,2,4]triazolo[1,5-c]pyrimidine.

49. A compound or salt according to claim 1, wherein the compound is 7-[2-(6-fluoro-pyridin-2-yl)-imidazol-1-ylmethyl]-2-methyl-8-propyl-[1,2,4]triazolo[1,5-c]pyrimidine.

50. A compound or salt according to claim 1, wherein the compound is 7-[2-(6-fluoro-pyridin-2-yl)-imidazol-1-ylmethyl]-8-propyl-[1,2,4]triazolo[1,5-c]pyrimidine.

51. A compound or salt according to claim 1, wherein the compound is 7-[2-(3-fluoro-pyridin-2-yl)-imidazol-1-ylmethyl]-8-propyl-[1,2,4]triazolo[1,5-c]pyrimidine.

52. A compound or salt according to claim 1, wherein the compound is 1-{7-[2-(3-fluoro-pyridin-2-yl)-imidazol-1-ylmethyl[-8-propyl-[1,2,4]triazolo[1,5-c]pyrimidin-2-yl}-ethanol.

53. A compound or salt according to claim 1, wherein the compound is 7-[2-(3-fluoro-pyridin-2-yl)-imidazol-1-ylmethyl]-8-propyl-2-trifluoromethyl-[1,2,4]triazolo[1,5-c]pyrimidine.

54. A compound or salt according to claim 1, wherein the compound is 7-[2-(3-fluoro-pyridin-2-yl)-imidazol-1-ylmethyl]-2-methoxymethyl-8-propyl[1,2,4]triazolo[1,5-c]pyrimidine.

55. A compound or salt according to claim 1, wherein the compound is 7-[2-(6-fluoro-pyridin-2-yl)-imidazol-1-ylmethyl]-2-methoxymethyl-8-propyl-[1,2,4]triazolo[1,5-c]pyrimidine.

56. A compound or salt according to claim 1, wherein the compound is 2-cyclobutyl-7-[2-(6-fluoro-pyridin-2-yl)-imidazol-1-ylmethyl]-8-propyl-[1,2,4]triazolo[1,5-c]pyrimidine.

57. A compound or salt according to claim 1, wherein the compound is 8-propyl-7-(2-pyridin-2-yl-imidazol-1-ylmethyl)-[1,2,4]triazolo[1,5-c]pyrimidine.

58. A compound or salt according to claim 1, wherein the compound is 7-[2-(2,5-difluoro-phenyl)-imidazol-1-ylmethyl]-2-methyl-8-propyl-[1,2,4]triazolo[1,5-c]pyrimidine.

59. A compound or salt according to claim 1, wherein the compound is 7-[2-(6-methoxy-pyridin-2-yl)-imidazol-1-ylmethyl]-8-propyl-[1,2,4]triazolo[1,5-c]pyrimidine.

60. A compound or salt according to claim 1, wherein the compound is 2-methyl-8-propyl-7-(2-thiazol-2-yl-imidazol-1-ylmethyl)-[1,2,4]triazolo[1,5-c]pyrimidine.

61. A compound or salt according to claim 1, wherein the compound is 2-methyl-8-propyl-7-(2-pyridin-2-yl-imidazol-1-ylmethyl)-[1,2,4]triazolo[1,5-c]pyrimidine.

62. A compound or salt according to claim 1, wherein the compound is 6-[1-(8-propyl-[1,2,4]triazolo[1,5-c]pyrimidin-7-ylmethyl)-1H-imidazol-2-yl]-pyridin-2-ol.

63. A compound or salt according to claim 1, wherein the compound is 7-[2-(2,6-difluoro-phenyl)-imidazol-1-ylmethyl]-8-propyl-[1,2,4]triazolo[1,5-c]pyrimidine.

64. A compound or salt according to claim 1, wherein the compound is 8-propyl-7-(2-thiophen-2-yl-imidazol-1-ylmethyl)-[1,2,4]triazolo[1,5-c]pyrimidine.

65. A compound or salt according to claim 1, wherein the compound is 2-methyl-8-propyl-7-(2-pyridazin-3-yl-imidazol-1-ylmethyl)-[1,2,4]triazolo[1,5-c]pyrimidine.

66. A compound or salt according to claim 1, wherein the compound is 7-[2-(2,5-difluoro-phenyl)-imidazol-1-ylmethyl]-8-ethyl-[1,2,4]triazolo[1,5-c]pyrimidine.

67. A compound or salt according to claim 1, wherein the compound is 7-[2-(2,5-difluoro-phenyl)-imidazol-1-ylmethyl]-8-ethyl-2-methyl-[1,2,4]triazolo[1,5-c]pyrimidine.

68. A compound or salt according to claim 1, wherein the compound is 8-ethyl-7-[2-(5-fluoro-2-methyl-phenyl)-imidazol-1-ylmethyl]-[1,2,4]triazolo[1,5-c]pyrimidine.

69. A compound or salt according to claim 1, wherein the compound is 8-ethyl-7-[2-(5-fluoro-2-methyl-phenyl)-imidazol-1-ylmethyl]-2-methyl-[1,2,4]triazolo[1,5-c]pyrimidine.

70. A compound or salt according to claim 1, wherein the compound is 2-ethyl-7-[2-(3-fluoro-pyridin-2-yl)-imidazol-1-yl methyl]-8-propyl-[1,2,4]triazolo[1,5-c]pyrimidine.

71. A compound or salt according to claim 1, wherein the compound is 2-difluoromethyl-7-[2-(3-fluoro-pyridin-2-yl)-imidazol-1-ylmethyl]-8-propyl-[1,2,4]triazolo[1,5-c]pyrimidine.

72. A compound or salt according to claim 1, wherein the compound is 7-(2-(3-fluoro-pyridin-2-yl)-imidazol-1-ylmethyl]-2-phenyl-8-propyl-[1,2,4]triazolo[1,5-c]pyrimidine.

73. A compound or salt according to claim 1, wherein the compound is 7-[2-(3-fluoro-pyridin-2-yl)-imidazol-1-ylmethyl]-2-isopropyl-8-propyl-[1,2,4]triazolo[1,5-c]pyrimidine.

74. A compound or salt according to claim 1, wherein the compound is 2-fluoromethyl-7-[2-(3-fluoro-pyridin-2-yl)-imidazol-1-ylmethyl]-8-propyl-[1,2,4]triazolo[1,5-c]pyrimidine.

75. A compound or salt according to claim 1, wherein the compound is 8-(2,2-difluoro-ethyl)-7-[2-(3-fluoro-pyridin-2-yl)-imidazol-1-ylmethyl]-2-methyl-[1,2,4]triazolo[1,5-c]pyrimidine.

76. A compound or salt according to claim 1, wherein the compound is 2-[1-(8-propyl-[1,2,4]triazolo[1,5-c]pyrimidin-7-ylmethyl)-1H-imidazol-2-yl[-nicotinonitrile.

77. A compound or salt according to claim 1, wherein the compound is 6-[1-(8-propyl-[1,2,4]triazolo[1,5-c]pyrimidin-7-ylmethyl)-1H-imidazol-2-yl[-pyridine-2-carbonitrile.

78. A compound or salt according to claim 1, wherein the compound is 7-{[2-(3-fluoropyridin-2-yl)-1H-imidazol-1-yl]methyl}-8-propyl-2-pyrrolidin-1-yl[1,2,4]triazolo[1,5-c]pyrimidine.

79. A compound or salt according to claim 1, wherein the compound is 7-[2-(3-fluoro-pyridin-2-yl)-imidazol-1-ylmethyl]-2-isopropoxy-8-propyl-[1,2,4]triazolo[1,5-c]pyrimidine.

80. A compound or salt according to claim 1, wherein the compound is 7-[2-(6-fluoro-pyridin-2-yl)-imidazol-1-ylmethyl]-2,5-dimethyl-8-propyl-[1,2,4]triazolo[1,5-c]pyrimidine.

81. A compound or salt according to claim 1, wherein the compound is 2-ethyl-7-[2-(6-fluoro-pyridin-2-yl)-imidazol-1-ylmethyl]-5-methyl-8-propyl-[1,2,4]triazolo[1,5-c]pyrimidine.

82. A compound or salt according to claim 1, wherein the compound is 2,8-diethyl-7-(2-(5-fluoro-2-methyl-phenyl)-imidazol-1-ylmethyl]-[1,2,4]triazolo[1,5-c]pyrimidine.

83. A compound or salt according to claim 1, wherein the compound is 7-[2-(3-fluoro-pyridin-2-yl)-imidazol-1-ylmethyl]-8-methoxymethyl-2-methyl-[1,2,4]triazolo[1,5-c]pyrimidine.

84. A compound or salt according to claim 1, wherein the compound is 1-{7-[2-(3-fluoro-pyridin-2-yl)-imidazol-1-yl-methyl]-2methyl-[1,2,4]triazolo[1,5-c]pyrimidin-8-yl}-propan-1-ol.

85. A compound or salt according to claim 1, wherein the compound is 1-{7-[2-(3-fluoro-pyridin-2-yl)-imidazol-1-yl-methyl]-2-methyl-[1,2,4triazolo[1,5-c ]pyrimidin-8-yl}-propan-1-ol.

86. A compound or salt according to claim 1, wherein the compound is {7-[2-(3-fluoro-pyridin-2-yl)-imidazol-1-ylm-ethyl]-8-propyl-[1,2,4triazolo [1,5-c ]pyrimidin-2-yl}-methanol.

87. A compound or salt according to claim 1, wherein the compound is 7-[2-(3-fluoro-pyridin-2-yl )-imidazol-1 -ylm-ethyl]-2-methyl-8-propenyl-[1,2,4]triazolo[1,5-c]pyrimidine.

88. A compound or salt according to claim 1, wherein the compound is 7-(2-(3-fluoro-pyridin-2-yl )-imidazol-1 -ylm-ethyl]-8-propyl-2-pyridin-3-yl-[1,2,4]triazolo[1,5-c]pyrimidine.

89. A compound or salt according to claim 1, wherein the compound is 8-(3-benzyloxy-propyl )-7-[2-(3-fluoro-pyridi n-2-yl )-imidazol-1 -ylmethyl]-2-methyl[1,2,4]triazolo[1,5-c]pyrimidine.

90. A compound or salt according to claim 1, wherein the compound is 8-(2-benzyloxy-ethyl )-7-[2-(3-fluoro-pyridin-2-yl)-imidazol- I -ylmethyl]-2-methyl-(1,2,4]triazolo[1,5-c]pyrimidine.

91. A compound or salt according to claim 1, wherein the compound is 3-{7-[2-(3-fluoro-pyridin-2-yl)-imidazol-1-yl-methyl]-2-methyl-[1,2,4]triazolo[1,5-c]pyrimidin-8-yl}-propan-1 -01.

92. A compound or salt according to claim 1, wherein the compound is 8-(2-fluoro-ethyl)-7-[2-(3-fluoro-pyridin-2-yl)-imidazol-1-ylmethyl]-2-methyl-[1,2,4]triazolo[1,5-c]pyrimidine.

93. A compound or salt according to claim 1, wherein the compound is 8-(3-chloro-propyl)-7-[2-(3-fluoro-pyridin-2-yl)-imidazol-1-ylmethyl]-2-methyl-[1,2,4]triazolo[1,5-c]pyrimidine.

94. A compound or salt according to claim 1, wherein the compound is 2-{7-[2-(3-fluoro-pyridin-2-yl)-imidazol-1-yl-methyl]-2-methyl-[1,2,4]triazolo[1,5-c]pyrimidin-8-yl}-ethanol.

95. A compound or salt according to claim 1, wherein the compound is 8-(3-fluoro-propyl )-7-(2-(3-fluoro-pyridin-2-yl )-imidazol- l-yl methyl]-2-methyl-[1,2,4]triazolo(1,5-c]pyrimidine.

96. A compound or salt according to claim 1, wherein the compound is 8-(3-fluoro-propyl )-7-(2-(3-fluoro-pyridin-2-yl )-imidazol-1-ylmethyl]-[1,2,4]triazolo[1,5-c]pyrimidine.

97. A compound or salt according to claim 1, wherein the compound is 8-ethyl-7-{[2-(3-fluoropyridin-2-yl)-1H-imi-dazol-1-yl]methyl}[1,2,4]triazolo[1,5-c]pyrimidine.

98. A compound or salt according to claim 1, wherein the compound is 8-propyl-7-[2-(6-trifluoromethyl-pyridin-2-yl)-imidazol-1-ylmethyl]-[1,2,4]triazolo[1,5-c]pyrimidine.

99. A compound or salt according to claim 1, wherein the compound is 2-{1-[8-(3-fluoro-propyl)-[1,2,4]triazolo[1,5-c]pyrimidin-7-ylmethyl]-1H-imidazol-2-yl}-nicotinonitrile.

100. A compound or salt according to claim 1, wherein the compound is 6-{1-[8-(3-fluoro-propyl)-[1,2,4]triazolo[1,5-c]pyrimidin-7-ylmethyl]-1H-imidazol-2-yl}-pyridine-2-carbonitrile.

101. A compound or salt according to claim 1, wherein the compound is 7-[2-(3-fluoro-pyridin-2-yl)-imidazol-1-ylm-ethyl]-8-propyl-[1,2,4]triazolo[1,5-c]pyrimidine-2-carboxylic acid ethyl ester.

102. A compound or salt according to claim 1, wherein the compound is 7-[2-(3-fluoro-pyridin-2-yl)-imidazol-1-ylm-ethyl]-8-propyl-[1,2,4]triazolo[1,5-c]pyrimidine-2-carboxylic acid amide.

103. A compound or salt according to claim 1, wherein the compound is 7-[2-(3-fluoro-pyridin-2-yl)-imidazol-1-ylm-ethyl]-8-propyl-[1,2,4]triazolo[1,5-c]pyrimidine-2-carbonitrile.

104. A compound or salt according to claim 1, wherein the compound is 7-[4-chloro-2-(3-fluoro-pyridin-2-yl)-imida-zol-1-ylmethyl]-8-propyl-[1,2,4]triazolo[1,5-c]pyrimidine.

105. A compound or salt according to claim 1, wherein the compound is 2-[1-(2-Methyl-8-propyl-[1,2,4]triazolo[1,5-c]pyrimidine-7-ylmethyl)-1H-imidazol-2-yl]-nicotinonitrile.

106. A compound or salt according to claim 1, wherein the compound is 8-ethoxy-7-[2-(3-fluoro-pyridin-2-yl)-imida-zol-1-ylmethyl]-2-methyl-[1,2,4]triazolo[1,5-c]pyrimidine.

107. A compound or salt according to claim 1, wherein the compound is 8-ethyl-7-{[2-(3-fluoropyridin-2-yl)-1H-imi-dazol-1-yl]methyl}-2-methyl[1,2,4]triazolo[1,5-c]pyrimi-dine.

108. A compound or salt according to claim 1, wherein the compound is 8-ethoxy-7-{[2-(3-fluoropyridin-2-yl)-1H-imi-dazol-1-yl]methyl}[1,2,4]triazolo[1,5-c]pyrimidine.

109. A compound or salt according to claim 1, wherein the compound is 7-{[2-(3-fluoropyridin-2-yl )-1H-imidazol-1-yl]methyl}-2-methoxy-8-propyl[1,2,4]triazolo[5-c]pyrimi-dine.

110. A compound or salt according to claim 1, wherein the compound is 2-ethoxy-7-{[2-(3-fluoropyridin-2-yl)-1H-imi-dazol-1-yl]methyl}-8-propyl[1,2,4]triazolo[1,5-c]pyrimi-dine.

111. A compound or salt according to claim 1, wherein the compound is 7-{[2-(3-fluoropyridin-2-yl)-1H-imidazol-1-yl]methyl}-8-propyl[1,2,4]triazolo[1,5-c]pyrimidin-2-amine.

112. A compound or salt according to claim 1, wherein the compound is 2-(7-{f2-(3-fluoropyridin-2-yl)-1H-imidazol-1-yl]methyl}-8-propyl[1,2,4]triazolo[1,5-c]pyrimidin-2-yl)propan-2-ol.

113. A compound or salt according to claim 1, wherein the compound is 2-(ethoxymethyl)-7-{[2-(6-fluoropyridin-2-yl)-1H-imidazol-1-yl]methyl}-8-propyl[1,2,4]triazolo[1,5-c]pyrimidine.

114. A compound or salt according to claim 1, wherein the compound is methyl 7-{[2-(3-fluoropyridin-2-yl)-1H-imi-dazol-1-yl]methyl}-8-propyl[1,2,4]triazolo[1,5-c]pyrimi-dine-2-carboxylate.

115. A compound or salt according to claim 1, wherein the compound is 2-(7-{[2-(6-fluoropyridin-2-yl)-1H-imidazol-1-yl]methyl}-8-propyl[1,2,4]triazolo[1,5-c]pyrimidin-2-yl)propan-2-ol.

116. A compound or salt according to claim 1, wherein the compound is 6-(1-{[2-(methoxymethyl)-8-propyl[1,2,4]tria-zolo[1,5-c]pyrimidin-7-yl]methyl}-1H-imidazol-2-yl)pyri-dine-2-carbonitrile.

117. A compound or salt according to claim 1, wherein the compound is 7-{[2-(3-fluoropyridin-2-yl)-1H-imidazol-1-yl]methyl}-8-propyl-2-(tetrahydrofuran-2-yl)[1,2,4]triazolo[1,5-c]pyrimidine.

118. A compound or salt according to claim 1, wherein the compound is 7-{[2-(3-fluoropyridin-2-yl)-1H-imidazol-1-yl]methyl}-8-propyl-2[(2,2, 2-trifluoroethoxy)methyl][1,2,4]triazolo[1,5-c]pyrimidine.

119. A compound or salt according to claim 1, wherein the compound is 2-chloro-7-{[2-(3-fluoropyridin-2-yl)-1H-imidazol-1-yl]methyl}-8-propyl[1,2,4]triazolo[1,5-c]pyrimidine.

120. A compound or salt according to claim 1, wherein the compound is 7-{[2-(3-fluoropyridin-2-yl)-1H-imidazol-1-yl]methyl}-8-propyl-2-(2,2,2-trifluoroethyl) [1,2,4]triazolo[1,5-c]pyrimidine.

121. A compound or salt according to claim 1, wherein the compound is 7-{[2-(3-fluoropyridin-2-yl)-1H-imidazol-1-yl]methyl}-8-propyl-2-(1,3-thiazol-2-yl)[1,2,4]triazolo[1,5-c]pyrimidine.

122. A compound or salt according to claim 1, wherein the compound is 7-{(2-(3-fluoropyridin-2-yl)-1H-imidazol-1-yl]methyl}-N,N,8-tripropy[1,2,4]triazolo[1,5-c]pyrimidin-2-amine.

123. A compound or salt according to claim 1, wherein the compound is 6-(1-{[2-(ethoxymethyl)-8-propyl[1,2,4]triazolo[1,5-c]pyrimidin-7-yl]methyl}-1h-imidazol-2-yl)pyridine-2-carbonitrile.

124. A compound or salt according to claim 1, wherein the compound is 2-(ethoxymethyl )-7-{(2-(3-fluoropyridin-2-yl)-1H-imidazol-1-yl]methyl}-8-propyl[1,2,4]triazolo[1,5-c]pyrimidine.

125. A compound or salt according to claim 1, wherein the compound is 6-{1-[(2-methyl-8-propyl[1,2,4]triazolo[1,5-c]pyrimidin-7-yl)methyl]-1H-imidazol-2-yl}pyridine-2-carbonitrile.

126. A compound or salt according to claim 1, wherein the compound is 7-{[2-(3-fluoropyridin-2-yl)-1H-imidazol-1-yl]methyl}-2-(isopropoxymethyl)-8-propyl[1,2,4]triazolo[1,5-c]pyrimidine.

127. A compound or salt according to claim 1, wherein the compound is 6-(1-{[2-(isopropoxymethyl)-8-propyl[1,2,4]triazolo[1,5-c]pyrimidin-7-yl]methyl}-1H-imidazol-2-yl)pyridine-2-carbonitrile.

128. A compound or salt according to claim 1, wherein the compound is 2-[(cyclopentyloxy)methyl]-7-{[2-(3-fluoropyridin-2-yl)-1H-imidazol-1-yl]methyl}-8-propyl[1,2,4]triazolo[1,5-c]pyrimidine.

129. A compound or salt according to claim 1, wherein the compound is 7-{[2-(5-fluoropyridin-2-yl)-1H-imidazol-1-yl]methyl}-2-methyl-8-propyl[1,2,4]triazolo[1,5-c]pyrimidine.

130. A compound or salt according to claim 1, wherein the compound is 3-{1-[(8-ethyl[1,2,4]triazolo[1,5-c]pyrimidin-7-yl)methyl]-1H-imidazol-2-yl}benzonitrile.

131. A compound or salt according to claim 1, wherein the compound is 8-ethyl-7-{[2-(5-fluoro-2-methoxyphenyl)-1H-imidazol-1-yl]methyl}[1,2,4]triazolo[1,5-c]pyrimidine.

132. A compound or salt according to claim 1, wherein the compound is 8-ethyl-7-{[2-(3-fluorophenyl)-1H-imidazol-1-yl]methyl}[1,2,4]triazolo[1,5-c]pyrimidine.

133. A compound or salt according to claim 1, wherein the compound is 7-{[2-(6-chloropyridin-2-yl)-1H-imidazol-1-yl]methyl}-8-ethyl[1,2,4]triazolo[1,5-c]pyrimidine.

134. A compound or salt according to claim 1, wherein the compound is 7-{[2-(2-chlorophenyl)-1H-imidazol-1-yl]methyl}-8-ethyl[1,2,4]triazolo[1,5-c]pyrimidine.

135. A compound or salt according to claim 1, wherein the compound is 7-{[2-(3-fluoropyridin-2-yl)-1H-imidazol-1-yl]methyl}-8-propyl[1,2,4]triazolo[1,5-c]pyrimidine-2-carboxylic acid.

136. A compound or salt according to claim 1, wherein the compound is 6-{1-[(8-ethyl[1,2,4]triazolo[1,5-c]pyrimidin-7-yl)methyl]-1H-imidazol-2-yl}pyridine-2-carbonitrile.

137. A compound or salt according to claim 1, wherein the compound is 8-ethyl-7-[2-(3-trifluoromethyl-phenyl)-imidazol-1-ylmethyl]-[1,2,4]triazolo[4,3-c]pyrimidine.

138. A compound or salt according to claim 1, wherein the compound is 7-[2-(3-fluoro-pyridin-2-yl)-imidazol-1-ylmethyl]-3-methyl-8-propyl-[1,2,4]triazolo[4,3-c]pyrimidine.

139. A compound or salt according to claim 1, wherein the compound is 7-[2-(3-fluoro-pyridin-2-yl)-imidazol-1-ylmethyl]-8-propyl-[1,2,4]triazolo[4,3-c]-pyrimidine.

140. A compound or salt according to claim 1, wherein the compound is 7-[2-(3-fluoro-pyridin-2-yl)-imidazol-1-ylmethyl]-3-phenyl-8-propyl-[1,2,4]-triazolo[4,3-c]pyrimidine.

141. A compound or salt according to claim 1, wherein the compound is 3-difluoromethyl-7-[2-(3-fluoro-pyridin-2-yl)-imidazol-1-ylmethyl]-8-propyl-[1,2,4]triazolo[4,3-c]pyrimidine.

142. A compound or salt according to claim 1, wherein the compound is 7-[2-(6-fluoro-pyridin-2-yl)-imidazol-1-ylmethyl]-3-methyl-8-propyl-[1,2,4]triazolo[4,3-c]-pyrimidine.

143. A compound or salt according to claim 1, wherein the compound is 7-[2-(6-fluoro-pyridin-2-yl)-imidazol-1-ylmethyl]-8-propyl-[1,2,4]triazolo[4,3-c]pyrimidine.

144. A compound or salt according to claim 1, wherein the compound is 7-[2-(3-fluoro-pyridin-2-yl)-imidazol-1-ylmethyl]-8-propyl-[1,2,4]triazolo[4-c]pyrimidine.

145. A compound or salt according to claim 1, wherein the compound is 1-{7-[2-(3-fluoro-pyridin-2-yl)-imidazol-1-ylmethyl]-8-propyl-[1,2,4]triazolo[4,3-c]pyrimidin-3-yl}-ethanol.

146. A compound or salt according to claim 1, wherein the compound is 7-[2-(3-fluoro-pyridin-2-yl)-imidazol-1-ylmethyl]-8-propyl-3-trifluoromethyl-[1,2,4]triazolo[4,3-c]pyrimidine.

147. A compound or salt according to claim 1, wherein the compound is 7-[2-(3-fluoro-pyridin-2-yl)-imidazol-1-ylmethyl]-3-methoxy-methyl-8-propyl-[1,2,4]triazolo[4,3-c]pyrimidine.

148. A compound or salt according to claim 1, wherein the compound is 7-[2-(6-fluoro-pyridin-2-yl)-imidazol-1-ylmethyl]-3-methoxymethyl-8-propyl-[1,2,4]triazolo[4,3-c]pyrimidine.

149. A compound or salt according to claim 1, wherein the compound is 3-cyclobutyl-7-[2-(6-fluoro-pyridin-2-yl)-imidazol-1-ylmethyl]-8-propyl-[1,2,4]triazolo[4,3-c]pyrimidine.

150. A compound or salt according to claim 1, wherein the compound is 8-propyl-7-(2-pyridin-2-yl-imidazol-1-ylmethyl)-[1,2,4]-triazolo[4,3-c]pyrimidine.

151. A compound or salt according to claim 1, wherein the compound is 7-[2-(2,5-difluoro-phenyl)-imidazol-1-ylmethyl]-3-methyl-8-propyl-[1,2,4]triazolo[4,3-c]pyrimidine.

152. A compound or salt according to claim 1, wherein the compound is 7-[2-(6-methoxy-pyridin-2-yl)-imidazol-1-ylmethyl]-8-propyl-[1,2,4]triazolo[4,3-c]pyrimidine.

153. A compound or salt according to claim 1, wherein the compound is 3-methyl-8-propyl-7-(2-thiazol-2-yl-imidazol-1-ylmethyl)-[1,2,4]triazolo[4,3-c]pyrimidine.

154. A compound or salt according to claim 1, wherein the compound is 3-methyl-8-propyl-7-(2-pyridin-2-yl-imidazol-1-ylmethyl)-[1,2,4]triazolo[4,3-c]pyrimidine.

155. A compound or salt according to claim 1, wherein the compound is 6-[1-(8-propyl-[1,2,4]triazolo[4,3-c]pyrimidin-7-ylmethyl)-1H-imidazol-2-yl]-pyridin-2-ol.

156. A compound or salt according to claim 1, wherein the compound is 7-[2-(2,6-difluoro-phenyl)-imidazol-1-ylmethyl]-8-propyl-[1,2,4]triazolo[4,3-c]pyrimidine.

157. A compound or salt according to claim 1, wherein the compound is 8-propyl-7-(2-thiophen-2-yl-imidazol-1-ylmethyl)-[1,2,4]-triazolo[4,3-c]pyrimidine.

158. A compound or salt according to claim 1, wherein the compound is 3-methyl-8-propyl-7-(2-pyridazin-3-yl-imidazol-1-ylmethyl)-[1,2,4]triazolo[4,3-c]pyrimidine.

159. A compound or salt according to claim 1, wherein the compound is 7-[2-(2,5-difluoro-phenyl)-imidazol-1-ylmethyl]-8-ethyl-[1,2,4]triazolo[4,3-c]pyrimidine.

160. A compound or salt according to claim 1, wherein the compound is 7-[2-(2,5-difluoro-phenyl)-imidazol-1-ylmethyl]-8-ethyl-3-methyl-[1,2,4]triazolo[4,3-c]pyrimidine.

161. A compound or salt according to claim 1, wherein the compound is 8-ethyl-7-[2-(5-fluoro-2-methyl-phenyl)-imidazol-1-ylmethyl]-[1,2,4]triazolo[4,3-c]pyrimidine.

162. A compound or salt according to claim 1, wherein the compound is 8-ethyl-7-(2-(5-fluoro-2-methyl-phenyl)-imidazol-1-yl-methyl]-3-methyl-[1,2,4]triazolo[4,3-c]pyrimidine.

163. A compound or salt according to claim 1, wherein the compound is 3-ethyl-7-[2-(3-fluoro-pyridin-2-yl)-imidazol-1-ylmethyl]-8-propyl-[1,2,4]triazolo[4,3-c]pyrimidine.

164. A compound or salt according to claim 1, wherein the compound is 7-[2-(6-fluoro-pyridin-2-yl)-imidazol-1-ylmethyl]-3,5-dimethyl-8-propyl-[1,2,4]triazolo[4,3-c]pyrimidine.

165. A compound or salt according to claim 1, wherein the compound is 3-ethyl-7-[2-(6-fluoro-pyridin-2-yl)-imidazol-1-ylmethyl]-5-methyl-8-propyl-[1,2,4]triazolo[4,3-c]pyrimidine.

166. A compound or salt according to claim 1, wherein the compound is 3,8-diethyl-7-[2-(5-fluoro-2-methyl-phenyl)-imidazol-1-ylmethyl]-[1,2,4]triazolo[4,3-c]pyrimidine.

167. A compound or salt according to claim 1, wherein the compound is 7-[2-(3-fluoro-pyridin-2-yl)-imidazol-1 -ylmethyl]-8-methoxymethyl-[1,2,4]triazolo[4,3-c]pyrimidine.

168. A compound or salt according to claim 1, wherein the compound is 7-[2-(3-fluoro-pyridin-2-yl)-imidazol-1-ylmethyl]-3-isopropyl-8-propyl-[1,2,4]triazolo[4,3-c]pyrimidine.

169. A compound or salt according to claim 1, wherein the compound is 1-{7-[2-(6-fluoro-pyridin-2-yl)-imidazol-1-ylmethyl]-3-methyl-[1,2,4]triazolo[4,3-c]pyrimidin-8-yl}-propan-1-ol.

170. A compound or salt according to claim 1, wherein the compound is 1-{7-[2-(3-fluoro-pyridin-2-yl)-imidazol-1-ylmethyl]-3-methyl-[1,2,4]triazolo[4,3-c]pyrimidin-8-yl}-propan-1 -ol.

171. A compound or salt according to claim 1, wherein the compound is {7-[2-(3-fluoro-pyridin-2-yl)-imidazol-1-ylmethyl[-8-propyl-[2,4]triazolo[4,3-c]pyrimidin-3-yl}-methanol.

172. A compound or salt according to claim 1, wherein the compound is 7-[2-(3-fluoro-pyridin-2-yl)-imidazol-1-ylmethyl]-3-methyl-8-propenyl-[1,2,4]triazolo[4,3-c]pyrimidine.

173. A compound or salt according to claim 1, wherein the compound is 7-[2-(3-fluoro-pyridin-2-yl)-imidazol-1-ylmethyl]-8-propyl-3-pyridin-3-yl-[1,2,4]triazolo[4,3-c]pyrimidine.

174. A compound or salt according to claim 1, wherein the compound is 7-[2-(3-fluoro-pyridin-2-yl)-imidazol-1-ylmethyl]-8-methoxymethyl-3-methyl-[1,2,4]triazolo[4,3-c]pyrimidine.

175. A compound or salt according to claim 1, wherein the compound is 3-{7-[2-(3-fluoro-pyridin-2-yl)-imidazol-1-ylmethyl]-3-methyl-[1,2,4]triazolo4,3-c]pyrimidin-8-yl}-propan-1 -ol.

176. A compound or salt according to claim 1, wherein the compound is 8-(2-fluoro-ethyl)-7-[2-(3-fluoro-pyridin-2-yl)-imidazol-1-ylmethyl]-3-methyl-1,2,4]triazolo[4,3-c]pyrimidine.

177. A compound or salt according to claim 1, wherein the compound is 2-{7-[2-(3-fluoro-pyridin-2-yl)-imidazol-1-ylmethyl]-3-methyl-[1,2,4]triazolo[4,3-c]pyrimidin-8-yl}-ethanol.

178. A compound or salt according to claim 1, wherein the compound is 8-(3-fluoro-propyl)-7-[2-(3-fluoro-pyridin-2-yl)-imidazol-1-ylmethyl]-3-methyl-[1,2,4]triazolo[4,3-c]pyrimidine.

179. A compound or salt according to claim 1, wherein the compound is 8-(3-fluoro-propyl)-7-[2-(3-fluoro-pyridin-2-yl)-imidazol-1-ylmethyl]-[1,2,4]triazolo[4,3-c]pyrimidine.

180. A compound or salt according to claim 1, wherein the compound is 8-propyl-7-[2-(6-trifluoromethyl-pyridin-2-yl)-imidazol-1-ylmethyl]-[1,2,4]triazolo[4,3-c]pyrimidine.

181. A compound or salt according to claim 1, wherein the compound is 2-{1-[8-(3-fluoro-propyl)-[1,2,4]triazolo[4,3-c]pyrimidin-7-ylmethyl]-1H-imidazol-2-yl}-nicotinonitrile.

182. A compound or salt according to claim 1, wherein the compound is 6-{1-[8-(3-fluoro-propyl)-[1,2,4]triazolo[4,3-c]pyrimidin-7-ylmethyl]-1H-imidazol-2-yl}-pyridine-2-carbonitrile.

183. A compound or salt according to claim 1, wherein the compound is 7-[2-(3-fluoro-pyridin-2-yl)-imidazol-1-ylmethyl]-8-propyl-[1,2,4]triazolo[4,3-c]pyrimidine-3-carboxylic acid ethyl ester.

184. A compound or salt according to claim 1, wherein the compound is 7-[2-(3-fluoro-pyridin-2-yl)-imidazol-1-ylmethyl]-8-propyl-[1,2,4]triazolo[4,3-c]pyrimidine-3-carboxylic acid amide.

185. A compound or salt according to claim 1, wherein the compound is 7-[2-(3-fluoro-pyridin-2-yl)-imidazol-1-ylmethyl]-8-propyl-[1,2,4]triazolo[4,3-c]pyrimidine-3-carbonitrile.

186. A compound or salt according to claim 1, wherein the compound is 7-[4-chloro-2-(3-fluoro-pyridin-2yl)-imidazol-1-ylmethyl]-8-propyl-[1,2,4]triazolo[4,3-c]pyrimidine.

187. A compound or salt according to claim 1, wherein the compound is 2-[1-(3-Methyl-8-propyl-[1,2,4]triazolo[4,3-c]pyrimidine-7-ylmethyl)-1H-imidazol-2-yl]-nicotinonitrile.

188. A compound or salt according to claim 1, wherein the compound is 7-[2-(6-fluoro-pyridin-2-yl)-imidazol-1-ylmethyl]-1-methyl-8-propyl-imidazo[1,5-c]pyrimidine.

189. A compound or salt according to claim 1, wherein the compound is 7-[2-(3-fluoro-pyridin-2-yl)-imidazol-1-ylmethyl]-1-methyl-8-propyl-imidazo[1,5-c]pyrimidine.

190. A method for the treatment of insomnia, comprising administering to a patient in need of such treatment a therapeutically effective amount of a compound or salt according to claim 1.

* * * * *